(12) United States Patent
Moss et al.

(10) Patent No.: US 9,139,613 B2
(45) Date of Patent: Sep. 22, 2015

(54) MACROCYCLIC COMPOUNDS AND METHODS FOR THEIR PRODUCTION

(75) Inventors: Steven James Moss, Cambridge (GB); Matthew Alan Gregory, Cambridge (GB); Barrie Wilkinson, Cambridge (GB)

(73) Assignee: NEUROVIVE PHARMACEUTICAL AB, Lund (SE)

( * ) Notice: Subject to any disclaimer, the term of this patent is extended or adjusted under 35 U.S.C. 154(b) by 0 days.

(21) Appl. No.: 14/006,341

(22) PCT Filed: Mar. 29, 2012

(86) PCT No.: PCT/GB2012/050707
§ 371 (c)(1),
(2), (4) Date: Oct. 17, 2013

(87) PCT Pub. No.: WO2012/131377
PCT Pub. Date: Oct. 4, 2012

(65) Prior Publication Data
US 2014/0038885 A1 Feb. 6, 2014

(30) Foreign Application Priority Data

Mar. 29, 2011 (GB) .................................. 1105293.3
Aug. 8, 2011 (GB) .................................. 1113629.8
Feb. 7, 2012 (GB) .................................. 1202060.8

(51) Int. Cl.
*A61K 38/06* (2006.01)
*C07K 5/083* (2006.01)
(Continued)

(52) U.S. Cl.
CPC ............. *C07K 5/06078* (2013.01); *A61K 38/06* (2013.01); *C07D 498/04* (2013.01); *C07D 498/06* (2013.01); *C07K 5/06191* (2013.01); *C07K 5/0808* (2013.01)

(58) Field of Classification Search
None
See application file for complete search history.

(56) References Cited

U.S. PATENT DOCUMENTS

2014/0080837 A1* 3/2014 Moss et al. ............... 514/252.03

FOREIGN PATENT DOCUMENTS

WO 2006/138507 12/2006
WO 2011/098805 8/2011
(Continued)

OTHER PUBLICATIONS

Sedrani, R., et al. "Sanglifehrin-cyclophilin interaction: degradation work, synthetic macrocyclic analogues, X-ray crystal structure, and binding data." J Am Chem Soc. Apr. 2, 2003;125(13):3849-59.
(Continued)

*Primary Examiner* — Jeffrey E Russel
(74) *Attorney, Agent, or Firm* — Robert C. Netter; Kathleen D. Rigaut; Dann, Dorfman, Herrell & Skillman

(57) ABSTRACT

There is provided inter alia compounds of formula (I):

Formula (I)

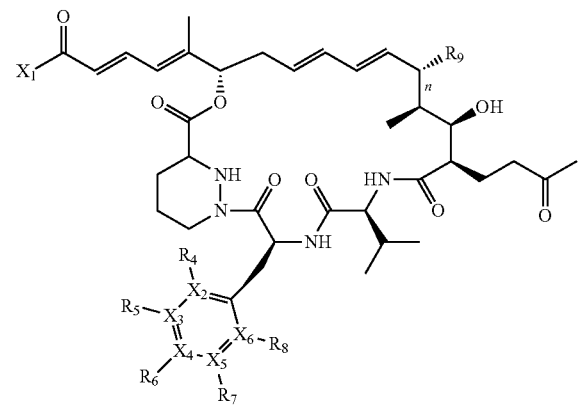

Figure 1:
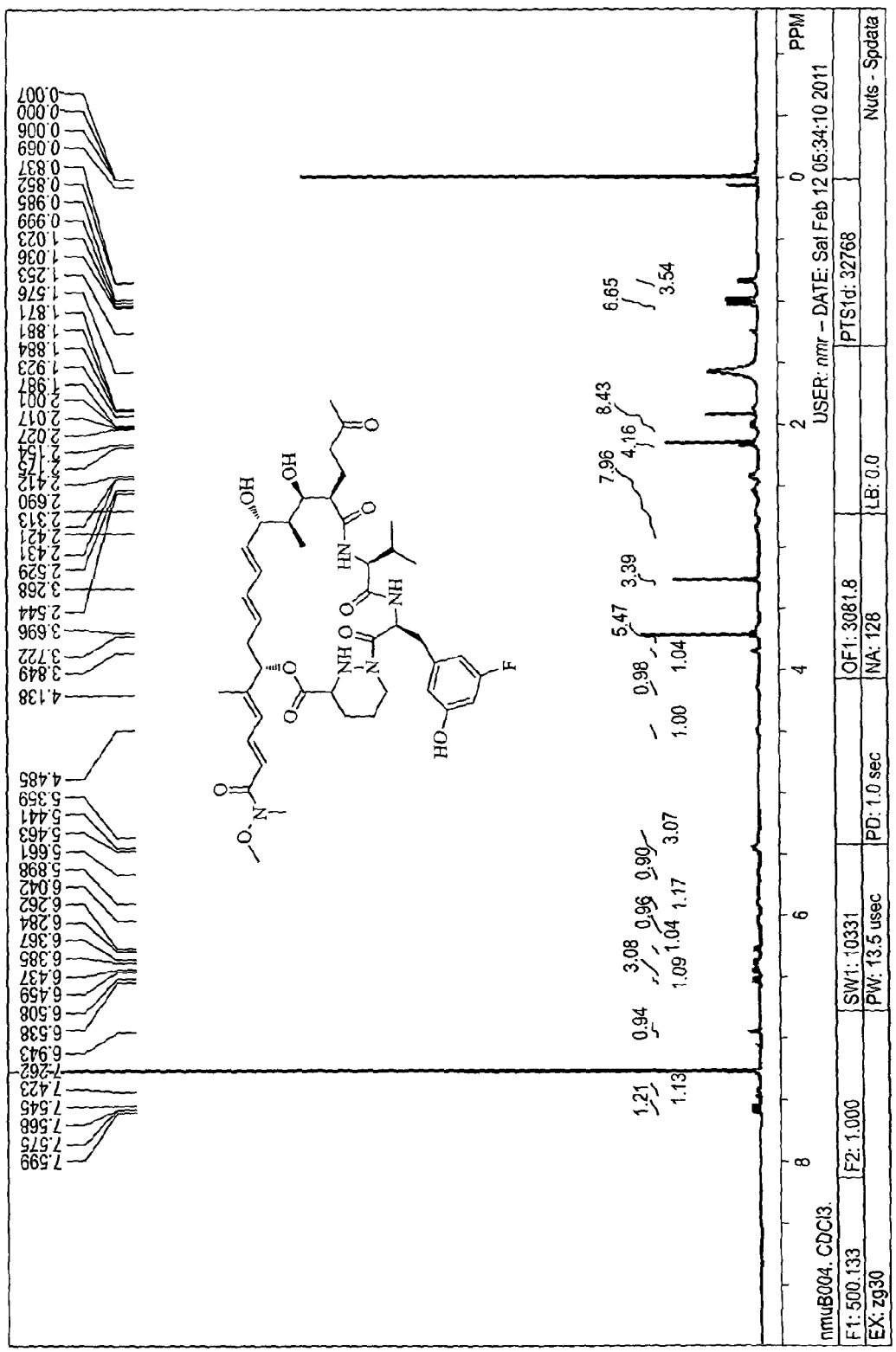

for use in treatment of viral infection or as an immunosuppressant.

23 Claims, 8 Drawing Sheets

(51) Int. Cl.
*C07K 5/065* (2006.01)
*C07K 5/06* (2006.01)
*C07D 498/04* (2006.01)
*C07D 498/06* (2006.01)

(56) References Cited

FOREIGN PATENT DOCUMENTS

| WO | 2011/098808 | 8/2011 |
|---|---|---|
| WO | 2011/098809 | 8/2011 |

OTHER PUBLICATIONS

Banteli, R., et al. "Synthesis of derivatives of the novel cyclophilin-binding immunosuppressant sanglifehrin A with reduced numbers of polar functions." Bioorg Med Chem Lett. Jun. 18, 2001; 11(12):1609-12.

Metternich, R., et al. "Toward a Total Synthesis of the Immunosuppressant Sanglifehrin. A. Preparation of Two Relay Compounds by Degradation and Their Use in the Reassembly of the Natural Product." J. Org. Chem. 1999;64:9632-9639.

Kallen, J., et al. "Structure of human cyclophilin a in complex with the novel immunosuppressant sanglifehrin A at 1.6 A resolution." J Biol Chem. Jun. 10, 2005 ;280(23):21965-71. Epub Mar. 16, 2005.

Fehr, T., et al. "Sanglifehrins A, B, C and D, novel cyclophilin-binding compounds isolated from Streptomyces sp. A92-308110. II. Structure elucidation, stereochemistry and physico-chemical properties." J Antibiot (Tokyo). May 1999; 52(5):474-9.

Sanglier, J.J., et al. "Sanglifehrins A, B, C and D, novel cyclophilin-binding compounds isolated from Streptomyces sp. A92-308110. I. Taxonomy, fermentation, isolation and biological activity." J Antibiot (Tokyo). May 1999; 52 (5):466-73.

Moss, S.J., et al. "Sangamides, a new class of cyclophilin-inhibiting host-targeted antivirals for treatment of HCV infection." Med. Chem. Commun. Oct. 2011; 3:944-949.

Gregory, M.A., et al. "Preclinical characterization of naturally occurring polyketide cyclophilin inhibitors from the sanglifehrin family." Antimicrob Agents Chemother. May 2011; 55(5):1975-81. Epub Mar. 7, 2011.

Moss, S.J., et al. "BC556, a potent, pan-genotypic, high barrier to resistance, second generation cyclophilin inhibitor for treatment of chronic HCV infection." Poster presentation, 47th Annual meeting of the European Associate for the study of liver, EASL—The international Liver Congress, Barcelona, Spain—Apr. 18-22, 2012.

Moss, S.J., et al. "Preclinical characterization of novel cyclophilin inhibitors based on the polyketide, sanglifehrin." Poster presentation. 46th Annual meeting of the European Association for the study of the liver, EASL—The international Liver Congress, Berlin, Germany—Mar. 30-Apr. 3, 2011.

* cited by examiner

SEQUENCE LISTING

```
<160> NUMBER OF SEQ ID NOS: 8

<210> SEQ ID NO 1
<211> LENGTH: 77
<212> TYPE: DNA
<213> ORGANISM: Artificial
<220> FEATURE:
<223> OTHER INFORMATION: Primer

<400> SEQUENCE: 1
cgctctgtgg cgcctggttt ccaagcggct cgcggaccgg caccggcaca tgcataatta      60
accctcacta aagggcg                                                    77

<210> SEQ ID NO 2
<211> LENGTH: 78
<212> TYPE: DNA
<213> ORGANISM: Artificial
<220> FEATURE:
<223> OTHER INFORMATION: Primer

<400> SEQUENCE: 2
tggatgtatc gtcgcaggac gcccagaatt cacctgcgac gtcctccaga tgcattaata     60
```

```
cgactcacta tagggctc                                                    78
```

<210> SEQ ID NO 3
<211> LENGTH: 46596
<212> TYPE: DNA
<213> ORGANISM: Artificial
<220> FEATURE:
<223> OTHER INFORMATION: Cosmid

<400> SEQUENCE: 3

```
acaccggcca caccggcggc ggcctgcgtg tgcccgatgt tggacttcac cgaaccgagc      60
cacagcggct cgtcccgctc ctgcccgtag gtggcgagca gcgcctgcgc ctcgatcggg     120
tcgcccagcc gcgtgcccgt accgtgcgcc tccaccgcgt ccacgtccgc gggcgtgagc     180
ccggcaccgg agagcgcctg acggatcacc cgctgctgcg aaggaccgtt cggggccgtc     240
agaccgttcg acgcgccgtc ctggttgatc gcggtgccgc gtacgacggc cagtacctgg     300
tggccgtggc ggcgggcgtc ggagagccgt tccacgagga gcatgccggc gccctcggac     360
cagccggtgc cgtcggccgc ggcggcgaag gacttgcagc ggccgtccac ggccaggccg     420
cgctggcgga agaagtcgac gaagacgtcg ggggcggaca tgacggtgac accgccggcc     480
agcgccatcg agcactcgcc gctgcgcagc gcctggatcg cccagtgcag ggcgaccagc     540
gacgccgagc acgcggtgtc cacggtgacc gcagggcctt ccaggccgag gacgtaggcg     600
atgcggcccg acagcacgct ggcggagttg ccgatgccga cgtagccctc cgcgctctcg     660
acggtcctgc gcacgagctg gcatagtcc tggccgttgg tgccgaggta gacgccgacg      720
tccgcgccgc gcagggactt cgggtcgatg ccggcgcgtt cgacggcctc ccaggcggtc     780
tccagggcca ccgctgctg cgggtccatc gccagcgcct cgcgcggcga gatcccgaag       840
aagtccgcgt cgaacccggc gacgtccgcg aggaagccgc cctcccgcac gtacgacgtg     900
cccgcgtgct ccggatccgg gtggaagagg cccgcgaggt cccagccccg gtcgtcgggg     960
aacggggtga gcgcgtcgcg ctcgtcggcg agcagccgcc acaggtcctc gggcgaggtc    1020
acgccgccgg ggtaccggca cgccatgccg acgatcgcga tgggatcgtc gtcggcgggg    1080
cgggcgacgg cgggcaccgg cgccgtctcc tcggcgcgtt cgccgaggag ttcggccagc    1140
aggtggccgg ccaggagcg cgggttgggg tggtcgaaca cgagggtcgc gggcaggcgc      1200
agcccggtgg cggcggacag ccggttgcgg agttcgacgg cggtcagcga gtcgaagccc    1260
agttccttga cgcccggcc ggggtcacg gcggtgtcgt cggtgtggcc gaggaccacg       1320
gcggcgtgcg agcggacgag cgtgagcagg gtccgttcgc gttccgcggc ggtgagtccg    1380
gtgagctttc cggccagggt gtccggtccg gcgcccgcgg tggcggcgcg ccggacgggg    1440
ccacggacca gccggcgcat cagcgcgggt acgcggtga cgccggtggc gaacgaggtg      1500
aggtccagcc aggcggggac gacgacgggg gcggagccgg cggtggcgcg gtcgaacagg    1560
gcgagcgcgt cggcgtcgg cagcggcacc acgccgtcgc gggccgcgcg ccgcaggtcg      1620
gcgccgccca ggtggccggt catgccgctg gcgtgcgccc acaggcccca cacctgggag    1680
gtggcgggca ggccctgggc gcggcggtgt gccgcgagcg cgtccacgaa ggcgttgccc    1740
gccgcgtagt tgccctgtcc gggcgccccg aagaggccgg aggtggagga gaacagcacg    1800
aagacggccg gccggtgcgg ggcggtgagt tcgtgcaggt tccaggcggc gtcgaccttg    1860
gggcggagca ccttggcgag ccgctcgggg gtctgggagg cgatgacgcc gtcgtccagg    1920
acgccggcgg cgtggacgac tccggtcagg gggtgctcgg cggtgatccg gtcgagcagg    1980
```

-continued

```
gcggccagtt cggtgcggtc ggcggcgtcg caggcggcga cggtcacctc ggcgccgagg    2040
gcgcgcagtt cgccggcgag ggtcacggcg tcggggccg cgtcgccgcg ccgtccggcc      2100
aggaccagcc ggcgtacgcc gtgctcggtg accaggtggc gggcgcagag ggcgccgagc    2160
gtgccggtgc cgccggtgac gaggacgacg ccgtcgacg gccacagggc cgcctggctc      2220
gtgggctcgt cggtgcgcgg ggcgcggacc agccggggtg cgaggacccg gccggagcgc    2280
acggcgatct cggggttcgcc ggtggcgagg acagcgggca gctgttgcag tgcgtcgggg   2340
ccgtcgatgt cgaccagcac cagcctgccg gggtgttcgg cgcgggcgga gcggatcagg    2400
ccccacacgg gcgcgtgggc gaggtcgtg acgtcctcgt gctcgaccgg gaccgcgccg      2460
tgggtgagga cggccagacg ggtgccggcc agtcgctcgt cggcgagcca ctcctgaaga    2520
gcggtcagca cgcgccgggc gccggcgtgg gccgcgccgg cggtgtcgtc ggccgactgc    2580
tgccgacacg gcagcacgag ggtgccgggc acggtgtcca gggcggcgac ggcggcgagg    2640
tcggggcagg aggggtatcc gggcagcgga aggccgccga gcacggcgat gccgtcgacg    2700
tcggccgcgg gcagcggcac gggcgtccac tcgacccggt acagctcgtg gtcgcggccg    2760
gggccggccg tggccggcgg gcgcagggtc accgcgtcga cggtgagcac ggcggctccg    2820
ctgtcgtcgg tggcgtgcag ggtgaccgtg tgctcgcccg cggggtgcag gcgtacccgc    2880
agccgggtgg cgcccacggc gtgcagggtg acgccgtgcc aggcgccggg gaccaggccg    2940
gggtgtacgg ccgcgagggc gtcggtgagc agggcggggt gtacgcccca gccgccggcg    3000
gtctcgtcgg tcagctcaac ggtcacgtcg gtcagctcga cggtcacgtc ggtgtccggg    3060 tccctggcg cggcggccgg ggcggtgccg gtgtgcggga ggaggacgcc ggtcgcgtgc      3120
cgggtccagg gctggtcgtc gtcggcgtcg gcggggcggg agtggacggc gaccgggcgg    3180
gcgccgtcct cgttctccgc gcccaggtg acctggaggc ggcgggcttc gccgacggtg      3240
tcgagcggtg cctcctcggt cagttcgccg agcgtcctgc cgtcggccgc gtgcagggcc    3300
aggtcgagta cggcgccggc cggcagctcg gtgccggccg gcacgcgccc ggtgaacacc    3360
tgtccgccgg atccggcgag cggggtgacg gcgccgagca gcgggtgccc ggcgccggtc    3420
aggcccaggc cggcggcgtc ggaggcgacc gggccgctgg gccagaagcg gcggcgctgg    3480
aaggcgtagg tgggcaggtc gacgtggcgt ccgtcggggc agcccaccgt ccagtcgacg    3540
gacacgccgt ggacggcggc ctcggcgagc gaggtgagga ggcggcgcgg gccgtcctcg    3600
tcgcggcgga gggtgccgac gacgacggcg gtccgctcgg tggcctccgc cgtctcctgc    3660
acggcggccg tcagcaccgg gtgcgggctg atctccacga acacggcgtg gccggagtcg    3720
agcaggccgc gcaccacggg ctcgaaccgt acgggctccc gcaggttgcg gtaccagtag    3780
ccggcgtcga gccgtgtctc gccgaggggg ccgcccagca gggtggagtg gaaggcgatg    3840
ccggcctcac cgggccgcag ttcggcgagc gcggcgcgca actcggcttc gagggactcg    3900
acatgggccg agtgggaggc gtagtcgacc gcgatgcggc gcagtcgtac cccgtcggcc    3960
gaccaggcgg ccatcacctc gtccagcgca tcggggtcgc cgctgaggac caccgacgac    4020
gggccgttga gggcggcgac gcaaacgcgt ccggaccacg gtgcgagccg ccgtgtgacg    4080
gtggcctcgg gcaggcgac ggagaccatg ccgccgcgcc cggccagccg ctcggcgatg      4140
agccgcgacc gcagggcgac gatccggggcg ccgtccgcca gcgacagcac acccgccaca   4200
caagcagccg cgatctcccc ctgcgaatga ccgaccacag ccgacggcac gacaccgtac    4260
gaacgccaca cctccgccaa cgacaccatc accgcccaca acaccggctg aacgacatcc    4320
acccgctcca acgccaccgg atcacccagc acaccacgca acgaccagcc cacgaacggc    4380
```

```
tccaacgcca ccgcacactc agccatccgc cccgcgaaca ccggcgacga atccagcaga    4440
tccaccgcca tccccaccca ctgcgccccc tgacccggga acacgaacac cacccggccc    4500
tcacccggca acccgcaac  acccgacacc acaccctcca ccggctcccc cgcggccaac    4560
gccgccagag aagcccgcgc accggccaca tcagcggcca ccaccaccgc acgatgcggc    4620
aacaacgccc gcgacgcggc aagggaccag agaggtccac ccgggtccag gccggggtgg    4680
gtgtcgaggt gggcggcgag ccgggtggcc tgctcggcga gggcggcctg ggagcgggcg    4740
gagagcagcc acggcaccca gcgcggcgcg gcgccgcgcg cgggcgcggc cggttccgcc    4800
ggggcctcct ccaggatgag gtgggcgttg gtgccgctgg cgccgaacga cgacacgccc    4860
gcgcggcgcg gccggtcggt cggggccag  acggcggcgc cggtgacgag ttcgacggag    4920
ccggaggccc agtcgatgtg cggtgagggg cgtccacgt  gcagggtgcg gggcacttcg    4980
ccggcgcgca gcgcgagcac cgtcttgatc acgccggcca cgcccgccgc ggggccggtg    5040
tggccgatgt tggacttcag cgagcccagc cgcagcggct gtgcgcggtc ctggccgtag    5100
gtggccagca gggcgttggc ctcgatgggg tcgccgaggg tggtgccggt gccgtgtgcc    5160
tccacgacgt cgacgtcggc ggcggtgagg ccggcggcgg ccagcgcgga gcggatgacc    5220
cgctgctggg cggagccgtt gggggcggtg agcccggagg aggcgccgtc ctggttgatc    5280
gccgagccgc ggaccacggc cagcacgggg tggccgttgc ggcgggcgtc ggacagccgc    5340
tccagcacga ccacgcccgc gccctcggac cagccgatgc cgtccgcggc ggcggcgaac    5400
gccttgcagc ggccgtcggg ggcgaggccg cgctgccggg agaactccac gaaggcacgc    5460
ggggtcgaca tgaccatcac gccgccggcg agggccagca agcattcgcc gctgcgcagg    5520
gactggccgg ccaggtgcag ggcgacgagc gaggacgagc aggcggtgtc cacgctgacg    5580
gccgggcctt ccaggccgag ggtgtaggcc accggccgg  agagcacgct ggcgtagttc    5640
ccggtgccga gcagccctc  gtccacgccg gcgaccgcgc cgtgccgtga gtcgtagcgc    5700
tggtcggtga cgcccgcgaa gacgccggtg gcgctgccgc gcaggccgtg cggatcgacg    5760
ccggcgtgct cgaacgcctc ccaggcgact tcgaggaaca gccgctgctg cgggtccatc    5820
gccagcgcct cgcgcgggct gatgccgaag aagtcggcgt cgaagccggc ggcgtcgttc    5880
aggaagccgc cctggcgcag gtaggtgtgt ccggcccggt ccgggtcggg gtcgtagagg    5940
ccgtcgaggt cccagccgcg gtcggcgggg aagtcgccga tgacgtcacg gccttcggcg    6000
aggagctgcc acaggtcgtc gggcgaggcc actccgccgg ggaagcggca ggccatgccg    6060
accacgccca gcggctcgtc ggccggggtg gcgcggacgg cggggcgggc cgggacgggc    6120
gcgccgtcga gccgggtgag cagatggtcg gtgagggcgg ccgggttcgg gtggtcgaag    6180
acgacgctgc tggccagcgt caggccggtc gcctcggtca gcgcggtgcg cagccgcagg    6240
gaggcgaggg agtcgaagcc gagggcggcg aaaccgcggt gcggttcgat cgcggcgggg    6300
tcggcgtggc cgagcacggc ggcggtccgc agccgtacca ggtccatgac gcggtgccgg    6360
cgttcggcgg gggtcagccc ggccagctcg tcgcgccagg gcgtgccctc gtcggcggtc    6420
cgctgcgcgg ggagcgcgac gggggtggcg gccggggggca gcggcgggc cgctgcgtcc    6480 acgggcggcc agtaccggtc gcgctggaag gcgtacgtcg gcaggtcggc cggtgggct    6540 ccggtgcccc ggaagaaggc ggtccagtcg atgcgcacgc cgtgcgtgtg cgcctcggcc    6600
aggttggtca gcagggtcgg caggccgcc  cggtcgcgct ggagggtgcc gacgaccgcg    6660
gctccggtct ccgtgcgctc gacggtctcc tgggtgccga cggtcagtac ggggtgcgga    6720
```

```
ctgacctcga tgaagccccg gtggccctgg gcgagcaggg cggcgacggc gtcggcgtag      6780
cggacgggtt cgcgcaggtt gcggtaccag tagccggcgt ccagcgccgt gccgtccgcc      6840
cactcccccg tcacggtgga gaacagcgga accgtgccct cacccggccg cacgccctcc      6900
agatcagcca gcagagcctc acgcaccggc tccaccagca ccgaatgcga ggcatagtcg      6960
acagcgatac gccgggcccg cacccccga ccccgcaat gagccaggaa ctcctccagc      7020
gccaccccct cacccgcgac gacgaccgac tcaggaccgt tgaccgcagc caccgccaac      7080
cggcccgccc agcccaccaa cagctcctcg acaccggacg gccccggcagc gaccgacacc      7140 atcccccac tgcccgccag cgccgtcaaa gccctgctgc gcagggcgac gacccggggcg      7200 ccgtccgcca gcgacaacac acccgccaca caagcagccg cgatctcccc ctgcgaatga      7260
ccgaccacag ccgacggcac gacaccgtac gaacgccaca cctccgccaa cgacaccatc      7320
accgcccaca acaccggctg aacgacatcc acccgctcca acgccaccgg atcacccagc      7380
acaccacgca acgaccagcc cacgaacggc tccaacgcca ccgcacactc agccatccgc      7440
cccgcgaaca ccggcgacga atccagcaga tccaccgcca tccccaccca ctgcgccccc      7500
tgacccggga acacgaagac ggcgcggccg tcgccgacgg cgcggccgcg caccacgtcg      7560
gccgactcgg cgccttccgc cacggcggtc aggccggcga gcagggtgtc gtggtccgcg      7620
ccgaggacga ccacgcggtg ttcgaaggcc gtacgggtgg tggcgagggc gagggccacg      7680
tcgtgggggg cggcgtcgtg cgcgggccgg tgggcgagga ggcgttcggc ctgggcgcgc      7740
agtccggccg ccgtccggga ggacagcgtc cacgggacga ccggcagggt gcggtccgtg      7800
gcctcgtcgg tgggctcggg ccgggcgggt gcctgctcca ggatggcgtg ggcgttggtg      7860
ccggacacgc cgaacgacga cacgcccgcg cggcgcggct gctccccgcc cggccagtcc      7920
cgctcctcgg tgagcagttc cacggcgccg gcggtccagt cgacgtgcgg tgacgcctcg      7980
tccacgtgga gcgtgcgcgg cagcgtgccg tggcgcatgg cctgcaccat cttgatcaca      8040
ccggccacac cggcggcggc ctgcgtgtgc ccgatgttgg acttcaccga accgagccac      8100
agcggctcgt cccgctcctg gccgtaggtg gcgaggaggg cctgcgcctc gatcgggtcg      8160
cccagccggg tgcccgtacc gtgcgcctcc acggcgtcga cctggctcgc ggccaggcgg      8220
gcgtcggcca gcgcctggcg gatcacgcgc tgctgggcga gtccgttggg ggcggtgagt      8280
ccgctgctcg cgccgtcctg gttgatggcg gtgccgcgga ccacggccag cacggggtgg      8340
ccgttgcggc gggcgtccga gagccgttcc aggacgagca tgcccgcgcc ctcggcgaag      8400
ccgaacccgt cggccgccgc ggcgaacgcc ttgcagcggc cgtcggccgc gagggcccgc      8460
tgccggctgt actcggtgaa cacgccgggc gtggacagca cggtcgcccc gccggtgagc      8520
gccagcgtgc actccccggc gcgcagcgag cggaccgcga ggtgcagggc gaccagggac      8580
gaggagcagg cggtgtccac ggagagggcg gggccctcca ggccgagggt gtaggcgacc      8640
cggccggaga gcacgctggg cgaggtgccg gtgacgacgt accccctccag ctcggtggcc      8700 accgggccgg tgatgtcgga gtagtcctcg ctgctgaagc cgacgaacac gccggtggcg      8760
gtggagcgca ggccggccgg gtcgatgcca gcccgctcca gggcctccca tgaggtctcc      8820
agcaccagcc gctgctgcgg gtccatggcc agcgcctcgc gcgggctgat gccgaagaag      8880
ccggcgtcga agtccgcggc gccgtcgagg aatccgcctt cgcgggcgta ggaggttccg      8940
ggccggtcgg ggtccgggtc gtagaccgag gccatgtccc agccgcgtc ggcggggaac      9000 gccgagaccg cgtcggtccc atcggtcacc agccgccaca ggtcctcggg cgaggtcacg      9060
ccgccggggt agcggcaggc catgcccacg atcgcgatcg gttcgcggtc gcgggcctcg      9120
```

```
gcctcgcgca gccggcgccg ggcgacctgg agatcgcccg tgacctgctt gaggtagtcg   9180
agcagtttgg cctcgtcagc catcggtgca ccccgtgcg gttcgttcgg cgcgggtcac    9240
gagacgcccc ggtcgatcag gtcgaagagt tcgtcggcgg tgacgccgtc cagagcggcc   9300
cgctcgggtg tgccgtcggt cgtgccggcg tcccagcggg ccgcgaggtc ccgcaggtgc   9360
gccgccaccc gggcgcggtc ggtgccgtcg gccggcagtg cgccgagcgc gctctccacg   9420
cgggccagtt cggcgatgat ccggtcgcg ctcgcctcgc cggactcgct cggcaggagc    9480
gcgtcgagga ggtggtcggc gagcgcggcc gggttcgggt ggtcgaacac gatggtggtg   9540
ggcagtcgca ggccggtggc ggtgccgagg cggttgcgca gttccacggc ggtcagcgag   9600
tcgaagccca gttccttgaa gccgcggtcg ggtgccaccg cgtcgcgtcc ccggtgtccc   9660
aggacgtcgg cgacctggcc gcggacgacg tcgagcaggg cggggcgcg ctcgggcgcg    9720 ggcagcccgg tgatccgcgc caccagggcc gccgcaccgg gcaccgggcg ggcggcggcc   9780
gggccggccg gggtggcgac caggccgcgc agcagcggcg gggtgggcgc ggcggaggcg   9840
gtggcgaggt ccaggcgcgc ggtgacggtc acggcgtcgc cggtggcggt ggccgtgtcg   9900
aacagggcca gtccttcggc ggcggccatc ggcacgatgc ggttgcggcc ggcgcgggcg   9960
acgtcggcgg cgtccaggtg ccgggtgagg ccggtggcgt cggcccacag gccccaggcc  10020
gcggcggtgc cgggcaggcc ggcggcgcgg cgccgttcgg cgagcgcgtc gaggaaggcg  10080
ttggcggcgg cgtagttggc ctgcgcgggg gtgccgaggg tggccgccgc ggaggagaac  10140
agcacgaagg cggacaggtc cttgtcctcg gtgagttcgt gcaggtgcca ggcggcgtcg  10200
gccttcgggc gcagtacgcc cggcagccgg ccggcgccga gttcggtcag cacgccgtcg  10260
tcgagggcgc ccgcgtgtg caccaccgcg gtcagcgggg cctcggcggt cagcttggcg    10320
agcagcgcgt cgagggcggc gcggtcggtg acgtcgcagg tctcgaagcg gacggtggcg  10380
cccgccgcgg ccagttcggc gaccaggtcc gcgctgccgg gggcggcggc gccgcgccgg  10440
ctggccagca ccaggtcacg ggcgccgtgt tcggacacca gatgccgggc gagcatgccg  10500
ccgagcacgc cggcgccggt gatcaggacg gtgccgtcgg cgtacggggc gacggtgagc  10560
acgatcttgc cggtgtgccg ggcctgggcc atgaaccgga acgcggtgcg cgcgtcggcg  10620
aggggccagg tccgggtggg cagcccggtc agctcgcccg cctcggcgtg ggcgacgacc  10680
tcggtcagca ggctctggac gcggtcgggg ccggcgtcca gcagcaggtc gaacgggagg  10740
tagtcgacac cgggcaggcc ggcggggtcg cggcggtcgg tcttgccgag ttccacgaac  10800
cgtccgccgg gacggagcag tgcagcgac gcgtccacga actcacccgt gagggagttc    10860
agcacgacgt ccatctccgg gaaccgctgc gcgaactccg tatcccgcga cgacgccaca  10920
cgcgcctcgt ccagaccggc cgcccgcagc acctcgtgct tgccgggact cgccgtcgca  10980
tacacctcgg cgcccagcag ccgcgccacc cgcaccgcgg ccatgcccac accaccggcc  11040
gccgcgtgca ccagcacccg ctcccccgcc cgcaccccgg ccacatcgcg cagcgcgaac  11100
caggcggtgg cgaacacgga cggcagggcc gcggcgcgga cccaggacca gccggcggga  11160
acgggcacca cgagccgccg gtccaccacg gcgagggtgc cgaagccgcc cggcaccatg  11220
ccgaggactc ggtcgccgac ggcgaggtcg gtgacgtccg gggcgaccgc gaccacggtg  11280
cccgcggcct cggagccgat cgcgtcgacc tcgtccgggt acatgtcgag cgcgcacagc  11340
acgtcgcgga agttcaggcc cgccgcgcgg acggcgatgc ggacctggcc gggtgccagg  11400
ggggcggtgg cgtcgggagc ggcgacggcg tcgacgccgt cgatgctgcc gggccggacc  11460
```

```
acgtcgacgc gccaggcgtc ggcgccgacg ggcgggcgca gcgcggtctc agcggcccgg    11520
gtgagccggg cgacgaggcg ttcgccgtcg cggagcgcgg tctgcggctc gtcgccgacg    11580
gccggcacag cgtccaggga ggcgggtgtg ccgtcggtgt cgacgagcag gaaccggtcg    11640
gggtgctcgg tctgcgcgga gcgcaccagg ccccagaccg cggcggcggc cgggtcgggt    11700
tcctcgccgg gccgggcggc gacggcgtgc cgggtgacga tcgcgagccg ggcctgcccg    11760
aaccggtcgt cggcgagcca ctcgtgcagc agttccagca cctgggcggt ggcccggtgg    11820
gcggcggcga ccacatcggc tcctgtgctg acgggagcga ggacgaggtc caccgcgccg    11880
gcgtcgatgt cggcgagggc ggtgctcagg ggcgcggcga ggccttccgg tccgtcgccc    11940
aggacggcgc agcgcgcggc ggcgggtgtc tcggcgtcgg gggtctgcca ggtcacgcgg    12000
aacagcgcgt cgcgcgtgcc ggcggcggcc acggcgcgga gctgcccggc cgacgcgggc    12060
cgcagccgca gcgcggccag ctccacgacg ggccggccct cgccggtcggt cgcggtgagg    12120 ctcagcgtgt cggcgctctc ccgggcggcg cgcacccgca ggacccgggc cgggccgggg    12180
tgcacggtca cgccggtcca ggtgaacggc agcagcagcg cgcgtcctc gggctcggcg    12240 gcgggcacgg cctgggtgac ggcgtcgagc agcgccgggt gcacgagatg gccggcggtg    12300
tcgacggtgt cggggagttc gacctcgcg tagacctcgg tgtcccggcg ccacagggcg    12360
cgcaggccct ggaaggcggg cccgtagccg tagccgcggg cggcgaaacg gtcgtacacg    12420
ccgtccaccg ggaccggctc agcgcccgcc ggggccacg cgccggtctc gggctccgcc    12480
ggctcggccg gctcggccgg tgccaggacg cccgtggcgt gccgggtcca gccgtcgccg    12540
gagtgggagt ggacgcgac cgtgcggcgg ccggacccgt cggcgccgtg cacggtgacg    12600
cgcagggtca ggccgtcggc ggggacgccg atgggcgcgg ccagggtcag ctcctcgatc    12660
tgggcgcggt cgaccggtg gccggcgtgg gccaccatct ccaggacggc ggtgccgggc    12720
agcagggcgg tgcccagcac ggtgtgctcg gtcagccagg ggtgcgtctc ggggctgatc    12780
cggccggtga ggagcaggcc gtcctcgtcg gggagttcgg cctcggcggc gagcagcgga    12840
tgccctccgg cggtgaggcc gacggcggtc aggtcgccgg cggcggcctg ggggtgagc    12900 cagtagcgct cgcgctggaa ggggtaggcg ggcagttcga ccgggcgggc gccggtggcg    12960
tcgaacaggg ggcgccagtc gaccggcacg ccgtcggcgg ccacctcggc cagtgcggtg    13020
gtcaggcgca gccggtcgct ctcgtcgcgg cgcagggtgg cggcgacccg cagttcggtg    13080
cccgccgcct cggcggtctg ctgcatggcg accgtgagca cggggtgcgg gctgatctcc    13140
acgaagccgt ggtggccggc ggcgagcaga tcgctgatcg cgttctggaa gagcacgggc    13200
tcgcgcaggt tgcggtacca gtagcgggcg cccagttcgc tgccgtcgat ccagtcggcg    13260
gtgacggtgg agtagagggg cacgtcgccg tcccggggc ggatgccctt gaggtcggcg    13320
agcagccgct gccgtacggc ctccacctgc ggggagtgcg aggcgtagtc ggcggcgacg    13380
cggccggcgc gcagcccctc gtcgtcgcag aggtcgagca gctcctccag ggcatcgcgg    13440
tcgcccgcga cgaccagcga gcgggggctg ttggcagcgg cgatgccgag ccggccgggc    13500
cagcgctcca gcatccgctc gacgttcgcc gcggggcgg cgacgaaggc catgccgcag    13560
cggccgggca ggtcggcgac ggccttggcg cgcagcgcga cggtcttcgc ggcgtcgtcc    13620
agggtgaggg cgccggcgac gcaggcggcg gcgatctcgc cctgggagtg gccgaccacg    13680
gccgccggca cgacgccgtg ggagcggcca accgcggcca gcgagaccat gagcgcgaac    13740
agcaccggct gcaccacgtc gacgcggctg agcggcggcg cgtcctcggc tccgcgcagc    13800
acgtccacga ccgaccagtc caggtagggg gcgagggcgc gctcgcactc ggccatgcgc    13860
```

```
gcggcgaaca ccgggtgggt gtcgagcagt tccacgccca tgccgagcca ctgtccgccc    13920
tggccggcga agacgaagac gacgctgccg tcggctccgg cggtgccgcg gacgacggcc    13980
gggtcggcgc cgcccgcggc gagcacgtcg agcgcggcga gcagttcggc gcggtcccgg    14040
cccacgacgg cggcgcggtg ctcgaacgcg gtgcggcggg tggccagggt gaacccgacg    14100
gaggcgggct cgaggccggg gtcggcggcg acgaactcgc gcagccgggc ggcctgttcg    14160
agcagcgcgg cctcggtgcg cgcggacagc tgccagggca cggggagcgc accggccggc    14220
ggcgccgtcg cttcctcggg ttcgggcgcc tccgccacga tcacatgggc gttggtgccg    14280
ctgacgccga acgaggacac gccggcccgg cggggacgct cgccccgggg ccacgggcgg    14340
gcctcggtca gcagccgtac gtcgccggac acccagtcca cgtgcggggt gggctcgtcg    14400
acgtgcagcg tcttcgggag cagtccgtgc cggagcgcga gcaccgtctt gatcactccg    14460
ccgacgccgg cggcggcctg ggcgtggccg aggttggact tcagcgagcc cagccacagc    14520
ggccggtcgc ggtcctggcc gtaggaggag aggagtgcct gggcctcgat ggggtcgccc    14580
agggcggtgc cggtgccgtg gccctccacg gcgtccacgt cggcgggacg cagtccggcg    14640
tcggccagtg cctgccggac cacgcgctgc tgggcggcgc cgctcggcgc ggtgaggccg    14700
ttggaggcgc cgtcctggtt gacggcggtg ccgggcagca gggcgagcac cgggtggccg    14760
tttcgccggg cgtcggagag ccgctccagc aggagcatgc cgacgccctc ggaccagccg    14820
agtccgtcgg cggccttggc gtacgagcgg cagcgaccgt cctcggacag gccgccctgc    14880
ttggtgaagt cgacgaacag ctccggcgtc ggcatgacgg tcacaccgcc ggccagcgcg    14940
agggtgctct cgcccgagcg cagcgaccgc accgcctggt gcagggcgac gagggaggac    15000
gagcaggcgg tgtccaccgt gaaggcgggg ccttccaggc cgaggacgta ggagatgcgg    15060
ccggccacca cgctggccag gcggccggtc agggcgtgcc cgtcgccgcc ttccgggatg    15120
ccggcgagca gcgaggagta ggactgggcg ttggcgccga cgaacacgcc gacgcgtccg    15180
ccccgccacg agcgggtgc gacgccggcc cgctccagcg cctcccagct ggtctccagc    15240
agcagccgct gctgggggtc catcagctgg gcctcgcgcg ggctgatgcc gaagaagccg    15300
gcgtcgaaca gggcgacgtc gtcgaggaat ccgccgtgcc gggtgcggct ggccgagggg    15360
ccgtccgggt cggcgagggc ggcgaggtcc cagccgcggt cggcggggaa cggcgtgatg    15420
gcgtcgcgct cctccagcac gagccgccac agctcgtcgg gggtggtcac accgcccggg    15480
aagcggcagg ccatgccgac cacggcgacc gggtcgtcgt cggccgcgcg ctgtacgggc    15540
tcgtcgtcct cggcgagccg gacgtgccgg ccggaggcgg cgtcgaccag gacgtccgcc    15600
agggcgcggg cggtggggtg gtcgtagatg gcggtggtgg gcagcttcac gccggtgccg    15660
cggctgagcc gcagcagcag ttgtacgcg gtcagcgagc gcagtccgag ttcccggatc    15720
gcccggtccg gcggtacgtc ggcggcggtg ccgaggtcga gcacctccgc gacctgtgtc    15780
cggaccaggt ccaggacgac gcgccggcgc tcggttcgg gcagaccggc gagccggtgc    15840
gcgagcgcgg gcggctgagc agccttcggg tcggtcagcg gctcagtcat gggtggtccc    15900
ctccagcggg tccggtgcgt gcagtgcgga gacgggcagg ccgggttcgg cgagtgcggc    15960
ctgtagcagc gcggcggtgc cggccagcag gccgtccacg acgcgtcggc cgagggcggc    16020
ggcgcggtgt acgacgtgtc cggtgaggcc gccgtcgggg tcctcgacca ggtgcacctc    16080
gaggtgccag cggcgtacg cctgttggcc cgtgaactgc tcgacgcggg cgccaggcag    16140
gccgagttcg ccgagttcga cgttgacgag ctggaacacg acgtcgacca gcggctgttc    16200
```

```
ggggtccagg ccgaggcctt cgacgacgcg ttcccagggc agggcctggt gggcgtaggc    16260
gtcgagggcg gtgtcccgga cccgctccag caggccggcg aaggacgggt cgccgctgag    16320
gtcgacgcgc aggggcacga agttggcgaa gaagccgatc agcccctcga cctcggcccg    16380
ggtgcggccc gccaccgggg agccgacggc gaggtcgtcc gtgcccgccc agcgggcgag    16440
cgtggccgtg aacgcggcca gcagggtcat gtagagggtg gcgtcgtgct cggcgccgac    16500
ccggcgggcg gtggcgacca ggccggcggg cagccgccac tcggtcagca cgccggtggc    16560
gtcgtgggcc gcgtcggccg ggacgcccgg cagggcgagg ggccgcaggc cgtccagccg    16620
gcggcgccag tggccgagct gggcgtcgag cgcggctccg gtcagccagg accgctgcca    16680
gaaggcgaag tcgccgtact ggacgggcag ttcgggcagc tcggccggac ggttctctcg    16740
tagtgccgcg taggcgccgg acagttcggt ccagagcacg ccctgggacc agccgtcggt    16800
ggcgatgtgg tgcaccgtca gcagcaggac gtggtcgtcg ggggcgatcc gcagcagtgc    16860
gggccgcagc accggtcccc ggacgaggtc gaacggccgg ccgctgcct cgtcggccag    16920 ggcgcggggc gcggtctcgt cggccacgtc caccgggtcc agcacgatgt ccgtggcggg    16980
caggatcacc gacgccggct cgtcgccggg cacgaagacc gtgcgcagcg cctcgtgccg    17040
gcgcacgacc tcggtcaggg cgcggcccag caggtccgcg tccagttcgc cggtgatccg    17100
cacggccagc gggatcgtcc agaccgggtc gccggggtcg gcctcgtgca gccgccacag    17160
ccgcagctgg cccagcgaca gcggcagggg ctcctgccgg acaccggca ccaggggcgg    17220 tacggccgtg cgcggggcca cggcgacgac ctcggcgagg gcgcgcgggg tgcggtgctg    17280
gaacagctcc cgcagggaca cctcggcgcc cagcgcctcg cggatccggg cgaccgtgcg    17340
ggccgcgacc agcgagtgcc cgccgagcgc gaagaagtcg tcgtcgatgc cgaccccgcc    17400
ggtctccagc acctcggcga acacctcgca cagcgtctgc tccgcaccgg tacgggtgc    17460 ggtgaagccg gtgtcgagcg tggtgcgcag gtccggggcg ggcagcgcgg cccggtcgat    17520
cttgccggtg gtggtcagcg ggaacgcgtc cagcgcgacg agcgccgacg gcaccatgta    17580
gtccggtacg gcgtcggcca ggtgggcgcg cagccgggcc ggcagccctc cgtcggtacc    17640
ggggacgggc acgacgtagc cgacgagccg cttgacgccg ggggcgtcct cgcgggcgac    17700
gatgacggcg cgggtgacct cggggtggcg cagcaggacg gcctcgacct cgcccagctc    17760 caccccggaag ccccggatct tgacctggtg gtcgagccgg cccaggtatt ccaggctgcc    17820
gtcgggccgc cagcggccca ggtccccggt gcggtagagg cgggagccgg gcgggccgaa    17880
cgggtcgggc acgaacttct gcgccgtcag ttccggcttg ccgacgtagc cgcgggcgag    17940
tccggggccg gcgaagcaga gttcgccggc cacgcccacg gggaccggcc gcagccggtc    18000
gtccaggacg taggcgcggg agttgtcgac cggctcgccc aggtgtgcgg tccggggcca    18060
gtcggcgacg tcagcgggca gggtgaagga ggtgacgacc tggatctcgg tggagccgta    18120
gtggttgtgc agacgcagac ggggccgggc ggcgcagaac tcgcgcagca cggtgtccag    18180
cgacagcggc tcgcccgcct gggagatgtg ccgcagcgag gtgagccggg cccggccggc    18240
gccggcctcc tcggcgagcg cgcggatcat caggttgggc acgaatatct gctcgacggc    18300
ccgttcgtcg agccagcggg cgaagcgggc cgggtcgcgg cgggtctcct cggtggggat    18360
gaccagcgtc tcgccgtaca ggagcgcgga gagcacctcc tgcacatgca cgtcgaaggt    18420
gagggcggtg aactgggcgg tgcgcgtgcc gggtccgccc ggtaccgtct tcttctgcca    18480
ggcgagcatg ttgaccacac accgggcggg catggcgatg cccttgggca cgccggtgga    18540
gccggaggtg tagacgacgt aggcgaggga gtcggggccg ggtcgtccgg cggccgttgc    18600
```

-continued

```
cgcgggcggc tcctgcccgg ccggggcgtc cacgaggacg agggcggtgc cctcggcgaa   18660
gacgtccgcg tgagcccggt cggtgacggc gacggtcatc cgggcgtcgt cgacgatgag   18720
ccggatccgg tcccgggggt ggctcgggtc gatcggcaca taggcggcgc cggccttgag   18780
gatgccgatc agagcggcca tctgcacggt gccgcgctcc aggcagaggc cgacgaggtc   18840
gtccggcccc acgccctggg cccgcagccc ggcggcgatc cgctcggcct cgtggtccag   18900
cgcggcgtag gtgaggacgt cgtcctcgca ctccacggcg cgggcgccgg gggtgcgggc   18960
gacctgctcg gcgaacagct ccacgagcgg gacgtccgg tacgggaggg cggtgtcgtt    19020
ccaccgctcc agcagcaggc gccggtcgtc gtcgtccagc agcgagagcg cggacagcgg   19080
cgcgtccggg tcggcgaggg cggcgcgcag cagcaccgtg tggtgatgca gcaggcggcg   19140
gaccgtgtcc gcctcgaaca gcgcggtgga gtgcagcacg gtgccgcgca cccggtcgcc   19200
gtcctcggtg aggtgcactt cgaggtcgac gcgggtgaag gcgtgctcgt ccagcagcgg   19260
ttccaggcgg gcgcgccga ggcggtcgcc cttgtcccg ggcgcccgca tcagctggaa     19320
gaccacctgg accagcgggt tgcgggacag gtccgctcg ggtgccaggg tctccaccag    19380
gtgctcgaag ggcaggtcct ggtggtccat ggcgcccacc accgtctcgc gcacccggcc   19440
cagcaggtcg cggaaggtcg ggtcgccgga gacgtcggtg cgcagcacca gcatgttgac   19500
gaagaagccg atcagccgct ccacctcggg gcgggtacgg cctgccacgg gggcgccgac   19560
ggcgacgtcc tcggtgccgg cgaaccgtgc caggaccacg gtgaaggcgg tcagcagcgt   19620
catgtagagg gtggcgccct cggtgtcgcc gaacgcgcgc gcggcccgga ccaggtcctc   19680
gggcagttcc cacggctggg aggcgcccgc cgagccggcg accgcgggc ggggccggtc    19740
caggggaagt tccaggggc gcagcccggc gagccgcgcc cgccagtagg tgaggtaccg    19800
ctccagttcg gcgccggtga gccggccctg ctgccagacg gcgaagtcgc cgtactggac   19860
aggcagttcg ggcagttcgg cggggtcgcc ggacagttcg gcgcggtagg cctcggccag   19920
ctcgccccag aacacggcgt gcgaccagcc gtccgtgacc gcgtggtgcg cggtgatcag   19980
gacggcgtgg tcctcggccg cgaggcgcag cacgcgggcg cgcagcagcg gtccccgggc   20040
caggtcgaag gggcgcgcgg cgtccgcctc ggccaggggc cgtacctcgg cctcgtcggc   20100
gacgtccgtg acctccaggc ggagcggggt cgcgggccgt acgacggcca taggctcgcc   20160
ggcgtcggcg gcgaagacgg tgcgcagcgc ctcgtggcgg gagaccacca gggacagtgc   20220
ccggccgagg gcgtcgacgt cgagcgggcc gtgggcgcgt acgcccatcg ccacgttcca   20280
gaagccgctg tccggggtga gccggtccag gaaccacagg cgccgctggg aggacgacag   20340
cggaagcgcg gcgccgtccc ggcgggccgg ccggatgacg tccgtggccg tgccgggctc   20400
gccgagggtc tcggccagcc ggcgcgggga gcgccgttcg aacaccgcct ggagcggcac   20460
gtcgggcccg aagcgggcgc ggatccgggc gatggcgcgg gtggccagca gcgagtgccc   20520
gcccagggcg aagaagtcgt cgtcggcgcc caccgggtgg acgtccagca cctcggcgaa   20580
gatctcgcac agcacccgct ccgcctcggt cgcgggcggg acgtaccgc tctcggcgac    20640
cgagcgggtg tcgggcgcgg gcagggcccg gcggtcgatc ttgccggtgg tggacagcgg   20700
gaacgcgtcg agcgcgacga acgccgacgg caccatgtag tcgggtacgg agcccgcggc   20760
gtgggcgcgc agggcgggca gcacgctcgc gccggcctcc ggctccagca ccacataggc   20820
gaccaggcgc ttgtcgcccg ggatgtcctc gcgcacggcg acggtgacct gcgagaccgc   20880
cgggtgccgc agcagcgcgg cctcgacctc gccgggctcc acccggaagc cgcggatctt   20940
```

```
gacctggacg tcggcgcggc cgaggaactc cagcgcgccg ccgggcagcc accgtacgac    21000
gtcgcccgta cggtacatcc gctcgcccgg cccgccccac gggtccggca cgaacttctc    21060
ggcggtcagg tcgggccggc ccaggtagcc gcgcgccacc cggggcccgc cgatgaccag    21120
ttcgcccgcc acgcccagcg cgcgcggcg gagggtgtcg tcgaggacgt acacccgggt      21180
gttgtcgatc ggcgcgccga tgggcacccg ggagccggcg agccggaagc cgggttccat    21240
cgggaacagc gtggtgaacg cggtcgcctc ggtcgggccg taggcgtcgg ccacggtcag    21300
gtgcgggtgg gcggccatca cctgggcgac ggtctcgccg gacacggcct cgccgccggt    21360
gagcacctcg cgcagcccgc cgaagcactc catgcactcc tcggccagga ggctgaacag    21420
gggtgcgggc aggcacatcg cggtgacgcc gtgctcgcgg atgagccggt cgaaggtgtg    21480
cggttcgacg tgctcgtcgg tggcgacgac gatctgcttg ccggtcagca ggaacggcca    21540
cagctcgtag gtggagatgt cggtggccag cggatagtgc agcagcaccc gttcgtggtt    21600
gccgttgctc cagcggcggt cggcggccag cacgacgacg ttgcggtggg tcacggccac    21660
gcccttgggc tcgccgctgg acccggaggt gtagatgacg tacgccgtgg tgtcggggtg    21720
cgggtcgata ccggggtcgg tgtcgggccc ggggcccggg tcggtgacgt cgaggacggt    21780
gatgccgtcg gtgccgggca ccgggcggtc ggcgatgacg acgcgcagcc cgaggtggc     21840 cacgatgcgc tcggtgcggc ccggggggtt gcgcgggtcg agcggcacgt aggcggcgcc    21900
cgccttgagc acgccgagca cggcggccac catgccggtg gagcgtccgg tggcgacgcc    21960
gaccggttcg tcggcgccga cgccgtgggc cagcaggagg tgggcgaagc ggttggcccg    22020
ccggtccagt tcgcgctagg tgacccgctc gtcgccgcag atcagggcga cggcgtcggg    22080
ggtgcgggcg gcctgctcgg cgtagagccg gggcacgcag ccgtccggca gcggtgcggc    22140
cgtgtcgttc caggcgacca gggtgcggtg ccggtcggtc tcgtcgagca tggtcgccgc    22200
ggagaccggc cggtcggggt cggcgagcac ctcgccgagg accaccgaca cgtggtgcat    22260
cagctggcga acggtgtcgg cgtcgaacag gtcggccgcg tacaggacgg tcgcgccgac    22320
ctcgtcgccg gtctcgacgg cgtgcacctc caggtccatc cgggtgtacg cgtggtcgat    22380
gtcgaacggc tcgcccgggc gccctgcca ccagggccgc cggggcgcgt cggcgagcag     22440
ctggaacgcc acctgcacga gcgggttgcg ggacaggtcg cgctcggggc gcagccgttc    22500
caccaggtgc tcgaagggga cgtcctggtg ctcgacggcg ccgaccaccg actcccgtac    22560
ccggcccagg agttcccgga aggtcgggtc gccggacagg tcggtgcgga cggcgacgac    22620
gttgacgaag aagccgatca gcgcctcggt ctcggcgcgg gtccggccgg ccgtcggcga    22680
gcccacggcg atgtcctcgg tgcgggcgta ccggacagg acgagggtga acgcggccag     22740
gagcaccatg tagagcgtgg ctccctcgcg ggcggcgacg gcccgggcgt cccggatcag    22800
ctcggcgggc agctgccagg gcagggtgcc cgcccgcccg gtggcgacgg cgggccgggc    22860
cttgtccagc ggcagttcca gcggggcgag gccggccagc cggccggtcc agtagccggc    22920
ccggcgctcc agcacctcgc cggtcagcca ggaccgctgc catacggcgt ggtcgccgta    22980
ctggacgggc agttcgggca gcggggcgcc gtcgtacgcg gcgcgatct cggcccacag      23040 cagggcctgg gaccagccgt cggtcgcgat gtggtgcacg gcgacgacga ggacgtggtc    23100 gtcggggcg agccggagca gcgtggcgcg cagcagcggg cccgcgtca ggtcgaaccc       23160 ggtggacagc tcggcggagg ccggccgcgc tgccgcgtcg gcgtcgggta cgtcgacgat    23220
ccgcggggcg accggggcgg cggcgccgat gaccgcggcg ggcacgccgt cggcgaccgt    23280
gaaggtggtg cgcagggtct cgtgccgggc gacgaccgcc gacagggcgc cggccagccg    23340
```

```
ctcggggtcc agcggtccgc gcacgcgcag ggctccgccg gaggtgtacg aggcgctgcc    23400
gggggcgagc tggtccagga accacatccg ctgctgggcg aaggacagcg gcagcagccg    23460
gtcgcggtcc gcgggcacca gcggcggcgc cgggtcggcc gggagcgcgg cgccggcgac    23520
caccgaggcc agggctcgcg gggtgcggtg ctcgaacacc tcgcgcagcg ggacctcggt    23580
gccgaaggcg cgggcgattc gggcgacgag gcgggtggcg agcagcgagt ggccgccgcg    23640
tacgaagaag tcgtcctcgg cgccgaacgc gtcggcgtcg agcagctcgg cgaagatctc    23700
gcacagcgcc cgctcggcgt cggtgcgcgg ggcggccagg ccggcgtccg ccgtctccgc    23760
cggggcgggc agcgcggcgc ggtcgacctt gccggtggcg gtcagcggca gcgcgtcggc    23820
gaggacgaag gccgagggca ccaggtagtc gggcagggcc gccgcggcgt gggcgcgcag    23880
ggcggcggtg tcggtggtgc ggccggccgc gggacgacga tgggcgacga gccgcttgcc    23940
ggccgggccg tcaccgcgca ccacgacggc ggcgtgcgcg acggcggggt gggcggccag    24000 gacgcctcg acctcgccgg gctcgacccg gaggccgcgc agcttcgcct ggtcgtcggc    24060
gcggccgagg aactccagga cgccgtcggg gcggcggcgc accacgtcgc cggtgcggta    24120
catgcggctg cccgccggtc cggacgggtc gggcaggaag cgctcggcgg tggccgccgg    24180
ccggccggcg tagccgcggg ccaggcgcgg gccgccgacg tacagttcgc cgggcacgcc    24240
gaacgggacg ggccgcagcc ggtcgtcgag gacgtgggcg cgggtgttgt ccaggggggct    24300 gccgatgggc accggccgc cggggccgg gtcggccggc gcgatcggt ggagggtggc    24360 gaaggtggtg gtctcggtgg ggccgtagcc gttgacgacc gtcaggtccg ggtgggcgcc    24420
gcgcacgcgg gccacggtcg ccggggacac ggtgtcgccg ccgacgacga gttcgcggac    24480
gccggccagg caggtgacgt cctcctcgac cacgaggtcg aagaggccgg aggtcagcca    24540
cagcgcggtg acgccctggt cggcgacgac acgggcgagg gcggcgggtc cgagggcgcc    24600
gggcggggcc accacgacgc ggcggccgga cagcagcggg gaccacagtt cgtaggtgga    24660
ggcgtcgaac gcctgcgggg agtgcagcag gacccgttcg tgggcgccgc cggaccagcg    24720
ccggtggagg gcgagggcgg ccacggcgcg gtgggtcgtg gcgacggcct tgggcgtgcc    24780
ggtggaaccg gaggtggaca tcacgtacgc gaggccgtcc gggccgacgg tgttcggcaa    24840
agccgtgtcg ggggctgtgc cggggacggc gcgcaggtct acggccggca ggtgctcggt    24900
gccggcgggt gcgggaccgc cgtcggtcag cagcagcgcg gcaccggtgt cggcgaggac    24960
ggcgcgggtc cggcggccg ggttgcgggc gtcgagcggc aggtaggcgc cgccggcctt    25020
gaggaccgcg agcacggcga cgaccaggtg ggcggaacgt tccgtcgcca gcgcgacgac    25080
gctctcgggt ccggctccgt ggccggccag gacatgggcg agccggttgg cggcgcggtc    25140
cagctgggcg taggtgaggt gttccgtccc gtcggccacg gcgacggcgt ccggggtgcg    25200
ggcggcctgg gcggcgaaca gctcgggcag cgaggcctcg ggcagcggta cgccggtgcc    25260
ccgggcggcc cggtccaggg ccgcgtcctc gcccgcgtcg gtcatcgtca gccgggacag    25320
cggccggtcg ggctcggcgc aggcggcgcg cagcagggcc gtcaggtggc gggccagccg    25380
ctcgacggtc tcccggtcga acagggcgcg gctgtagttg atcagtccct cgacgccgcc    25440
ctcggcgtcc tcgccgaggt agacctccag gtccatgcgg gtgaaggcgc ggtcgcccgc    25500
gaagggttcg gcggtggtgc cggggaacgg cgcggggcgc gcggcgggcc ggggcacgta    25560
ctggaagacg acctgggcga gcggggttgcg ggacaggtcg cgctcgggga ccagccgctc    25620
caccaggtac tcgaacggca cgtcctggtg cgccatctcg tccaccgagg cggcgcggac    25680
```

```
gcgttcgacg agttccgcga aggtggggtc gccgccgagg tcggtgcggg tgacgacggt    25740
gttgacgaag aatccgatga gttgctcgac ctcggccagg ggccggccgg cgaccggctg    25800
ggcgacggcg acgtcctcgg tgcgggcgtg ccgcccgagg accgcgctga acgcggccag    25860
cagggtcatg tgcagggtcg cgccctgccg tgcggcgacg gcccgggcgg cggcgacggc    25920
gtccgccggc agccgccagg tgacgacgcc gccctcggcg gaggcgacgg ccgggcgggg    25980
ccggtcgagc ggcaggtcca gcgggggcag gccggccagc cggtcctgcc agtacgccag    26040
ccgccgctcc agcacggcgg gcgacagggt acggcgctgc caggcggcga agtcggcgta    26100
ctgcaccggc agttccggca gcgcgggctg ccggccgtcg gccagggcgg tgtaggccgc    26160
ggtcagctcg gcccacagca ggccgtgcga ccagccgtcg gtggcgatgt gatgcaccgt    26220
cagcagcagg acgtggtcgt cgtcggcgag ccgcagcagg cgggcgcgga gcaggggggcc    26280 cttggtgagg tcgaaggggc gcgcggcctc ctcgccggcc agccgctcgg cgtcggcctc    26340
gtccacggcg tcggtcacgg gaacgggcac cggctccggc ggcaggacga cggcgccggc    26400
cacgccctcg tggtcggcga agacggtgcg cagggtctcg tgccgggcga cgacacagct    26460
cagcgcccgg gccagcaggc cggcgccgag cgggccgcgg acgcgcacgg cggtgccgaa    26520
gttgtagaag gcgctgtccg gcatcagccg gtcgaggaac cacagccgct gctgggcgaa    26580
cgacagctcc agcggccggt cgcggggggac ccggctgatg cccgcgggtg tcgtgccggt    26640
cctcgccgtg cgctcccgga gccggttgag tgccgagtcc agtcccggcc gtcgcgagct    26700
cccctgcgtc atccggctgt ctcccgctcc tcgtcggctt cggtgagtcc gcggtcgcgc    26760
atcacgctgg ccaggggcgcg gtgggtgccg gactcgcttg cttcgaactg ctcgaccacg    26820
cgccgccgca tcggggcggg cttctcctgg ctgagcttga acatcgtctg cacggaatcg    26880
acccgcaggg tgaaggcgcc cacgccgggc gcgatctggc ggaagtagtc gagggaggac    26940
tcctggtccc agccgcgccc gaagccggac tccagccgcc gggcggtgtc ggagacgatg    27000
tccagcacgg cggcggggtc ggcggtgggc tccactgtgc cgttcacgtg gacggcgatg    27060
aagtcccagg tgggggccgc gggcgtgacc ccgtagaccg tcggcgagac atagccgtgc    27120
gggccctgga agacgatgag cgcccggtcg ccggagcgca tccggcgcca ctgcgggttc    27180
tcgacgttca tgtggccgat cagggtggag ccggcgagcg ggacggtgcc cgcggcgacg    27240
gcctcggcgt cggcgccgtc gggtccgtgc cggaacagca ccggcgcgtg ggtggccacc    27300
gggacgtcgt cgtgcgaggt gacgaccatt gccagtgggt tgtgtcgcag aaacgccagg    27360
acgacgccgt cgcaatcctc ccggtacagc ggacgttcgt acacttcagc ccctgttccc    27420
cgctgctgcc ttgcttccgg tggagcggtc cgggtcgcac cggccgccgg tgatcgaccg    27480
ggcgatctcg cccgcgcgga ccgccaccat ggacagcagg gtggaggcga tgccgtgggt    27540
cgcctcggtg gcgccctgga cgtagatgcc gcaccggaaa tccccggtgg tgccgagccg    27600
gtagtcgcgg ccgatcagca actcccccgc ctcgtcccgg cggagggcgc cggagacgcc    27660
gccgagcagt tcggccgggt cggtggagtc gtacccggtg gcgtacacga ccaggtcggc    27720
gtccaggtcg gtgtgttcgc ccgtgggcag gaactccacg cgtacggcgg cggattcctg    27780
gcgcggttcg acggacacca ggcgggaggc gttcatcacc cgcagccgcg gggcgccgga    27840
caccttctgc tcgtactggc ggcggtagag gccctggagg acgtcctcgt cgacgacggc    27900
gtagttggtg ccgccgtggt agcgcatgat ggcctgcttg acctcgggcg gggcgaagta    27960
gaagtcgtcc acgcggccg ggtcgaagac gcggttggcg aacggggctgg agtcggcgac    28020 gctgtagccg tagcgggcga acaccgcgca cacctcggcc tgcgggtagc ggtccatgag    28080
```

```
gtgcgcggcg acctcggccg cgctctggcc ggcgccgacc acgacggccc ggcggggcgg    28140
gcgttcgtcg aacgcgggca gccggtgcag caactgggag ctgtgccaga cgcgttcgcc    28200
ggtctccgcg ccctcgggca gccggggggcg caggccggag gcgaggacga ggtttctggt    28260
ccgggcgacc acccggtccc cggcgagcac gtcgagcgcg acgacctcac cggcttcggt    28320
caccggccgc acaccggtgg cctccacgcc gtactcgacc aggtggttca gccggtcggc    28380
ggcccactgg aggtagtcgt ggtactcgat ccgggagggc agcagggtgt gctggttgat    28440
gaagtcgacc agccggtcct tctcctggag ataggacagg aatccgaaat cactggtggg    28500
attgcgcatc gtggcgatgt ccttgagaaa ggacacctgg agcgaggagc ccccaggag    28560 catcccccga tgccagccga attccttctg cttctccagg aaaagggcct tccggcggc    28620 ttcggattca tggagcgcca ccgcagggc gagattcgcg gcaccgaatc cgattccggt    28680
gacgtccagt acttctgatt ccgggctctg ctgcgcagtg gatgattgct ctgcgagccg    28740
ggtcatatat caaccgccat tagtttttca atggatgtat cgtcgcagga cgcccagaat    28800
tcacctgcga cgtcctccag atgcgtgagg aacgcgcgc tgtaaaaggt ggtctggtac    28860
tgggttatgt cgtagtcgac gtgggccatg tcggcgatgt ccagcggccg gatctccgcg    28920
gaacggaagt gctccagctc gccgtaggag gagacgacgc tggcgccgta ggcccggggc    28980
ccgtcggcgg cgtccagcag gccgcattcg agcgtgaacc agaaggtctt ggcgacgaac    29040
tggacggcgt cctcggactc caccctgcgc acggcctcgc cggccaggcg gtacaggttg    29100
gcgaaccggt cgtcggccag ggcgctgccg tgcccgatga cctcgtgcag gatgtccggt    29160
tccgtcgagt agaagggtgt cgcgctgtcg cggaggtact gggtggagtg gaagtacccg    29220
tcggccagag agccgcagaa cagggcgaag ggaaccacgc cggacgcggg gcgtaggcgg    29280
aatccggtca gctggtcgag ccggtcggac acttcacgca actgcgggac gccgtcgccg    29340
cccacctcga gccgctccgc cgcctcgacg aactccggcg ccgccatgtg ccggtgccgg    29400
tccgcgagcc gcttggaaac caggcgccac agagcgtgct cggcgtccgt gtactcgacc    29460
tctggaatgg gctcgccggg cacataggcg gcagcgcttg cggcgatttg gtcacgccgc    29520
tgctgataca ccgacgacgc ggttaattcg ggcgcgcccg agccgatttc cacgaacttc    29580
cccctacttc catcgacaga aggcagcagt tgctgtccga agctatttttg gttcggacgc    29640 ccgcatcaac cttcccttgt ccagccgatt cattaggacc ctacaagcca cccgcagcac    29700
tcgcaagagt tttctatgcg cccgctatgt accctttttgg gcagactcac cggaaattat    29760
cgtcatccgc accgccggaa ccggagtcaa gcgttggctc ggcagggcgg cttcaagttc    29820
ccgataggag cgggccctag gcgattcctc agatccggcc ggcgcgttcg ggtgtgtccc    29880
aaatcactgg cctaaatcct tcatgaggac ccgtcagctt gccgacggac gctctttcgc    29940
ttgtggtgcc gggcgtttcg gtgtccgggc aggccgcgcg ggagcgcccc aactgccgcg    30000
tcgggctgtc gcgtcgggtg ggcgccgggt tccacggctc cggagtcct tcgacagggc    30060 ccggcgaata tctccaggac caagccgtgg gcggtgaggt ggtcggcgag ggcggtgagt    30120
tcggcggcgt tgcgaccgag ccgcttccgc tcgtacaccg tgaagatgac acggcagtgt    30180
ggggcgtgcg ccttgacctc ccgcgccgcc ctcagcgcct cctcccggaa cttcgggctg    30240
ccccgcgccc gggtgctgat cttctcgccg aagatgtagt cgcgcgagat gccgtgtttg    30300
gcgagcgcgt cgagctggga gtcacttcgc ctgcatccgc ccgcgcgcgg agtggtgcgg    30360
catcgtggca gcgcgcgtca gatgcgcggc gtcgccccca ggtgaactcc gtccgccctg    30420
```

```
gggcagggtg ggcggagttc accgcgtcgt gcggttcaac gggtccaatg gaggtcgcga   30480
tacggtccgc ccggcgcgcg ggccgcgatc atcattccgg cggggcggag ccgtcagtgc   30540
ttgacggtga acgtggcgcc ttggggcgcg aaggtcgtgt cgtggtcctt ggcggtggcc   30600
agcacggata cgtgccagac gcccttgggc aacgcggcgg cttccttggc cgagctcttc   30660
acggtgtagg tgcacaccga ggccgtcgcg gaagtcgcct tgcacgtggc ttcctcgaca   30720
tcccgcatct cgcccgccgt gggcgcaagg cccgaactcg ccggccaggc gagcacccgc   30780
aggctcttga ttccggagtt gtcggccacg gtggcgctga aggtgagcga ggcgctccca   30840
ccggccgtac tggtgtagtg ggcggtggcc tttgagatct ccggcttggc cggcacagcg   30900
gcgtcggccg aggagacgaa caccacggtg ccggcaacga cggctgcggc cacggcgagc   30960
gacgagacga caaggcgctt ggacatgaag tatcccctca tagatgaccg ctactggtct   31020
cttcgccgag cgctctgcgc accgcggcgt tgtgtacaca gcctgtctcg acggccctgc   31080
ccctcacatg ggcagaacta ctcaaccgaa gtactcagac gccctgagct tgtcgttcaa   31140
cctcgtctcc gttggggcg ggtattgagc aggcgctttt cgaatgtggc gtccagcacc   31200
gccgtccagg atgtgcagcc ggtctgcaag cttcgtcgcg atcaggacct tcagcagatc   31260
cagcgcgtcg tccaccgccc gcgacgtgag gtacaccgcc gcggccagca gcgttgtgag   31320
gctgcgagag tccgagtgcc ggcgcggcaa cgacaccttg tcgtccgccc cgtaccgcga   31380
ccactctgcg ccgccccgtc acccgtaccg gtccgcggcg cagccggtcc agctccacca   31440
ggcggcccga cgagcagaga atccagcacc gcccgctgca cgacgcgcgg catcccgcac   31500
aaggcgtccc aaaacgccga ttcgccgcct cccacaccga tcccacagga caggccgac    31560 agctcgcccc cagcagcagc ggctactgtc accegttcgg cggcgggcgc gacagagccc   31620
gtgacaacca gattgtgacg ttcggtgatc gtgacaccaa ttcggagctg gcccgctgac   31680
ctgtgacagc ggactggcct cgaaggtgga ccgaatgcag ttcttgacag caaagacgga   31740
ccgccgcagc tcaggggcgc agtgcccgcc cgcagcacag tcggttcagg gctcgacgcc   31800
ggctacggac agacgtggat cgccggtcgc ggtcagcgcg aacgctgtcc ggtgaagagg   31860
cggtacagca ggagcacgat caccgagccg acgaccgcgg cgatccatgt cgagaggtgg   31920
aagaagccgt tgatggagtg cacgccgaag atcaccttgc cgagccagcc gccgagcaga   31980
ccgccgacga tgccgatgag catcgtgacg aggcagccgc ccgggtcctt gccgggcatg   32040
agtgccttgg cgatggcgcc cgcgatgagg ccgatgagaa tccaggcgat gatgcccacg   32100
gtgtgcgtcc tttgctgtag gtggtgccga ggaaggcccg acgaggctcc gccggggctg   32160
cccgccggtc gctccgcgcg gacgaccggc gacatacgga tatccgctcc ggaacactcc   32220
acacgggtca aaggtcccgt ttcctccgac cgacccaccc ggcatccgat ccgtcggccg   32280
atccggtcga cggcggattc ggtgactggt caaccttcga tggcgctcga tcaaggttcg   32340
ctgtcacagg tcatccgccc tcagtccctc aggtcgcccc tcggaaggcg tccaccagag   32400
gtcaggcggg tccattcctc cggatcccca gctgcctcac agggtgctgg ggacccgggg   32460
acggccctcg gtgttatgga taagccgaag ctcaggacgt tctcacggcg acgccggatg   32520
agctggcgag gagggcgtgc cgaggcagtt cggttgtcac cgaggaggca tcccacttct   32580
cacgcgtgct cattcggcgg acttcctgtc accggcgccg acgagccgga gttcccgggc   32640
tccccggctg ggcccggctg agggctgagc ccttccacgg cgaggcgaa gaggcggtcg    32700 gcctgggtgt cggggtctgt gtggtgctcg gtggccaggg cgatgccgac ggcgaggtc    32760 agcaggtcgt gaaaggtgac gtgcggtgca accgccttgt cgcggatggc ccgctggagc   32820
```

```
aagggagttg cggctgcttc gattacgccc ccgcagctct tcggggaggg ttcttcggtg   32880
ggcggctcgt agctgaggat atgggcgaat ccgcgggctg agacggcgta gcggacgaag   32940
gcgtggaacc actccagcag tgcggtgcgg ccgtcctcgg acgcactcag ccgatgggcg   33000
cgctcgcaca ggcccgcaat gcgctcctgg aagacggctt cgaggagcgc ccggcgggtg   33060
gggaagtgac ggcgcacggt cgccgaaccg acgcctgcga tgcgggcgat ctgctcctgg   33120
gatgcctcgg cgccgtgcgc ggcgacttcg gcttcggcga cggcgaggat gcgctgatag   33180
ttgcgtcggg cgtccgagcg ctggccagtc atggtctcct cgttgctaag tggcgggccc   33240
cgccatatct tagcggcaca cgaaacggcg ggccccgccg ttttgtctct ccggcccttg   33300
aggagcagca ccatgcccag cagcagcgat accgtcctgg tcaccggcgc caccggccag   33360
caaggcgggg ccacggctcg cgcgcttttg gccgccaagg tgcccgtacg tgcgctcgta   33420
cgcgatccct cgtcgaagtc cgcccgggcg atcgaggcgc tgggcgcgga actggtacgc   33480
gcggatcttt ccgaccgggc ctccctcgac ccggcggtcg agggggtccg cgcggtgttc   33540
tcggtgcaga tgccgcccat gaccgagacc agcgtggact tcgcgagcga actcgcccag   33600
gccaccaacc tggtggacgc ggcgaagata ggggagtac ggcagttcgt acagtcctcg   33660
accagtggag tcggtgaaca cacccgggtc gccggctggg ccgagggccg ctgggcggcg   33720
atggcggagt acttccacac caagcaggcg atcatggagg cggtgcgtgg tgcgggtttc   33780
gcccgctgga cggtgatcaa gcccgccttc ttcatggaga acctgcccct gctggcaccc   33840
aaggggcccc gcggcggact gctgacggta ctgaagccgg acaccgaact ggccttggtg   33900
gccgtgcggg acatcggcac ggccgcggca cacgccctcc gagacccga ccggttccac   33960 caggtggaac tggaactggc tggtgaccct cgcacgatgg agcagatcgc gcagaccttg   34020
tccgccgcct ggggcgtgcc cgtgaccgcg ccctccctga gcgtggaaga ggcccttgcc   34080
gcgggcatgc cgaagtgggg agccggacac gagtggaaca acgtggtcct ccagcccgcc   34140
cggcccacat tcgcccggaa gttgggcatc ccgctcacca ccttcgccga gtgggcggat   34200
gagcagttga cacatgtgtc tgattagggg tgtggcggca agggcgcgcc attgaccct   34260 acggggagcg cggcggttgc ccgcagaggg cattgcggtc gggggggcatc ggtgccggtc   34320 ccctggacgg gctgcaatga gcaggacagc gcagagggt ggacacgaga tccctggagt   34380
gcacgacgtg gccatcaggg ggtcgggcgg tacgggatgg ggatgatgta gcgcgggtgt   34440
ggaggcatcg gcccagtgcg ctgcttccgc tgttcgcgcg ggtgccggca gcctgttcgt   34500
tggagtcgtc gtggcttcgg agcccgtccg ggaagtacac gccgtgggcg ctggcccatg   34560
ctgcccgggt gtcgctcgcg tgggggaacg agtaccgcaa ggacgcgggc gatgcggctt   34620
cggcggcctc cctcgggtcc tcgccctctt cctcgtcgct ctcgttccag tcgagagcgc   34680
ggccgggtcc cgcccatccg cacgagcaca ccgcgcgcaa cgctgccgcc cgcggtccgc   34740
catgaggccg gccgtcgtag acgctccgct ccgatagcca cctggcctcc gctccggaag   34800
agctgaggaa gagcacagga tccgggacgg tgccatcggc cagcaacacc ccgaccgcac   34860
ccacgtggga cgaccgaac tcctccgtcg tccacgtctc cctctcacct tcacccatcg   34920
tctcgcccct ctcctcatcg ccgcatccgc acccggccga acgcacggat acagacgatt   34980
ccggagtcca aggttccgca cagcgagatc ctcgaaaagg tgacctcgca cctccaccgt   35040
gcaccaggcc tcaaagccca cgacgagccg accgagcgca gaccaccgaa gacgaagcgc   35100
atcgccgctt cccagtgcgc tggttgatga ggttcaggaa agcggggtca cttctctaca   35160
```

```
tcggacagct accgcagctt gccgcgcccg ccgcccggag cggcggttgc tcggcgcccg   35220
cgtgcgggtc ggaagcggag gctcggccgg cgaggttcgc cgtcgatgcc ggcggcacga   35280
cgggccagct ctccgatctt ctcctcgggc agtccggaca tcctgacggc ctggcgcact   35340
gcggcccggc agtcgggccg tgagcagtgc gccgacgata ccggccgtcc gaccgtcgga   35400
tgctcgggcg gcaggtagat cgctgcgcag ccgacgcaca gatagattga tcgcaaggcg   35460 cttcccttc gtcagctgag gccgctgccg tggcaggtat tgcaggagcc ggtccagcta   35520
cgggcgacgg gcttctggtt cccgtcctta tcgacttcga cagagtgctc ggtgtgctca   35580
gtgactccgg atccgctgca agcggagcaa ggcacgtcag acattttccc aggatgcccg   35640
attctgtggg gccgtgtcag tcgtcccgcg cactcgcgc gctaccggac cgggcgggcc   35700
catcccgaga atctcccgcc tgcatcacgg cggcgccaac ggcgagcccg aacctctggg   35760
ccacgcggtc gctcgccggc ccggtgggcg acctcgtgcc gccacgttcc cactgcgcgc   35820
tgttccgcca ctcccccgcc ccccaggggcg agtcctcgct gcgctcgcag tactgccgca   35880
cgagcaggtc gcccgctccc ggagaggccc cagcatcacg gcccgtcaag gtgctccgga   35940
tcggtggtgg ccgttgtgaa cgccacgcg ccgcccggct cgtcggcctg gccatcgccc   36000
ggcctggtcc cgctcaggat gccggggcgg tcaggacggc cttggcagcc agccggaaat   36060
tcctgatcat cggattcggg tcgcccttgc ggctgaccag gacgacccgg ctgggggag   36120 cgccctcgac cgggacggtg acgaggtcgg gacgcagtga gctgcgccga tcgccgaccg   36180
gtagcacggc gatggccctg ccgctcgcga cgagttcgag cttgtcctcg tagctctcga   36240
tcggcggcac gccggtcccg aggaactggt aggaagccca gcctgcggtc tcgaacgcac   36300
acggcgccgc ctcttcgccg gccagttctt ccgcggtcac cgacgcgcgg tcggccagag   36360 gatgccgcg cgggaccacg agcatccggg gctcctcgta cagcggggtg gtgaacacgt   36420
cgtcggcgac gagcggcagc ggggcccgcg cgatcagggc gtcgacgcgc ctgtcggaca   36480
gtgccccgac gtcgcggcag tgcagatgcc gggtggcgat tcggcgtcg gggtaacggc   36540 ggcgcagttc ccgcacggcg gcagtgatca ccaggtcttc gacgtagccg atggcgattc   36600
gttcggtccg ggcttgttca cgcacggcca gctcggcctg gcgggcggcc cgcagcaggg   36660
cctgggcccg ggggaggaac gtccggccgg ccggagtgag ccgggtgccc tgggggtgc   36720 ggtccagcag tcgtgtgccg agatatttct cgagccgttg gatctgacgg ctcagcgccg   36780
gctgggctac gtgcaggtcg gcggcgcccc ggccgaagtg ctggtgcgcc gccaccacgg   36840
tgaagtagcg caccagccgc agttccaggt cctgcccgag atcgttcacc ctcgcagggt   36900
acgcgtcatg ccgtttcgga atggtcagat tgccgaaccg gtcttggacg gccatgccgt   36960
cccgggcttt gactgaagga gcaacgtttc cccgagaaag cgacaggcgc gatgaaggcg   37020
atccagatcc acgaagcggg tgggccggaa gttctgcggt acgacgaggt gccggctccc   37080
gagatcggcc cgggcgaggt gctcgtccgg gtgcacgcgg cgggcatcaa cccgccggac   37140
tggtacctgc gtgaagggat gaaggtcatg ccggccggga tgaggccggc gctggagttc   37200
cctctgatcc ccggaacgga catgtcgggc gtggtccagg cggtcgctcc ggacgtgccg   37260
gggttcggcc tcgcgacga ggtcttcggc atgctgcggt tccccggatt cgacggccgg   37320
acgtacgccc agtacgtggc cgcgccggct tctgacctgg ctcacaagcc ggccggtatc   37380
gaccacgtgc aggcggccgg ggcgccgatg ccgtgctca cggcctggca gtacctggtc   37440
gacctcggcc acgaggtgcc gtctcctttc accggcagg tgcaccagcc ggtgccgatc   37500
acgccgggga tgaccgtgct ggtcaacggg gccgccggtg gagtgggcca tttcgcggtg   37560
```

-continued

```
caattggcga aatggaaggg ggcacacgtc atcgcggtgg cctcaagtcg gcacgagcgg    37620
ttcctgcgcg agctcggtgc cgatgagttc atcgactaca ccacgacgca ggccgcggac    37680
gtggtcagcg gtgtcgacct ggtgatcgac accgtcggcg ccccggacgg ctcacgcttc    37740
ctgaccgtac tcaagcgcgg cggcaccctg ctcccggtgt tcttcgccga gtacgacccg    37800
gaagagacgg cgagtctgga catcaccgtc tcgaacattc aggtacgttc ccacggcccc    37860
cagctcgccg agatcgggcg cctgttcgac gagggcacac tccgggtcgg ggtggacagc    37920
acctacccgc tgtccgaagc ggtcagcgca cacacgcgag ccgcgcaggg ccacatccaa    37980
ggcaagatcg tgctgacggt ggcctcgtga tcgccgaaac tccagcaggc ggtggcgaac    38040
tacgcccacg ccttggacga gttgcatata cccgagctgg aaacggtcct ggccgaagac    38100
accacctgga ccgtcacgat gcccggacag gggatgctcg gccccgtcgc cggacgcgcg    38160
gccgcggcgg tgctcgactt catcttcatc ccccgtgtca gctcggtgag cggtgtccca    38220
gaccggcccg ggacctcagc agttgccag ccgacccgat gagcgcgggc gccgagttgc    38280
ccgcgagcag ccgcggcgcc atcttgacgg gcaggcccag tcgcgctgcc gcgtcggatt    38340
cacgccggtt tcctcgggtc gctgtcggcc aagtcagcgg tcattgtgcc acccgtccca    38400
cttcggaaga cgctgaccgc cgctcccccg atcctggatg cggcggcttt cacggcacgc    38460
tgctccgctg ccgtgccgac gaggtctccg gacggctgag ccgtgctgcg catgccgcgc    38520
cgcctcggcg accgatcgcc gcgcagcgtc agatgcgccg gactttcgcc acggcaaggg    38580
cgtccgcgac ctcccggacg acacgcttcg cgtcgtcggg gctgttcacc acgtcggtgc    38640
ggttcatgtc gatcacgagg acatcgctgg cggaatagtg ctcgtgcacc cagtcgtcgt    38700
acccggccca aagcgtccgg tagtactcga cgagactttg gtcctgctcg aagtcacgcc    38760
cccgcagtcc gatgcggcgc agcaccgtct cgaagtccgc tctgagatac accatgagat    38820
cgggtgcctt gcgataggc aggccgtcga tctcacgcat catctccgcg agcaacccct    38880
cgtacacctg catctccagg gaactgatcc tgccgaggtc gtgattgact ttggcgaagt    38940
accagtcctc gtagatcgac cggtcgagga cgttgtcgtc ctgtttgtac gcctccttga    39000
tcgcggcgaa tcgcgtctgc aagaagtaga gctggagaag gaagggatag cgcttcgccg    39060
ctatctcctc aggaccggcg gtgtagaaga gcggcaggat cgggttgtcc tccacgctct    39120
cgtagaagac catgctcccc agctctttgg cgatcagctc ggccacgctt gtcttcccga    39180
tcccgatcat gccgccgacg cagatcactg ccatacctcg cttctttccc gggacaccgt    39240
ccgcgggcgc gattcccgcg caccggctct tccacggcac acgcaccgcc gcggagcgca    39300
gtcgtggaag cgccccaggc gcaggtgacg agcctggcct ccgtcggacg accgaagcgg    39360
catcatatcg gcacggaggg gtgttcgaat ctacgtgctc gtgccctgga tggaagacgc    39420
tggtgcaccg ggtagcggga tcatcggagg tgatcatgta gcgggtgggc ggaacgacgc    39480
ggaacgacgc agtggtggga caggggccac tgacgcacgt atccgcagcc gcgctggagt    39540
cgccgacctc cacaggttca ctctcaccgg tgaccaagga aagatcgccc gcatgccagg    39600
ctcgcccgct cctccccgga acagcgcgta caccgatcag gagaacgacg ccgcgacccc    39660
gagcgagcag ccgagcctgt gtggacgccg aacgtgtcgg ttaccactcg acgaccagcc    39720
ttgacacacc gcgcgtcgcg aggccctccc gccatacgag ggcctcgtcc cccggtgcga    39780
gtcgcaggcc ggggaagcgc tgccacaagc gggtcagcgc gatcttcatc tggagaagaa    39840
ccagtggcgc gcccatgcac cggtgggcgc cgtgtccgaa tgtgaggtgt gcaggccggc    39900
```

```
gggcgctgct cttcgcaccc gatgtgcaaa atacttcggc gtcatgattg ccgtgcagca    39960
acgagacgat gacggcctct ccttggcgca ccgtcgtccc gcccaggaca aggtcctcga    40020
tggccactcg gggaaaactg ataggtgtgg acggcgtctt gcggagcagc tcctcaacca    40080
gatcctccac ggattgcccg tcgagcgcgt caccggtgag cagttcgagt atggcaaggc    40140
tcaattgatg ggcggtggtc tcgtaaccgg ccatgagaag tgccagtccg aggttgatca    40200
actcgatgcg ggatatctca cccgactgct caacccgcac cagcgcgctc aggagatcct    40260
gcccgggcgc atccctcttt ctttcgatca gtgaggacat gtacttgata agagtcagga    40320
tatggcggcc tcttctgcgg gttccctgag gcgtcatgtc gaacagcgca gtcacggcgg    40380
cgtcgaaaac gggccgctcc gccgccggca cgccgagcag tgagctcaac gcgaccatgg    40440
gaaggggcga agcataaccg ctgaccaggt cggcgcctgg ccccgcaacc tgtagccgat    40500
ccagcagtgc gtcggcggcc tcctcgatca ccgctgcctg tgcggtgact cgggcgctgg    40560
tgaacgctgc tccggcgacc cggcgcagcc gggcgtggtc cgcaccgtcc agactcatga    40620
tcgagttggg tgagaggtcg acggatcccc atttcggagc atcggggtgg gtggccgcag    40680
ctctgctgag acgtgtgtcg gcgagcgcgg cgcgccccac ggcgtagtcg gtgaccagcc    40740
acatgtgatc accagtgggc atccgcaccc gtttgacggc ctcacttgat ggcgctgcca    40800
ggaagggcgg cagggggccg accctgtggt gatcgaaagt gccggacatg gtcgattact    40860
cctgttcggt cggaaacgcc gcggggtgtc tgtctcccct gccgccgacg gccgtgggag    40920
acgacccatc gggtggcggc cgggtcgggc gagcgggctt tttccaccgc ccggaaggcg    40980
gcccgctgtt cggtctgcac gctgttcggg ctgcccggct tcggcggaca gaccggcttt    41040
ggcggacaga ccggctgccg gatgttcgtc acgtagcgcg cacggtgtgt tccctgcctc    41100
tcagcgcatc ccgccgtcgc ggcctgacgc gttggacgcc tgtggtctca gccgagcgtg    41160
ggcaccgaac tgcgtcggcc cgtcgacctg cgctctgcgg gacaggacga ggtcccggag    41220
tcgctgtggc agggcgtcgt caaagcggag gtggtccggc accgtgacgc cggcgttgcg    41280
cagcggcgtc gcgatctcgc ggcaggtggt gctgagccag ttgaggaccg cgggatctcc    41340
cgagcggccc gcgaccggcg tccaggtggc cacttccggc tgccggaggc cggcgtcgag    41400
gaacgtccgg gtgaggcggg ggccgaagtc ggggacggcg ccggccgcca ggaaggggcc    41460
gggccacagc gcgtagtact cgtcccactc cggcagcggc ggacgtgacg gcgacgtgtt    41520
ggtgaagtcc atctcgtgca tgacgacgat cccgtccggt ttcagcaggg acgtcagacg    41580
gcgcagtgcg gatgcgggat cgggcaggta catcaggatg tacctgccga ccaggacgtc    41640
gaacttcatc ggccaggtga agtcggccag gtccgcggct tcgtaccgca ccgagtccgc    41700
gagccccgcc tcctgtgcca ggatccgcgc cttgtggacg gttccggggt cgcgctcgat    41760
tcccacgacg tgtccgccgg gcccgaccag ttgggcggcc agcagagaga cgtatcccag    41820
tccggcaccg atgtcgagga cgctcatccc cggacgtact ccggccgacc gcagggtgcg    41880
ttcggtgaac ggcgagatcg cctcgttctg aagggtcagc ctttggtgct cgctatcgga    41940
gtaaccgagc aggtatgcgt cgtgcgccat gcgaggcctc cagggccggt cgtgcgggga    42000 gttcccacg gcaggtggcc aggggctccc gcggtgtctg gagcactgag tgccctgtag    42060
cggccgtgcg gtgtggtccg gtgttccggg tatgtcacgc accggagcgg gacatgtacg    42120
tgtccgaagg cggcgggcgg cgcagagcct tgccgctgga ggtgcgtgcg atcccgccgc    42180
gccgcacgaa ctcgatcgtg tcgggtgtga tgcccagctc ggccaccaca cgtgcgcgga    42240
tgtgttgcgt cgtggcacga cggctcgcct cgtcgtgccg cgtcgtctcg acgacgagcc    42300
```

```
cgaggcggcc tccctcgtcg ctccagatct gctcggccag gacgccgtgg acgaggaggc    42360
cgggtgtgtc ccgcacgacc gcctcgatgt cgctcgccca gtggttcgcg ccgaagacga    42420
tgatcacctc tttcgtgcgg cccacgatgt acagctcgcc gtcgtgccac aggcccaggt    42480
caccggtcgc caaccagccg cccggaagga ggacgcgacg gctctcttcg gggtggcggt    42540
cgtacccggt gctcgtgacg gacgcccccc ggacctcgac ggcgccgacc gtgccgggca    42600
cggccggtgc gccgctcgcg gtggtgagcc ggacctcggt acgccgcacc ggcgttccca    42660
cactgaccag ttcgcgacac ggcccggcgc cggacggcac cggtacgtaa cggccccggt    42720
tcagttcgtc ccgtcggca cgcagcacct tggccgggcg gccgagggga gggaaggcga     42780
ccgccagggt cgcctccgcc agtccgtagg ccggcaggaa gacgttctcg gacagtccgg    42840
cgggcgcgaa acgctcggcg aaggcgtcct gaagccgccg gtcgaccggc tcggcgccgt    42900
tcaccgcgat gcgccagcgg gagagatcga ggccggccgg cggcgccgcg tcgcgcctca    42960
ggacgtagcg gtagcggag tcaggagcca tggtgaaggt cgcccccagc cgccccatgg     43020
cccggatcca gtcacccgga ctgcgcaggt agtcctccgg tgtcagcaga tggatgtcga    43080
cgtcgtgcag cagcggtgtc aagaaggaac cgatcaggcc catgtcgtgg aagaggggca    43140
gccaggtgca gccgacgtcg gtcctggcga gccgtgtgcc atgggcgatg gccgccaccc    43200
cggccgccac gttgccgtgg ctgagcacga cgccccgcgg ttcgctgctc gtgcccgacg    43260
tgtactgaac gacggccggg tccgacgccg cccgcgcgac gtgggccgcg gacggctcgg    43320
ccacctccgg caccaggagt acgtcgaccg ggcgggcgcc gtcggacagt ccaggaccga    43380
gcagcgggcg catggccgga gccgtcagca cggtccgtac ccgagagcgg cgcagggccg    43440
cggaggtgcg ccggagatag gcgtcggacg acccgaaggg cgcgggaccg ggcagcggca    43500
ccgcgaccgc gcccgccgcc agcacgccga agaaggcgcg cgcgaagtcc accgacgtcg    43560
gcaggacgag ggcgacccgc tcgccgggtc gcacccgcg cgacagcagc cccgcggcca     43620
cccgcccggc ctcggcgaag aggtcgctgt aggacagcgc gtcgccgtcc tggccccggc    43680
gcagcacgtg catgccccgt ccggagcctt gtgcggcgac gcggccgagc gcggcgaaca    43740
gggtcacgac agcggttccg tgccggcctc cgcgatcacc ttggtgatcg cggccgcgaa    43800
ctcccgcacg gtgctcgtct cgaagacgat gcggtcctcc acctcgatgt cgtagtgctg    43860
ctcgatctcc agcacgatct ggagcgcgtg gatcgagtcg aagcgcggca aggagcgcag    43920
atcggtgtcc acgcccacct cctcgacacc gatgcgcagt tgctcggcga cggatcggcg    43980
gacggtctgt tcgatgtcgg tgacactcgc ctgtgacatg gcgtggtgtt gtcctgttct    44040
gtgaggccgg cgcgtcgggg cgcggcggga ggcggacgcc gggactgacg gtcagcgagc    44100
gccgggccgg cgggccaggg cgcgcagctt ggctttgatg tccgcggggg tctccaacga    44160
gtcgtcgtcc gccaggagcc ggacgatcga catcaccttg gcgtccgcgg cgtccaccga    44220
gtcgtgctgg atggtctcga tacgcggat gccggccgtg gatgtggaat gcgggtagaa     44280
catgcccgcc gggtgcttga cgccgttgct acggtccgcg agccagatgt aggccatgcg    44340
cagcgcggcg gcctgatggg ccggatcgct gtcgcacagt tccgcatgaa gacggagaa     44400 cgcacggcag tgccgggcct cgtcgcgggc caggagccgc cagattctgc ggatcaccgg    44460
ctccgacaca tgggcggcga gcgccttgta gagggcggac gcgcgtgact ccgagatcac    44520
gttcatcatg agggtggcgg agcgcacgtc gccctgcgga tacggctctc gtttgtagag    44580
cgcgtgcttc gaacggagtg agaccccgat ccggtccagg tagcgggcct ggaccagtga    44640
```

```
gtgccgggat tcctccgcac cccattgcag tgcccaggag gagaagctga cctcgtcctg    44700
ccattcccgc aggaagttgt gagcgccggg tagggtgccg aactcgatga cggccgcctc    44760
ggtgaggaag tccacggtcc gttcgtcgag catgccgtgc tcgatgcggt ccaggtccac    44820
ctcggtccag tcccagcgcg tcgtctcgaa ccagtcgaag atcttgttga aggtcatgtc    44880
gaggtagtag tcggtgtaga ggtcgtccgt catcagcgcg cggtgcgccc gcagggccag    44940
ttcgaccgag gtggtgaacc cttcgggcgc accgcggcg ggccggacga tgtcctcgac    45000
gtccagtgct tccgcccagc cgggaaccgg gcccgccgta tcgggcccga cgacgtacac    45060
ccgggtccgg ttgaacttcg agtgcgaccg cagcgcccgg acggcgggca gcggctcggc    45120
gtccgccccg atccacaccg ccgcgagctc ggatgacggt tcgaactcgt gcaggtagcg    45180
gtgccagtcg gcgtgtgccg gccggtccac ggtgacgtcg ccgaaggcgg ggacggtgag    45240
cctttcggcg ggggagactg cggtggtggg tgccagcagg gcgatggtgt gcggggcac    45300 ggagggcgtc ctctctgtcg gtctgcgcag gccgtcggcg agcaccttgc cgcgcgttgt    45360 gtgggctcg gctccgtaac acgtgcgtgc cgcgacgtca gagccgcccg tactccgcgg    45420
cagggccgag gagtacgggc agcgcctcga tgctgttgct gacgaacgag ggcacgggcc    45480
gcacggtcca cgtgtcggac ggggccagcc gcacgtcggg gaaccgggtg aagaatccgg    45540
ccagtgccgt ctccagctgg agacgggcca ggtgtgtccc gatacagaag tgcgggccgt    45600
gcccgaagcc gaggtggccg gcctgccgcc ggcggacgtc gaagaggtcc gcgtccggcc    45660
cgtggtgcgc cgggtcccgg cccgccgagc cgaaggacgc gaggatggct tctccccggt    45720
ggatcgtctg gccggcgatg acgacgtcct cggtcgggta gcgcatcggg aactggttca    45780
ccgcgccgtt ccagcgcatc gtctcctcga ccaccgcact ccacgggacc tccccggcgc    45840
gggcggaggc cagttgctcg gggtgggtga gcagcgcgtg gcaggcgttg acgagtacgt    45900
tgatgacgct ctggtggccg gcgaagaaca tcagcaggat catgccgtgc agttcgctgt    45960
cggtgagccg gtcgtctccg tcctggcgtg ccgtgagcag gacgctgatg aggtcgtccc    46020
gggggacgtc gcgacgttcg gcgacgatct cccggagcag cgcttcgatc cgtccgtcga    46080
tctcctggac ctgttcgggg gagttgttcg tacgggtctg catgccggtg agcacgtgca    46140
gcagacgccg cttgcgctgc gggatcccca gcaggtccga gatgacggtg gtggggatgg    46200
ggtaggcgaa agccttgcgg agatccaccg gccggtcttc cggccgtgtg gcgagctggt    46260
cgaggagccc gtcgacgagg cgttccaccc ccgggcgcat ggcctccacc cgttccgggg    46320
tcagtgcctg gtcgaccagt ccgcgcagcc gccggtgatc cgcgccgtgc gaattgatga    46380
cgctgtcggt cgcgacgaag cccatcaacg gccacccgtc cggcacttcg ccgcgggccg    46440
ctgcctccca gtgcgtgatt cccttggcga ccctgggatc cgtcagcact cggcgcaggt    46500
cctcgtggtg cggaatcgcc cacgcccgca caccgccggg gagttggacc ggaacggctc    46560
tccccgccgc ccgcaggcgg gcgttctccg cgtgct                              46596
```

<210> SEQ ID NO 4
<211> LENGTH: 37
<212> TYPE: DNA
<213> ORGANISM: Artificial
<220> FEATURE:
<223> OTHER INFORMATION: Primer

<400> SEQUENCE: 4
cagagaattc gcggtacggg gcggacgaca aggtgtc                                       37

```
<210> SEQ ID NO 5
<211> LENGTH: 39
<212> TYPE: DNA
<213> ORGANISM: Artificial
<220> FEATURE:
<223> OTHER INFORMATION: Primer

<400> SEQUENCE: 5
gcgcatgcat gtgccggtgc cggtccgcga gccgcttgg                          39

<210> SEQ ID NO 6
<211> LENGTH: 40
<212> TYPE: DNA
<213> ORGANISM: Artificial
<220> FEATURE:
<223> OTHER INFORMATION: Primer

<400> SEQUENCE: 6
cctcatgcat ctggaggacg tcgcaggtga attctgggcg                         40

<210> SEQ ID NO 7
<211> LENGTH: 33
<212> TYPE: DNA
<213> ORGANISM: Artificial
<220> FEATURE:
<223> OTHER INFORMATION: Primer

<400> SEQUENCE: 7
gggcaagctt ctcctggctg agcttgaaca tcg                                33

<210> SEQ ID NO 8
<211> LENGTH: 3994
<212> TYPE: DNA
<213> ORGANISM: Artificial
<220> FEATURE:
<223> OTHER INFORMATION: DNA fragment

<400> SEQUENCE: 8
cagaggatcc gcggtacggg gcggacgaca aggtgtcgtt gccgcgccgg cactcggact    60
ctcgcagcct cacaacgctg ctggccgcgg cggtgtacct cacgtcgcgg gcggtggacg   120
acgcgctgga tctgctgaag gtcctgatcg cgacgaagct tgcagaccgg ctgcacatcc   180
tggacggcgg tgctggacgc cacattcgaa aagcgcctgc tcaatacccg cccccaacgg   240
agacgaggtt gaacgacaag ctcagggcgt ctgagtactc cggttgagta gttctgccca   300
tgtgaggggc agggccgtcg agacaggctg tgtacacaac gccgcggtgc gcagagcgct   360
cggcgaagag accagtagcg gtcatctatg aggggatact tcatgtccaa gcgccttgtc   420
gtctcgtcgc tcgccgtggc cgcagccgtc gttgccggca ccgtggtgtt cgtctcctcg   480
gccgacgccg ctgtgccggc caagccggag atctcaaagg ccaccgccca ctacaccagt   540
acggccggtg ggagcgcctc gctcaccttc agcgccaccg tggccgacaa ctccggaatc   600
aagagcctgc gggtgctcgc ctggccgcg agttcgggcc ttgcgcccac ggcgggcgag   660
atgcgggatg tcgaggaagc cacgtgcaag gcgacttccg cgacggcctc ggtgtgcacc   720
tacaccgtga agagctcggc caaggaagcc gccgcgttgc ccaagggcgt ctggcacgta   780
tccgtgctgg ccaccgccaa ggaccacgac acgaccttcg cgccccaagg cgccacgttc   840
accgtcaagc actgacggct ccgccccgcc ggaatgatga tcgcggcccg cgcgccgggc   900
ggaccgtatc gcgacctcca ttggacccgt tgaaccgcac gacgcggtga actccgccca   960
ccctgcccca gggcggacgg agttcacctg ggggcgacgc cgcgcatctg acgcgcgctg  1020
```

```
ccacgatgcc gcaccactcc gcgcgcgggc ggatgcaggc gaagtgactc ccagctcgac    1080
gcgctcgcca aacacggcat ctcgcgcgac tacatcttcg gcgagaagat cagcacccgg    1140
gcgcggggca gcccgaagtt ccgggaggag gcgctgaggg cggcgcggga ggtcaaggcg    1200
cacgccccac actgccgtgt catcttcacg gtgtacgagc ggaagcggct cggtcgcaac    1260
gccgccgaac tcaccgccct cgccgaccac ctcaccgccc acggcttggt cctggagata    1320
ttcgccgggc cctgtcgaag gactcccgga gccgtggaac ccggcgccca cccgacgcga    1380
cagcccgacg cggcagttgg ggcgctcccg cgcggcctgc ccggacaccg aaacgcccgg    1440
caccacaagc gaaagagcgt ccgtcggcaa gctgacgggt cctcatgaag gatttaggcc    1500
agtgatttgg gacacacccg aacgcgccgg ccggatctga ggaatcgcct agggcccgct    1560
cctatcggga acttgaagcc gccctgccga gccaacgctt gactccggtt ccggcggtgc    1620
ggatgacgat aatttccggt gagtctgccc aaaagggtac atagcgggcg catagaaaac    1680
tcttgcgagt gctgcgggtg gcttgtaggt cctaatgaa tcggctggac aagggaaggt    1740
tgatgcgggc gtccgaacca aaatagcttc ggacagcaac tgctgccttc tgtcgatgga    1800
agtaggggga agttcgtgga aatcggctcg ggcgcgcccg aattaaccgc gtcgtcggtg    1860
tatcagcagc ggcgtgacca aatcgccgca agcgctgccg cctatgtgcc cggcgagccc    1920
attccagagg tcgagtacac ggacgccgag cacgctctgt ggcgcctggt ttccaagcgg    1980 ctcgcgggacc ggcaccggca catgcatctg gaggacgtcg caggtgaatt ctgggcgtcc    2040
tgcgacgata catccattga aaaactaatg gcggttgata tatgacccgg ctcgcagagc    2100
aatcatccac tgcgcagcag agcccggaat cagaagtact ggacgtcacc ggaatcggat    2160
tcggtgccgc gaatctcgcc ctggcggtgg cgctccatga atccgaagcc gccgggaagg    2220
cccttttcct ggagaagcag aaggaattcg gctggcatcg ggggatgctc ctgggggct    2280 cctcgctcca ggtgtccttt ctcaaggaca tcgccacgat gcgcaatccc accagtgatt    2340
tcggattcct gtcctatctc caggagaagg accggctggt cgacttcatc aaccagcaca    2400
ccctgctgcc ctcccggatc gagtaccacg actacctcca gtgggccgcc gaccggctga    2460
accacctggt cgagtacggc gtggaggcca ccggtgtgcg gccggtgacc gaagccggtg    2520
aggtcgtcgc gctcgacgtg ctcgccgggg accgggtggt cgcccggacc agaaacctcg    2580
tcctcgcctc cggcctgcgc cccggctgc ccgaggcgc ggagaccggc gaacgcgtct    2640
ggcacagctc ccagttgctg caccggctgc ccgcgttcga cgaacgcccg ccccgccggg    2700
ccgtcgtggt cggcgccggc cagagcgcgg ccgaggtcgc cgcgcacctc atggaccgct    2760
acccgcaggc cgaggtgtgc gcggtgttcg cccgctacgg ctacagcgtc gccgactcca    2820
gcccgttcgc caaccgcgtc ttcgaccccgg ccgccgtgga cgacttctac ttcgccccgc    2880
ccgaggtcaa gcaggccatc atgcgctacc acggcggcac caactacgcc gtcgtcgacg    2940
aggacgtcct ccagggcctc taccgccgcc agtacgagca gaaggtgtcc ggcgccccgc    3000
ggctgcgggt gatgaacgcc tcccgcctgg tgtccgtcga accgcgccag gaatccgccg    3060
ccgtacgcgt ggagttcctg cccacgggcg aacacaccga cctggacgcc gacctggtcg    3120
tgtacgccac cggtacgac tccaccgacc cggccgaact gctcggcggc gtctccggcg    3180
ccctccgccg ggacgaggcg ggggagttgc tgatcggccg cgactaccgg ctcggcacca    3240
ccggggattt ccggtgcggc atctacgtcc agggcgccac cgaggcgacc cacggcatcg    3300
cctccaccct gctgtccatg gtggcggtcc gcgcgggcga gatcgcccgg tcgatcaccg    3360
gcggccggtg cgacccggac cgctccaccg gaagcaaggc agcagcgggg aacagggggct    3420
```

```
gaagtgtacg aacgtccgct gtaccgggag gattgcgacg gcgtcgtcct ggcgtttctg    3480
cgacacaacc cactggcaat ggtcgtcacc tcgcacgacg acgtcccggt ggccacccac    3540
gcgccggtgc tgttccggca cggacccgac ggcgccgacg ccgaggccgt cgccgcgggc    3600
accgtcccgc tcgccggctc caccctgatc ggccacatga acgtcgagaa cccgcagtgg    3660
cgccggatgc gctccggcga ccgggcgctc atcgtcttcc agggcccgca cggctatgtc    3720
tcgccgacgg tctacggggt cacgcccgcg gcccccacct gggacttcat cgccgtccac    3780
gtgaacggca cagtggagcc caccgccgac cccgccgccg tgctggacat cgtctccgac    3840
accgcccggc ggctggagtc cggcttcggg cgcggctggg accaggagtc ctccctcgac    3900
tacttccgcc agatcgcgcc cggcgtgggc gccttcaccc tgcgggtcga ttccgtgcag    3960
acgatgttca agctcagcca ggagtctaga gccc                                3994
```

MACROCYCLIC COMPOUNDS AND METHODS FOR THEIR PRODUCTION

This application is §371 application of PCT/GB2012/050707, filed Mar. 29, 2012, which in turn claims priority to GB Application 1105293.3, filed Mar. 29, 2011; GB Application 1113629.8, filed Aug. 8, 2011; and GB Application 1202060.8, filed Feb. 7, 2012. The entire disclosure of each of the foregoing applications is incorporated by reference herein.

INTRODUCTION

The present invention relates to sanglifehrin analogues, that are useful both as cyclophilin inhibitors, e.g. in the treatment of viral infection by viruses such as Hepatitis C virus (HCV), Hepatitis B Virus (HBV) and Human Immunodeficiency Virus (HIV) and/or as immunosuppressants e.g. for use in prophylaxis of transplant rejection and as anti-inflammatory agents, e.g. for use in inflammatory disorders. The present invention also provides methods for their use in medicine, in particular for the treatment of HCV or HIV infection and for use as an immunosuppressant or anti-inflammatory agent, in diseases where inhibition of the Mitochondrial Permeability Transition Pore (mPTP) is useful such as muscular dystrophy or as intermediates in the generation of further medicinally useful compounds.

BACKGROUND OF THE INVENTION

Hepatitis C

Hepatitis C virus (HCV) is a positive strand RNA virus, and infection is a leading cause of post-transfusional hepatitis. HCV is the most common chronic blood borne infection, and the leading cause of death from liver disease in United States. The World Health Organization estimates that there are more than 170 million chronic carriers of HCV infection, which is about 3% of the world population. Among the untreated HCV-infected patients, about 70%-85% develop chronic HCV infection, and are therefore at high risk to develop liver cirrhosis and hepatocellular carcinoma. In developed countries, 50-76% of all cases of liver cancer and two-thirds of all liver transplants are due to chronic HCV infection (Manns et al, 2007).

In addition to liver diseases, chronically infected patients may also develop other chronic HCV-related diseases, and serve as a source of transmission to others. HCV infection causes non-liver complications such as arthralgias (joint pain), skin rash, and internal organ damage predominantly to the kidney. HCV infection represents an important global health-care burden, and currently there is no vaccine available for hepatitis C (Strader et al., 2004; Jacobson et al. 2007; Manns et al., 2007; Pawlotsky, 2005; Zeuzem & Hermann, 2002).

Treatment of HCV

The current standard of care (SoC) is subcutaneous injections of pegylated interferon-α (pIFNα) and oral dosing of the antiviral drug ribavirin for a period of 24-48 weeks. Success in treatment is defined by sustained virologic response (SVR), which is defined by absence of HCV RNA in serum at the end of treatment period and 6 months later. Overall response rates to SoC depend mainly on genotype and pre-treatment HCV RNA levels. Patients with genotype 2 and 3 are more likely to respond to SoC than patients infected with genotype 1 (Melnikova, 2008; Jacobson et al., 2007).

A significant number of HCV patients do not respond adequately to the SoC treatment, or cannot tolerate the therapy due to side effects, leading to frequent issues with completion of the full course. The overall clinical SVR rate of SoC is only around 50% (Melnikova, 2008). Development of resistance is another underlying factor for failure of treatment (Jacobson et al. et al. 2007). SoC is also contraindicated in some patients who are not considered candidates for treatment, such as patients with past significant episodes of depression or cardiac disease. Side effects of the SoC, which frequently lead to discontinuation of treatment, include a flu-like illness, fever, fatigue, haematological disease, anaemia, leucopaenia, thrombocytopaenia, alopecia and depression (Manns et al., 2007).

Considering the side effects associated with the lengthy treatments using SoC, development of resistance, and suboptimum overall rate of success, more efficacious and safer new treatments are urgently needed for treatment of HCV infection. The objectives of new treatments include improved potency, improved toxicity profile, improved resistance profile, improved quality of life and the resulting improvement in patient compliance. HCV has a short life cycle and therefore development of drug resistance during drug therapy is common.

Novel, specifically targeted antiviral therapy for hepatitis C(STAT-C) also known as direct acting antiviral (DAA) drugs are being developed that target viral proteins such as viral RNA polymerase NS5B or viral protease NS3 (Jacobson et al, 2007; Parfieniuk et al., 2007). In addition, novel compounds also are being developed that target human proteins (e.g. cyclophilins) rather than viral targets, which might be expected to lead to a reduction in incidence of resistance during drug therapy (Manns et al., 2007; Pockros, 2008; Pawlotsky J-M, 2005).

Cyclophilin Inhibitors

Cyclophilins (CyP) are a family of cellular proteins that display peptidyl-prolyl cis-trans isomerase activity facilitating protein conformation changes and folding. CyPs are involved in cellular processes such as transcriptional regulation, immune response, protein secretion, and mitochondrial function. HCV virus recruits CyPs for its life cycle during human infection. Originally, it was thought that CyPs stimulate the RNA binding activity of the HCV non-structural protein NS5B RNA polymerase that promotes RNA replication, although several alternative hypotheses have been proposed including a requirement for CyP PPlase activity. Various isoforms of CyPs, including A and B, are believed to be involved in the HCV life cycle (Yang et al., 2008; Appel et al., 2006; Chatterji et al., 2009; Gaither et al., 2010). The ability to generate knockouts in mice (Colgan et al., 2000) and human T cells (Braaten and Luban, 2001) indicates that CyPA is optional for cell growth and survival. Similar results have been observed with disruption of CyPA homologues in bacteria (Herrler et al., 1994), *Neurospora* (Tropschug et al., 1989) and *Saccharomyces cerevisiae* (Dolinski et al. 1997). Therefore, inhibiting CyPs represent a novel and attractive host target for treating HCV infection, and a new potential addition to current SoC or STAT-C/DAA drugs, with the aim of increasing SVR, preventing emergence of resistance and lowering treatment side effects.

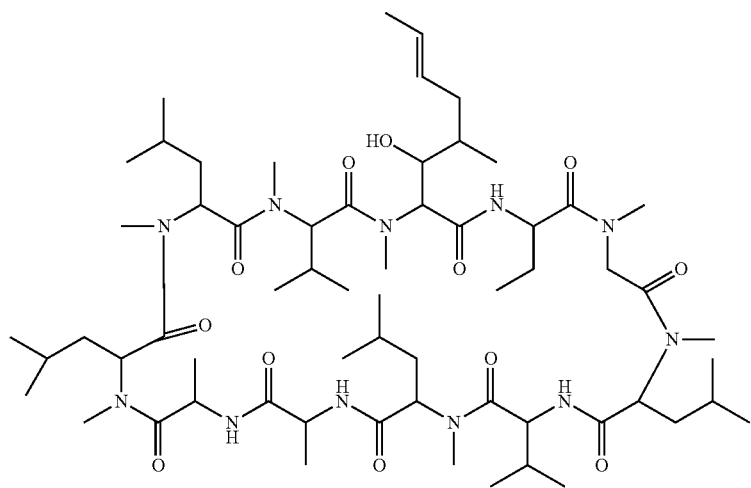
Cyclosporoine A, 1
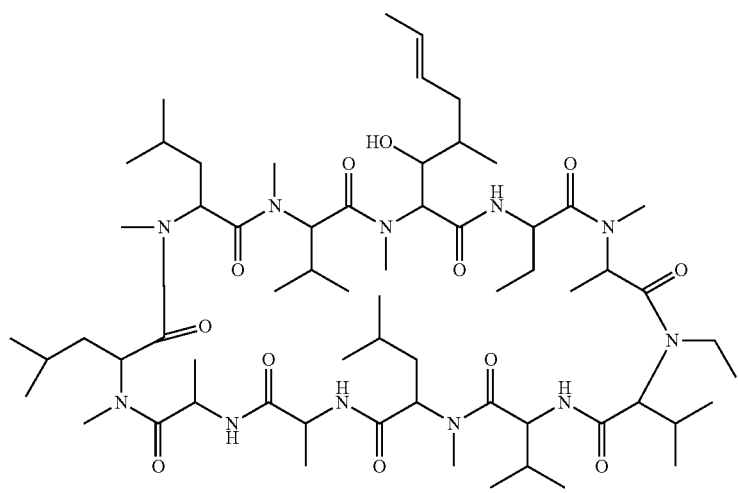
DEBIO-025, 2
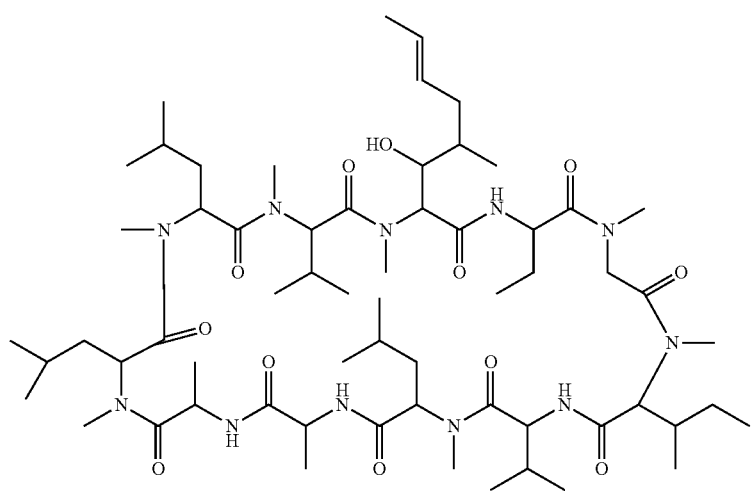
NIM-811, 3

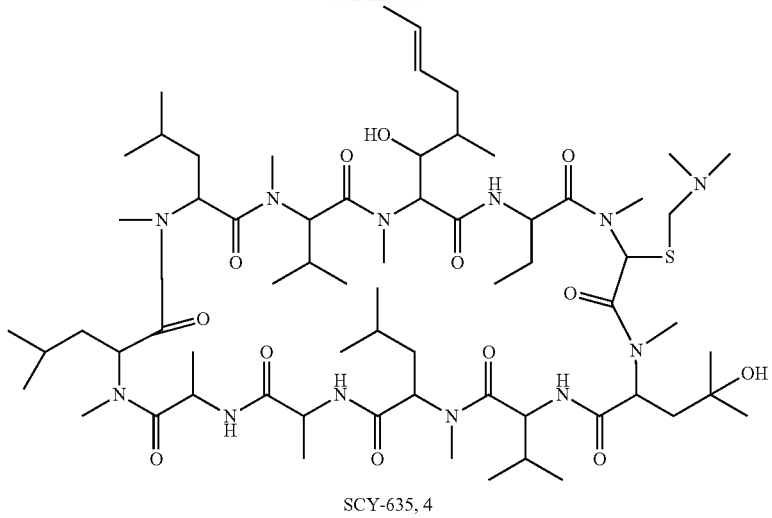 [SMILES: C/C=C/CC(C)C(O)C1C(=O)NC(CC)C(=O)N(C)C(SCN(C)C)C(=O)N(C)C(CC(C)(C)O)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C]

SCY-635, 4

Cyclosporine A (Inoue et al. 2003) ("CsA") and its closely structurally related non-immunosuppressive clinical analogues DEBIO-025 (Paeshuyse et al. 2006; Flisiak et al. 2008), NIM811 (Mathy et al. 2008) and SCY-635 (Hopkins et al., 2009) are known to bind to cyclophilins, and as cyclophilin inhibitors have shown in vitro and clinical efficacy in the treatment of HCV infection (Crabbe et al., 2009; Flisiak et al. 2008; Mathy et al. 2008; Inoue et al., 2007; Ishii et al., 2006; Paeshuyse et al., 2006). Although earlier resistance studies on CsA showed mutations in HCV NS5B RNA polymerase and suggested that only cyclophilin B would be involved in the HCV replication process (Robida et al., 2007), recent studies have suggested an essential role for cyclophilin A in HCV replication (Chatterji et al. 2009; Yang et al., 2008). Considering that mutations in NS5A viral protein are also associated with CsA resistance and that NS5A interacts with both CyPA and CypB for their specific peptidyl-prolyl cis/trans isomerase (PPIase) activity, a role for both cyclophilins in viral life cycle is further suggested (Hanoulle et al., 2009).

The anti-HCV effect of cyclosporine analogues is independent of the immunosuppressive property, which is dependent on calcineurin. This indicated that the essential requirement for HCV activity is CyP binding and calcineurin binding is not needed. DEBIO-025, the most clinically advanced cyclophilin inhibitor for the treatment of HCV, has shown in vitro and in vivo potency against the four most prevalent HCV genotypes (genotypes 1, 2, 3, and 4). Resistance studies showed that mutations conferring resistance to DEBIO-025 were different from those reported for polymerase and protease inhibitors, and that there was no cross resistance with STAT-C/DAA resistant viral replicons. More importantly, DEBIO-025 also prevented the development of escape mutations that confer resistance to both protease and polymerase inhibitors (Crabbe et al., 2009).

However, the CsA-based cyclophilin inhibitors in clinical development have a number of issues, which are thought to be related to their shared structural class, including: certain adverse events that can lead to a withdrawal of therapy and have limited the clinical dose levels; variable pharmacokinetics that can lead to variable efficacy; and an increased risk of drug-drug interactions that can lead to dosing issues.

The most frequently occurring adverse events (AEs) in patients who received DEBIO-025 included jaundice, abdominal pain, vomiting, fatigue, and pyrexia. The most clinically important AEs were hyperbilirubinemia and reduction in platelet count (thrombocytopaenia). Peg-IFN can cause profound thrombocytopaenia and combination with DEBIO-025 could represent a significant clinical problem. Both an increase in bilirubin and decrease in platelets have also been described in early clinical studies with NIM-811 (Ke et al., 2009). Although the hyperbilirubinemia observed during DEBIO-025 clinical studies was reversed after treatment cessation, it was the cause for discontinuation of treatment in 4 out of 16 patients, and a reduction in dose levels for future trials. As the anti-viral effect of cyclophilin inhibitors in HCV is dose related, a reduction in dose has led to a reduction in anti-viral effect, and a number of later trials with CsA-based cyclophilin inhibitors have shown no or poor reductions in HCV viral load when dosed as a monotherapy (Lawitz et al., 2009; Hopkins et al., 2009; Nelson et al., 2009). DEBIO-025 and cyclosporine A are known to be inhibitors of biliary transporters such as bile salt export pumps and other hepatic transporters (especially OAT1B1/OAT1B3/MRP2/MRP3/cMOAT/ABCC2) (Crabbe et al., 2009). It has been suggested that the interaction with biliary transporters, in particular MRP2, may be the cause of the hyperbilirubinaemia seen at high dose levels of DEBIO-025 (Nelson et al., 2009, Wring et al., 2010). CsA class-related drug-drug interactions (DDIs) via inhibition of other drug transporters such as P-glycoprotein (Pgp/MDR1), BSEP, OAT1B1 and OAT1B3 (Konig et al., 2010) may also be a concern, potentially limiting certain combinations and use in some patients undergoing treatment for co-infections such as HIV (Seden et al., 2010).

Moreover, DEBIO-025 and cyclosporine A are substrates for metabolism by cytochrome P450 (especially CYP3A4), and are known to be substrates and inhibitors of human P-glycoprotein (MDR1) (Crabbe et al., 2009). Cyclosporine A has also been shown to be an inhibitor of CYP3A4 in vitro (Niwa et al., 2007). This indicates that there could be an increased risk of drug-drug interactions with other drugs that are CYP3A4 substrates, inducers or inhibitors such as for example ketoconazole, cimetidine and rifampicin. In addition, interactions are also expected with drugs that are subject to transport by P-glycoprotein (e.g. digoxin), which could cause severe drug-drug interactions in HCV patients receiving medical treatments for other concomitant diseases (Crabbe et al. 2009). CsA is also known to have highly variable pharmacokinetics, with early formulations showing oral bioavailability from 1-89% (Kapurtzak et al., 2004). Without expensive monitoring of patient blood levels, this can lead to increased prevalence of side effects due to increased plasma levels, or reduced clinical response due to lowered plasma levels.

Considering that inhibition of cyclophilins represent a promising new approach for treatment of HCV, there is a need for discovery and development of more potent and safer CyP inhibitors for use in combination therapy against HCV infection.

Sanglifehrins

Sanglifehrin A (SfA) and its natural congeners belong to a class of mixed non-ribosomal peptide/polyketides, produced by *Streptomyces* sp. A92-308110 (also known as DSM 9954) (see WO 97/02285), which were originally discovered on the basis of their high affinity to cyclophilin A (CyPA). SfA is the most abundant component in fermentation broths and exhibits approximately 20-fold higher affinity for CyPA compared to CsA. This has led to the suggestion that sanglifehrins could be useful for the treatment of HCV (WO2006/138507). Sanglifehrins have also been shown to exhibit a lower immunosuppressive activity than CsA when tested in vitro (Sanglier et al., 1999; Fehr et al., 1999). SfA binds with high affinity to the CsA binding site of CyPA (Kallen et al., 2005).

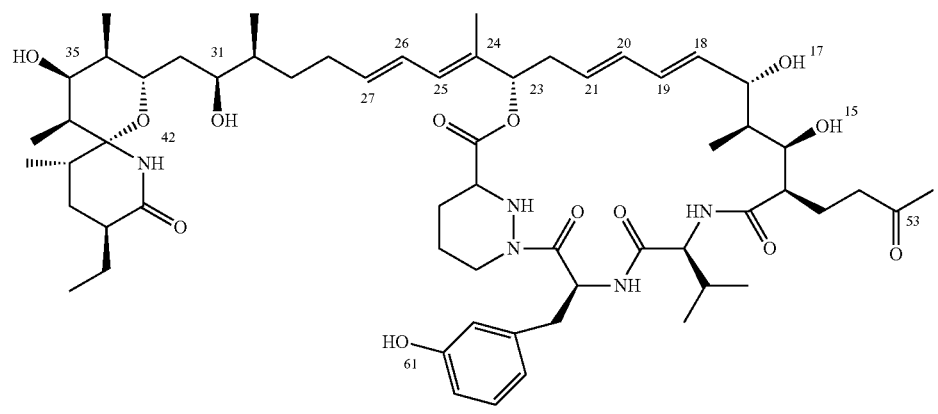

sanglifehrin A, 5

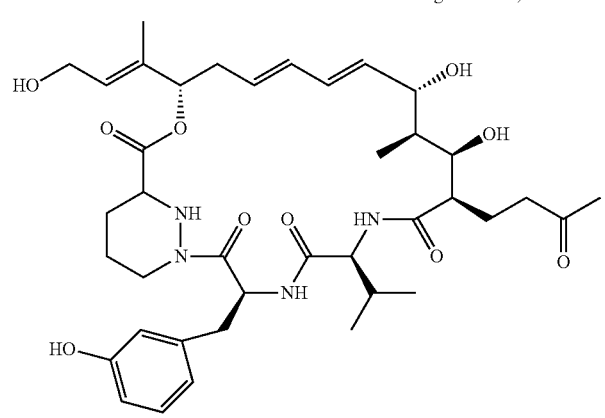

hydroxymacrocycle, 6

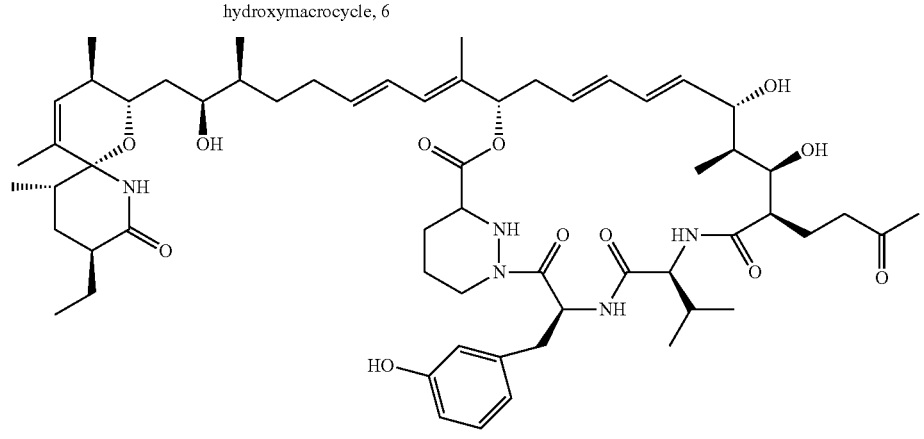

sanglifehrin B, 7

Biosynthesis of Sanglifehrins

Sanglifehrins are biosynthesised by a mixed polyketide synthase (PKS)/Non-ribosomal peptide synthetase (NRPS) (see WO2010/034243). The 22-membered macrolide backbone consists of a polyketide carbon chain and a tripeptide chain. The peptide chain consists of one natural amino acid, valine, and two non-natural amino acids: (S)-meta-tyrosine and (S)-piperazic acid, linked by an amide bond. Hydroxylation of phenylalanine (either in situ on the NRPS or prior to biosynthesis) to generate (S)-meta-tyrosine is thought to occur via the gene product of sfaA.

Immunosuppressive Action of Sanglifehrins

The immunosuppressive mechanism of action of SfA is different to that of other known immunophilin-binding immunosuppressive drugs such as CsA, FK506 and rapamycin. SfA does not inhibit the phosphatase activity of calcineurin, the target of CsA (Zenke et al. 2001), instead its immunosuppressive activity has been attributed to the inhibition of interleukin-6 (Hartel et al., 2005), interleukin-12 (Steinschulte et al., 2003) and inhibition of interleukin-2-dependent T cell proliferation (Zhang & Liu, 2001). However, the molecular target and mechanism through which SfA exerts its immunosuppressive effect is hitherto unknown.

The molecular structure of SfA is complex and its interaction with CyPA is thought to be mediated largely by the macrocyclic portion of the molecule. In fact, a macrocyclic compound (hydroxymacrocycle) derived from oxidative cleavage of SfA has shown strong affinity for CyPA (Sedrani et al., 2003). X-ray crystal structure data has shown that the hydroxymacrocycle binds to the same active site of CyPA as CsA. Analogues based on the macrocycle moiety of SfA have also previously been shown to be devoid of immunosuppressive properties (Sedrani et al., 2003), providing opportunity for design of non-immunosuppressive CyP inhibitors for potential use in HCV therapy.

Converse to this, there is also an opportunity to develop immunosuppressive agents with low toxicity for use in such areas as prophylaxis of transplant rejection, autoimmune, inflammatory and respiratory disorders, including, but not limited to, Crohn's disease, Behcet syndrome, uveitis, psoriasis, atopic dermatitis, rheumatoid arthritis, nephritic syndrome, aplastic anaemia, biliary cirrhosis, asthma, pulmonary fibrosis, chronic obstructive pulmonary disease (COPD) and celiac disease. Sanglifehrins have been shown to have a novel mechanism of immunosuppressive activity (Zenke et al., 2001), potentially acting through dendritic cell chemokines (Immecke et al., 2011), and there is therefore an opportunity to develop agents with a mechanism of action different to current clinical agents, such as cyclosporine A, rapamycin and FK506. Sanglifehrin A has been shown to be 10 fold less potent than Cyclosporine A, so the ideal novel agent would have improved potency and/or therapeutic window.

Other Therapeutic Uses of Cyclophilin Inhibitors

Human Immunodeficiency Virus (HIV)

Cyclophilin inhibitors, such as CsA and DEBIO-025 have also shown potential utility in inhibition of HIV replication. The cyclophilin inhibitors are thought to interfere with function of CyPA during progression/completion of HIV reverse transcription (Ptak et al., 2008). However, when tested clinically, DEBIO-025 only reduced HIV-1 RNA levels and >1 log 10 copies/mL in nine and two patients respectively, whilst 27 of the treated patients showed no reduction in HIV-1 RNA levels (Steyn et al., 2006). Following this, DEBIO-025 was trialled in HCV/HIV coinfected patients, and showed better efficacy against HCV, and the HIV clinical trials were discontinued (see Watashi et al., 2010).

Treatment of HIV

More than 30 million people are infected by HIV-1 worldwide, with 3 million new cases each year. Treatment options have improved dramatically with the introduction of highly active antiretroviral therapy (HAART) (Schopman et al., 2010), By 2008, nearly 25 antiretroviral drugs had been licensed for treatment of HIV-1, including nine nucleoside reverse transcriptase inhibitors (NRTI), four non-nucleoside reverse transcriptase inhibitors (NNRTI), nine protease inhibitors (PI), one fusion inhibitor, one CCR5 inhibitor and one integrase inhibitor (Shafer and Schapiro, 2008). However, none of these current regimens leads to complete viral clearance, they can lead to severe side effects and antiviral resistance is still a major concern. Therefore, there still remains a need for new antiviral therapies, especially in mechanism of action classes where there are no approved drugs, such as is the case for cyclophilin inhibitors.

Hepatitis B Virus

Hepatitis B is a DNA virus of the family hepadnaviridae, and is the causative agent of Hepatitis B. As opposed to the cases with HCV and HIV, there have been very few published accounts of activity of cyclophilin inhibitors against Hepatitis B virus. Ptak et al. 2008 have described weak activity of Debio-025 against HBV (IC50 of 4.1 µM), whilst Xie et al., 2007 described some activity of CsA against HBV (IC50>1.3 µg/mL). This is in contrast to HIV and HCV, where there are numerous reports of nanomolar antiviral activity of cyclophilin inhibitors.

Treatment of HBV

HBV infects up to 400 million people worldwide and is a major cause of chronic viral hepatitis and hepatocellular carcinoma. As of 2008, there were six drugs licensed for the treatment of HBV; interferon alpha and pegylated interferon alpha, three nucleoside analogues (lamivudine, entecavir and telbivudine) and one nucleotide analogue (adefovir dipivoxil). However, due to high rates of resistance, poor tolerability and possible side effects, new therapeutic options are needed (Ferir et al., 2008).

Inhibition of the Mitochondrial Permeability Transition Pore (mPTP)

Opening of the high conductance permeability transition pores in mitochondria initiates onset of the mitochondrial permeability transition (MPT). This is a causative event, leading to necrosis and apoptosis in hepatocytes after oxidative stress, Ca2+ toxicity, and ischaemia/reperfusion. Inhibition of Cyclophilin D (also known as Cyclophilin F) by cyclophilin inhibitors has been shown to block opening of permeability transition pores and protects cell death after these stresses. Cyclophilin D inhibitors may therefore be useful in indications where the mPTP opening has been implicated, such as muscular dystrophy, in particular Ullrich congenital muscular dystrophy and Bethlem myopathy (Millay et al., 2008, WO2008/084368, Palma et al., 2009), multiple sclerosis (Forte et al., 2009), diabetes (Fujimoto et al., 2010), amyotrophic lateral sclerosis (Martin 2009), bipolar disorder (Kubota et al., 2010), Alzheimer's disease (Du and Yan, 2010), Huntington's disease (Perry et al., 2010), recovery after myocardial infarction (Gomez et al., 2007) and chronic alchohol consumption (King et al., 2010).

Further Therapeutic Uses

Cyclophilin inhibitors have potential activity against and therefore in the treatment of infections of other viruses, such as Varicella-zoster virus (Ptak et al., 2008), Influenza A virus (Liu et al., 2009), Severe acute respiratory syndrome coronavirus and other human and feline coronaviruses (Chen et al., 2005, Ptak et al., 2008), Dengue virus (Kaul et al., 2009), Yellow fever virus (Qing et al., 2009), West Nile virus (Qing et al., 2009), Western equine encephalitis virus (Qing et al., 2009), Cytomegalovirus (Kawasaki et al., 2007) and Vaccinia virus (Castro et al., 2003).

There are also reports of utility of cyclophilin inhibitors and cyclophilin inhibition in other therapeutic areas, such as in cancer (Han et al., 2009).

General Comments on Sanglifehrins

One of the issues in drug development of compounds such as sanglifehrins is rapid metabolism and glucuronidation, leading to low oral bioavailability. This can lead to an increased chance of food effect, more frequent incomplete release from the dosage form and higher interpatient variability.

Therefore there remains a need to identify novel cyclophilin inhibitors, which may have utility, particularly in the treatment of HCV infection, but also in the treatment of other disease areas where inhibition of cyclophilins may be useful, such as HIV infection, Muscular Dystrophy or aiding recovery after myocardial infarction or where immunosuppression or anti-inflammatory effect is useful. Preferably, such cyclophilin inhibitors have improved properties over the currently available cyclophilin inhibitors, including one or more of the following properties: longer half-life or increased oral bioavailability, possibly via reduced P450 metabolism and/or reduced glucuronidation, improved water solubility, improved potency against HCV, reduced toxicity (including hepatotoxicity), improved pharmacological profile, such as high exposure to target organ (e.g. liver in the case of HCV) and/or long half life (enabling less frequent dosing), reduced drug-drug interactions, such as via reduced levels of CYP3A4 metabolism and inhibition and reduced (Pgp) inhibition (enabling easier multi-drug combinations) and improved side-effect profile, such as low binding to MRP2, leading to a reduced chance of hyperbilirubinaemia, lower immunosuppressive effect, improved activity against resistant virus species, in particular CsA and CsA analogue (e.g DEBIO-025) resistant virus species and higher therapeutic (and/or selectivity) index. The present invention discloses novel sanglifehrin analogues which may have one or more of the above properties. In particular, the present invention discloses novel mutasynthetic sanglifehrin analogues, which are anticipated to have reduced metabolism via P450 or glucuronidation, for example as shown by increased microsome half-life and/or reduced improved potency against HCV, for example as shown by a low replicon $EC_{50}$.

In addition, there is also a need to develop novel immunosuppressive agents, which may have utility in the prophylaxis of transplant rejection, or in the treatment of autoimmune, inflammatory and respiratory disorders. Preferably, such immunosuppressants have improved properties over the known natural sanglifehrins, including one or more of the following properties: longer half-life or increased oral bioavailability, possibly via reduced P450 metabolism and/or reduced glucuronidation, improved water solubility, improved potency in immunosuppressive activity, such as might be seen in T-cell proliferation assays, reduced toxicity (including hepatotoxicity), improved pharmacological profile, such as high exposure to target organ and/or long half-life (enabling less frequent dosing), reduced drug-drug interactions, such as via reduced levels of CYP3A4 metabolism and inhibition and reduced (Pgp) inhibition (enabling easier multi-drug combinations) and improved side-effect profile. The present invention discloses novel sanglifehrin analogues which may have one or more of the above properties. In particular, the present invention discloses novel derivatives, which have reduced metabolism via P450 or glucuronidation, for example as shown by increased microsome half-life and/or improved immunosuppressive potency, for example as shown by a low t-cell proliferation $IC_{50}$.

Thus, as can be seen from the Examples, the compounds of the invention have the following favourable therapeutically relevant properties:

improved antiviral potency against HCV and HIV as compared with the prior art cyclophilin inhibitors Cyclosporin A, DEBIO-025 (alisporivir) and Sanglifehrin A;

reduced clearance and increased oral expose as compared with the prior art compound Sanglifehrin A;

more potent inhibition of CypA PPlase activity as compared with the prior art cyclophilin inhibitors Cyclosporin A, DEBIO-025 (alisporivir) and Sanglifehrin A;

improved side effect profile and reduced drug-drug interactions as demonstrated by reduced inhibition of bilirubin transporters (OATP-1B1, OATP-1B3, MRP2 and MRP3) and reduced inhibition of xenobiotic transporters (Pgp and BSEP).

SUMMARY OF THE INVENTION

The present invention provides novel macrocyclic sanglifehrin analogues, which have been generated by semisynthetic modification of mutasynthetic sanglifehrins. These analogues may be generated by dihydroxylation of a mutasynthetic sanglifehrin, such as described in formula IIA and formula IIB, followed by cleavage to generate the aldehydic macrocycle, followed by further chemistry, including Horner-Emmons type reactions and other coupling reactions involving an aldehyde, to generate molecules with a variety of substituents to replace the aldehyde. As a result, the present invention provides macrocyclic sanglifehrin analogues, methods for the preparation of these compounds, and methods for the use of these compounds in medicine or as intermediates in the production of further compounds.

Therefore, in a first aspect, the present invention provides macrocyclic sanglifehrin analogues and derivatives thereof according to formula (I) below, or a pharmaceutically acceptable salt thereof:

Formula (I)

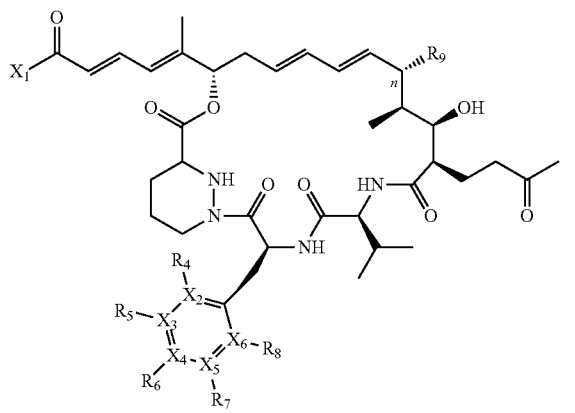

wherein:
the moiety $X_1$ represents $-OR_1$, $-NR_1R_2$ or $R_3$;
$R_1$, $R_2$ and $R_3$ independently represent hydrogen, alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
and wherein one or more carbon atoms of $R_1$, $R_2$ and $R_3$ not being part of an aryl or heteroaryl group are optionally replaced by a heteroatom selected from O, N and $S(O)_p$ in which p represents 0, 1 or 2 and wherein one or more carbon atoms of $R_1$, $R_2$ and $R_3$ are optionally replaced by carbonyl;
or $R_1$ and $R_2$ are linked such that $NR_1R_2$ represents a saturated or unsaturated heterocyclic ring containing the specified nitrogen atom and wherein one or more carbon atoms of said ring are optionally replaced by a further heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;
and wherein one or more carbon atoms of an $R_1$, $R_2$ and $R_3$ group may optionally be substituted by one or more halogen atoms;
or $R_1$ and/or $R_2$ represents hydrogen;
$R_9$ represents H or OH;
n represents a single or double bond, save that when n represents a double bond $R_9$ represents H;
$R_4$, $R_5$, $R_6$, $R_7$ and $R_8$ independently represent H, F, Cl, Br, alkenyl or alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms;
$X_2$, $X_3$, $X_4$, $X_5$ and $X_6$ independently represent C or N, and in the case of any of these groups representing N the attached substituent is absent;
with the proviso that where $R_4$, $R_6$, $R_7$ and $R_8$ all represent H and $X_2$, $X_3$, $X_4$, $X_5$ and $X_6$ all represent C, then $R_5$ cannot represent OH, —Oalkyl or —O(CO)alkyl;
including any tautomer thereof; and including a methanol adduct thereof in which a ketal is formed by the combination of the C-53 keto and the C-15 hydroxyl group and methanol.

The above structure shows a representative tautomer and the invention embraces all tautomers of the compounds of formula (I) for example keto compounds where enol compounds are illustrated and vice versa.

Specific tautomers that are included within the definition of formula (I) are those in which (i) the C-53 keto group forms a hemiketal with the C-15 hydroxyl, or (ii) the C-15 and C-17 hydroxyl can combine with the C-53 keto to form a ketal. All numberings use the system for the parent sanglifehrin A structure.

The compounds of formula (I), or pharmaceutically acceptable salts thereof, may optionally be present in the form of pharmaceutically acceptable solvates, such as a hydrate.

DEFINITIONS

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "sanglifehrin(s)" refers to chemical compounds that are structurally similar to sanglifehrin A but which differ slightly in composition (as in the replacement of one atom by another or in the presence or absence of a particular functional group), in particular those generated by fermentation of Streptomyces sp. A92-308110. Examples include the sanglifehrin-like compounds discussed in WO97/02285 and WO98/07743, such as sanglifehrin B.

As used herein the term "mutasynthetic sanglifehrin(s)" or "mutasynthetic sanglifehrin analogue(s)" refers to chemical compounds that are structurally similar to sanglifehrin A, B, C or D but which differ slightly in composition (as in the replacement of one or more atom by another or in the presence or absence of a particular functional group), in particular, those generated by fermentation of Streptomyces sp. A92-308110 or a mutant thereof, where the culture is fed with a meta-tyrosine analogue.

As used herein the term "meta-tyrosine analogue(s)" refers to chemical compounds that are structurally similar to meta-tyrosine but which differ slightly in composition (as in the replacement of one or more atom by another or in the presence or absence of a particular functional group), in particular, those described in formula (III).

As used herein, the term "macrocyclic analogue", "macrocyclic sanglifehrin analogue" or "macrocyclic sanglifehrin", refers to a compound referred to above as representing the invention in its broadest aspect, for example a compound according to formula (I) above, or a pharmaceutically acceptable salt thereof. These compounds are also referred to as "compounds of the invention" or "derivatives of sanglifehrin" or "sanglifehrin analogues" and these terms are used interchangeably in the present application.

As used herein, the term "HCV" refers to Hepatitis C Virus, a single stranded, RNA, enveloped virus in the viral family Flaviviridae.

As used herein, the term "HIV" refers to Human Immunodeficiency Virus, the causative agent of Human Acquired Immune Deficiency Syndrome.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Egorin et al. 2002).

The term "water solubility" as used in this application refers to solubility in aqueous media, e.g. phosphate buffered saline (PBS) at pH 7.4, or in 5% glucose solution. Tests for water solubility are given below in the Examples as "water solubility assay".

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Hydrochloric acid salts are of particular interest. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts.

As used herein, the term "alkyl" represents a straight chain or branched alkyl group, containing typically 1-10 carbon atoms, for example a $C_{1-6}$ alkyl group. "Alkenyl" refers to an alkyl group containing two or more carbons (for example 2-10 carbons e.g. a $C_{2-6}$ alkenyl group) which is unsaturated with one or more double bonds.

Examples of alkyl groups include $C_{1-4}$ alkyl groups such as methyl, ethyl, n-propyl, i-propyl, and n-butyl. Examples of alkenyl groups include $C_{2-4}$alkenyl groups such as —CH=CH$_2$ and —CH$_2$CH=CH$_2$.

As used herein, the term "cycloalkyl" represents a cyclic alkyl group, containing typically 3-10 carbon atoms, optionally branched, for example cyclobutyl, cyclopentyl, cyclohexyl or cycloheptyl. A branched example is 2-methylcyclopentyl. "Cycloalkenyl" refers to a cyclic alkenyl group containing typically 5-10 carbon atoms, for example cyclopentyl, cyclohexenyl or cycloheptenyl. Cycloalkyl and cycloalkenyl groups may for example be monocyclic or bicyclic (including spirocyclic) but are suitably monocyclic.

As used herein, the term "cycloalkyl" represents a cyclic alkyl group, containing typically 3-10 carbon atoms, optionally branched, for example cyclobutyl, cyclopentyl, cyclohexyl or cycloheptyl. A branched example is 2-methylcyclopentyl. "Cycloalkenyl" refers to a cyclic alkenyl group containing typically 5-10 carbon atoms, for example cyclopentyl, cyclohexenyl or cycloheptenyl. Cycloalkyl and cycloalkenyl groups may for example be monocyclic or bicyclic (including spirocyclic) but are suitably monocyclic.

As used herein, the term "heterocyclyl" represents a cycloalkyl group in which one or more one or more ring carbon atoms (e.g. 1, 2 or 3 ring carbon atoms such as 1 or 2 e.g. 1) are replaced by heteroatoms selected from O, N and S. Examples include morpholinyl, piperidinyl, pyrrolidinyl, piperazinyl and N-methyl piperazinyl.

As used herein, the term "heterocyclenyl" represents a cycloalkenyl group in which one or more one or more ring carbon atoms (e.g. 1, 2 or 3 ring carbon atoms such as 1 or 2 e.g. 1) are replaced by heteroatoms selected from O, N and S.

Examples of aryl groups include (except where indicated) monocyclic groups i.e. phenyl and bicyclic rings (e.g. 9 and 10 membered rings) which are aromatic or (in the case of bicyclic rings contain at least one aromatic ring). For example a bicyclic ring may be fully aromatic e.g. naphthyl or may be partially aromatic (e.g. containing one aromatic ring), such as tetraline, indene or indane. Preferred aryl is phenyl. Aryl groups may optionally be substituted e.g. with one or more (e.g. 1, 2 or 3) substituents e.g. selected from alkyl (eg $C_{1-4}$alkyl), hydroxyl, $CF_3$, halogen, alkoxy (e.g. $C_{1-4}$alkoxy), nitro, —SO$_2$Me, cyano and —CONH$_2$.

Examples of heteroaryl groups include (except where indicated) monocyclic groups (e.g. 5 and 6 membered rings) and bicyclic rings (e.g. 9 and 10 membered rings) which are aromatic or (in the case of bicyclic rings contain at least one aromatic ring) and contain one or more heteroatoms (e.g. 1, 2, 3 or 4) heteroatoms selected from N, O and S. Examples of 5 membered heteroaryl rings include pyrrole, furan, thiophene, oxazole, oxadiazole, thiazole and triazole. Examples of 6 membered heteroaryl rings include pyridine, pyrimidine and pyrazine. Examples of bicyclic rings include fully aromatic rings such as quinoline, quinazoline, isoquinoline, indole, cinnoline, benzthiazole, benzimidazole, purine and quinoxaline and partially aromatic rings such as chromene, chromane, tetrahydroquinoline, dihydroquinoline, isoindoline and indoline. Monocyclic heteroaryl groups are preferred. The aforementioned heteroaryl groups may be optionally substituted as described above for aryl groups.

When bicyclic aryl and heteroaryl groups are partially aromatic, the connection to the remainder of the molecule may be through the aromatic portion or through the non-aromatic portion.

The term "treatment" includes prophylactic as well as therapeutic treatment.

The term "formula II" refers to formula IIA and formula IIB collectively.

FIGURE LEGEND

Figure 2:
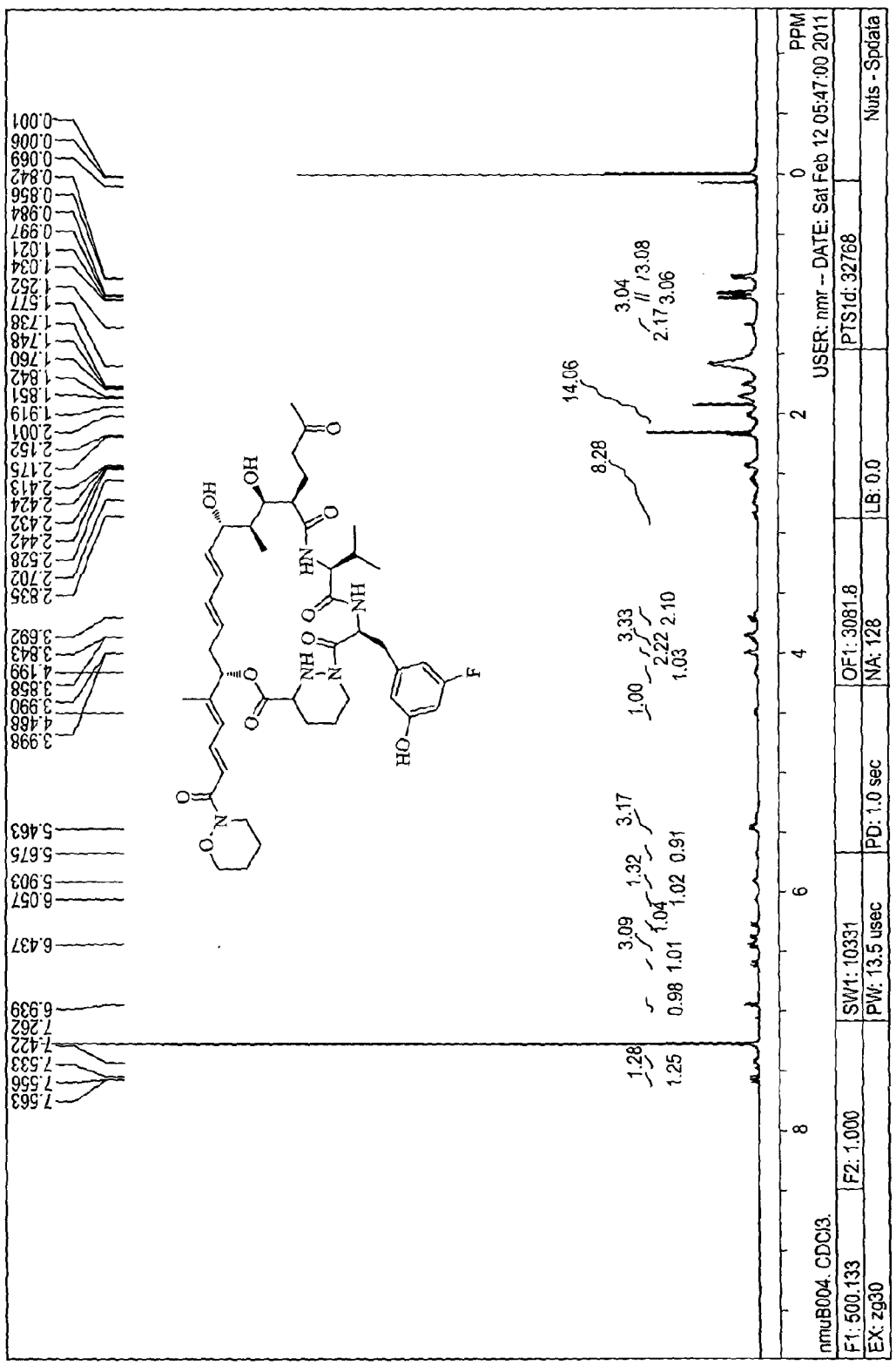
Figure 3:
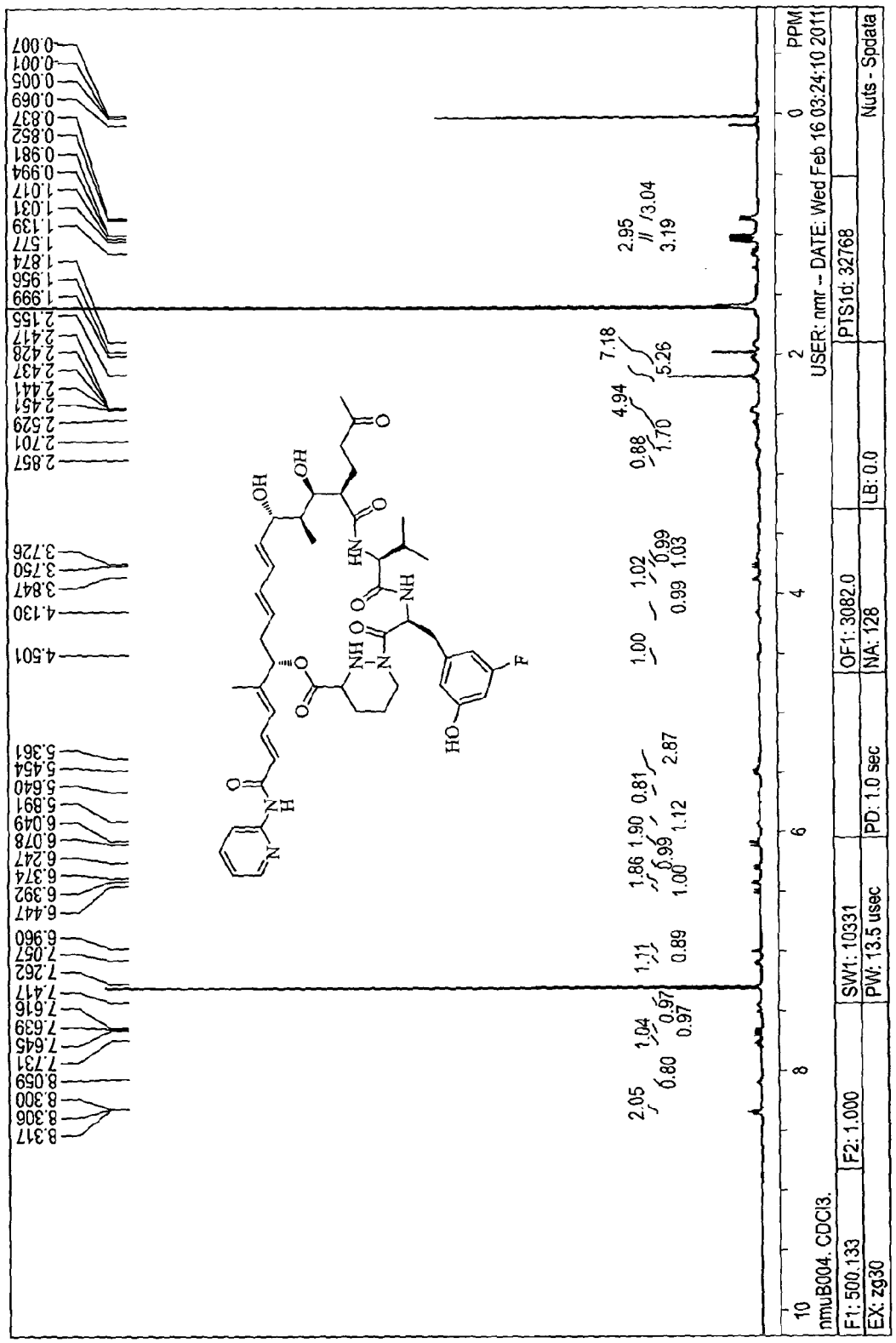
Figure 4:
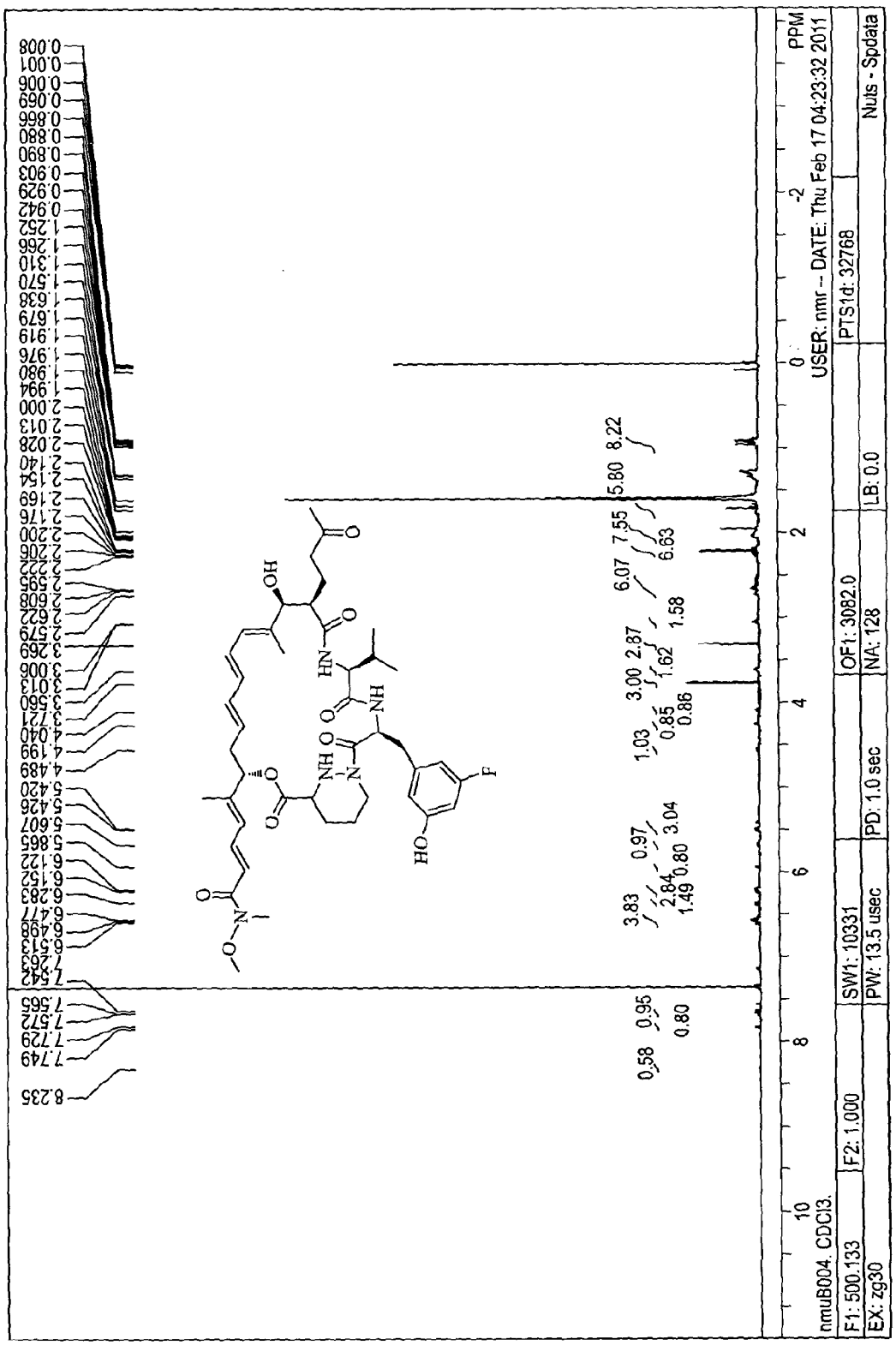
Figure 5:
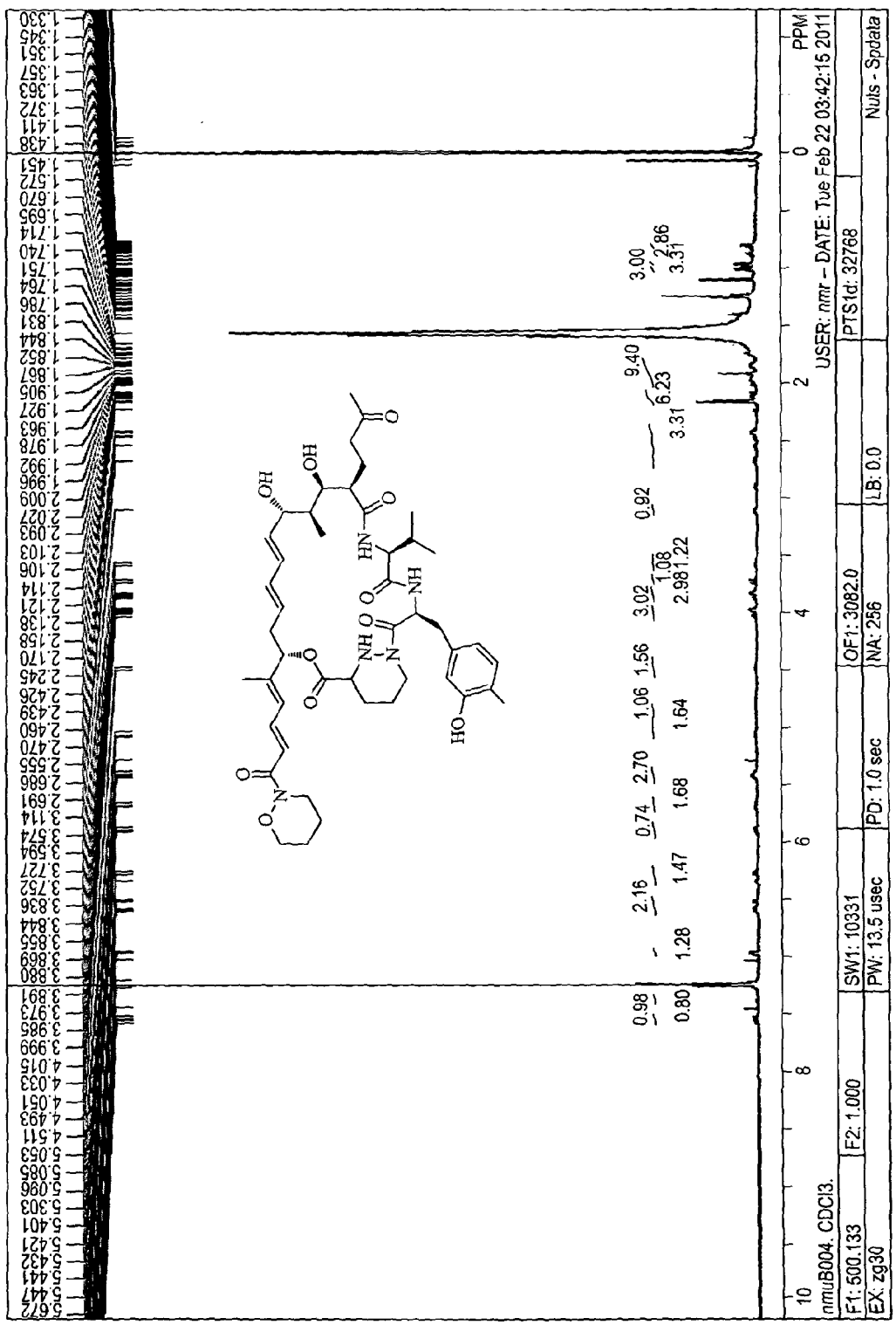
Figure 6:
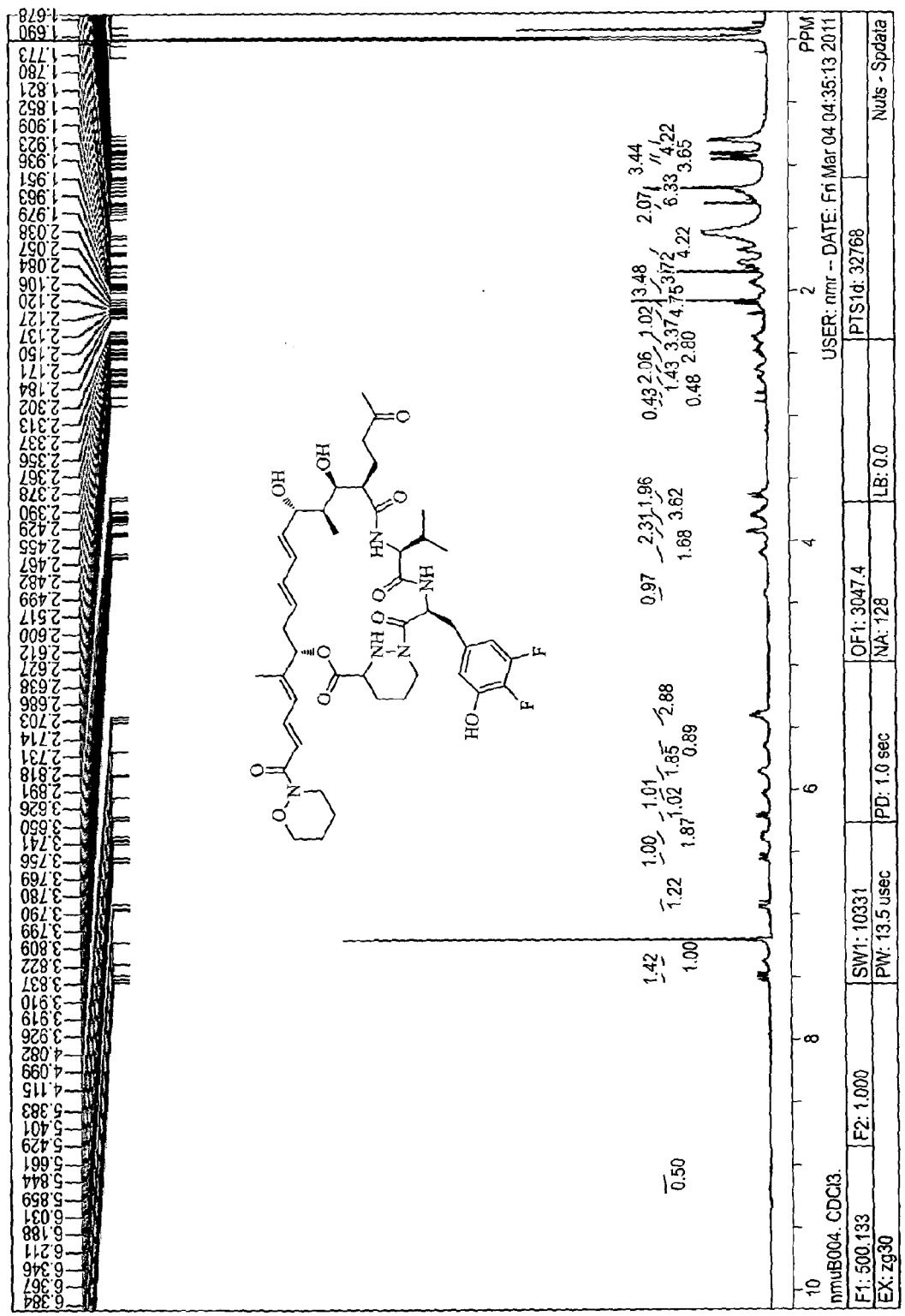
Figure 7:
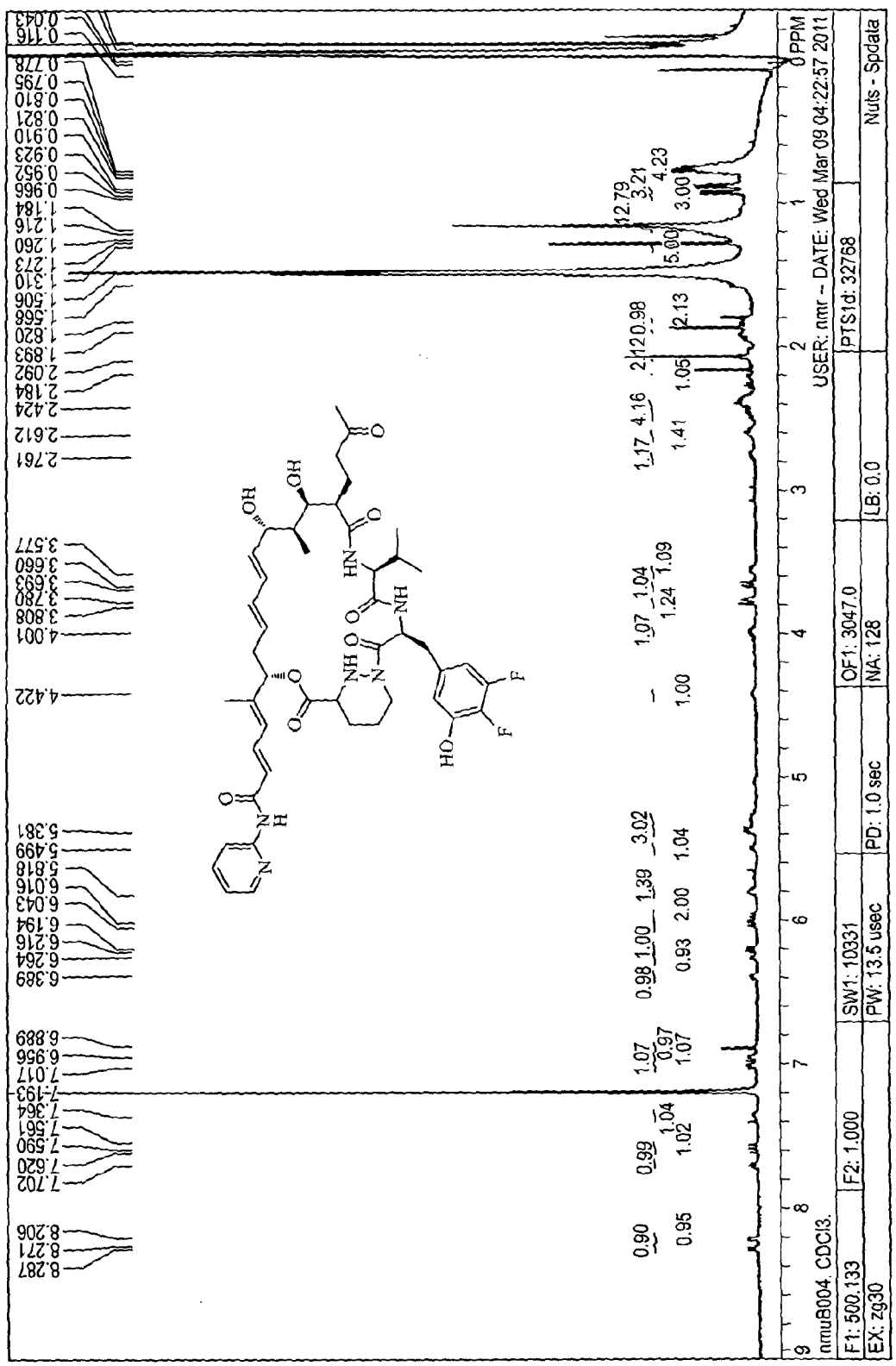
Figure 8:
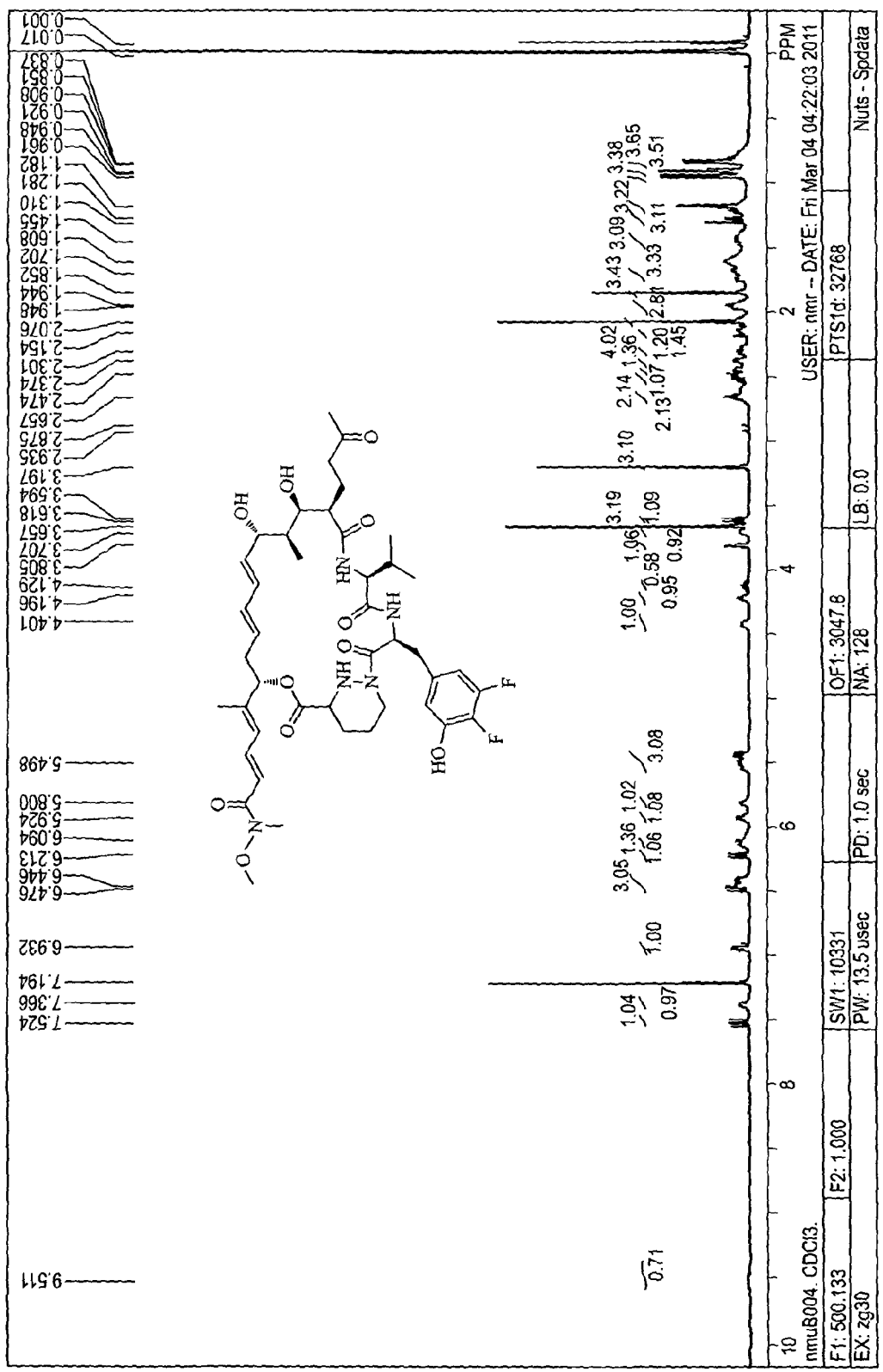

FIG. 1: $^1$H NMR of compound 23
FIG. 2: $^1$H NMR of compound 24
FIG. 3: $^1$H NMR of compound 25
FIG. 4: $^1$H NMR of compound 26
FIG. 5: $^1$H NMR of compound 27
FIG. 6: $^1$H NMR of compound 28
FIG. 7: $^1$H NMR of compound 29
FIG. 8: $^1$H NMR of compound 30

DESCRIPTION OF THE INVENTION

The present invention provides macrocyclic sanglifehrin analogues, as set out above, methods for preparation of these compounds and methods for the use of these compounds in medicine.

In one embodiment, the compound is a methanol adduct thereof in which a hemi-ketal is formed by the combination of the C-53 keto and the C-15 hydroxyl groups and methanol. In another embodiment it is not.

Variables n, $X_2$-$X_6$ and $R_4$-$R_9$

Suitably n represents a single bond.

Suitably $R_9$ represents OH.

Suitably $R_4$, $R_5$, $R_6$, $R_7$ and $R_8$ independently represent H, F, Cl, Br, $C_{2-6}$alkenyl or $C_{1-10}$alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms.

In certain embodiments a carbon atom of the $C_{1-10}$alkyl group (e.g. $C_{1-6}$alkyl group) that one or more of $R_4$, $R_5$, $R_6$, $R_7$ and $R_8$ may represent is replaced by a heteroatom.

If —$CH_3$ is replaced by N, the group formed is —$NH_2$. If —$CH_2$— is replaced by N, the group formed is —NH—. If —CHR— is replaced by N the group formed is —NR—. Hence nitrogen atoms within the $R_4$, $R_5$, $R_6$, $R_7$ or $R_8$ group may be primary, secondary or tertiary nitrogen atoms.

If —$CH_3$ is replaced by 0, the group formed is —OH.

When a carbon atom of the $C_{1-10}$alkyl group (e.g. $C_{1-6}$alkyl group) that one or more of $R_4$, $R_5$, $R_6$, $R_7$ and $R_8$ may represent is replaced by a heteroatom, it is suitably replaced by O, S or N, especially N or O particularly 0.

When any one of $R_4$, $R_5$, $R_6$, $R_7$ and $R_8$ contains a group $S(O)_p$, variable p suitably represents 0 or 1. In one embodiment p represents 0. In another embodiment p represents 1. In another embodiment p represents 2.

When a $C_{1-10}$alkyl group (e.g. $C_{1-6}$alkyl group) that one or more of $R_4$, $R_5$, $R_6$, $R_7$ and $R_8$ may represent contains more than one heteroatom, these may typically be separated by two or more carbon atoms.

Suitably, the carbon atoms of a $C_{1-10}$alkyl group (e.g. $C_{1-6}$alkyl group) that one or more of $R_4$, $R_5$, $R_6$, $R_7$ and $R_8$ may represent are not replaced by any heteroatom.

When a carbon atom of the $C_{1-10}$alkyl group (e.g. $C_{1-6}$alkyl group) that one or more of $R_4$, $R_5$, $R_6$, $R_7$ and $R_8$ may represent is replaced by a carbonyl, the carbonyl is suitably located adjacent to another carbon atom or a nitrogen atom. Suitably carbonyl groups are not located adjacent to sulfur or oxygen atoms.

For example one or more of $R_4$, $R_5$, $R_6$, $R_7$ and $R_8$ may represent —$COC_{1-3}$alkyl e.g. —COMe.

Suitably the carbon atoms of the $C_{1-10}$alkyl group (e.g. $C_{1-6}$alkyl group) that one or more of $R_4$, $R_5$, $R_6$, $R_7$ and $R_8$ may represent are not replaced by a carbonyl.

The $C_{1-10}$alkyl group (e.g. $C_{1-6}$alkyl group) that one or more of $R_4$, $R_5$, $R_6$, $R_7$ and $R_8$ may represent may be substituted by one or more halogen atoms. For example one or more of $R_1$, $R_2$, $R_3$, $R_4$ and $R_5$ may represent —$CF_3$. Alternatively one or more of $R_4$, $R_5$, $R_6$, $R_7$ and $R_8$ may represent $C_{1-10}$alkyl (e.g. $C_{1-6}$alkyl) substituted by one or more (eg one) Cl or F atom (eg —$CH_2CH_2$Cl).

Suitably the $C_{1-10}$alkyl groups (e.g. $C_{1-6}$alkyl groups) that $R_4$, $R_5$, $R_6$, $R_7$ and $R_8$ may represent are not substituted by halogen.

When one or more of $R_4$, $R_5$, $R_6$, $R_7$ and $R_8$ group(s) represent a $C_{1-10}$alkyl group (e.g. $C_{1-6}$alkyl group) suitably the group(s) represent $C_{1-4}$ alkyl (e.g. $C_{1-2}$ alkyl such as methyl).

In an embodiment, one or more of $R_4$, $R_5$, $R_6$, $R_7$ and $R_8$ represent $C_{1-6}$alkyl (such as $C_{1-2}$ alkyl) or $C_{2-3}$alkenyl e.g. one or more of $R_4$, $R_5$, $R_6$, $R_7$ and $R_8$ represent methyl.

Suitably $R_4$ represents H, F, Cl, $CF_3$, OH or $C_{1-6}$alkyl (e.g. methyl). Most suitably, $R_4$ represents H or F, especially H.

Suitably $R_5$ represents H, F, Cl, $CF_3$, OH, $NH_2$ or $C_{1-6}$alkyl (e.g. methyl). More suitably, $R_5$ represents H, F, OH or $NH_2$, especially OH.

Suitably $R_6$ represents H, F, Cl, $CF_3$, OH or $C_{1-6}$alkyl (e.g. methyl). More suitably, $R_6$ represents H, Me or F.

Suitably $R_7$ represents H, F, Cl, $CF_3$, OH or $C_{1-6}$alkyl (e.g. methyl). More suitably, $R_7$ represents H or F.

Suitably $R_8$ represents H, F, Cl, $CF_3$, OH or $C_{1-6}$alkyl (e.g. methyl). More suitably, $R_8$ represents H or F especially H.

Suitably one or more, more suitably two or more (for example three or more) of $R_4$, $R_5$, $R_6$, $R_7$ and $R_8$ do not represent H.

Suitably one or more, for example two or more of $R_4$, $R_5$, $R_6$, $R_7$ and $R_8$ represent F.

Suitably $R_6$ and/or $R_7$ represents F.

Suitably at least two of $X_2$, $X_3$, $X_4$, $X_5$ and $X_6$ represent C; more suitably at least three, more suitably at least four and most suitably all five represent C.

In one embodiment $X_2$ represents N (therefore $R_4$ is absent). In another more preferable embodiment $X_2$ represents C.

Suitably $X_3$ represents C.

Suitably $X_4$ represents C. Suitably $X_5$ represents C.

Suitably $X_6$ represents C.

In an embodiment, $X_2$, $X_3$, $X_4$, $X_5$ and $X_6$ each represents C, $R_4$ represents H, $R_5$ represents OH, $R_6$ represents H, $R_7$ represents F and $R_8$ represents H.

In an embodiment, $X_2$, $X_3$, $X_4$, $X_5$ and $X_6$ each represents C, $R_4$ represents H, $R_5$ represents OH, $R_6$ represents Me, $R_7$ represents H and $R_8$ represents H.

In an embodiment, $X_2$, $X_3$, $X_4$, $X_5$ and $X_6$ each represents C, $R_4$ represents H, $R_5$ represents OH, $R_6$ represents F, $R_7$ represents F and $R_8$ represents H.

Variable $X_1$

In one embodiment $X_1$ represents —$R_3$. In one embodiment $X_1$ represents —$NR_1R_2$. In one embodiment $X_1$ represents —$OR_1$.

In certain embodiments, a carbon atom of $R_1$ and/or $R_2$ and/or $R_3$ is replaced by a heteroatom.

If —$CH_3$ is replaced by N, the group formed is —$NH_2$. If —$CH_2$— is replaced by N, the group formed is —NH—. If —CHR— is replaced by N the group formed is —NR—. Hence nitrogen atoms within the $R_1$, $R_2$, $R_3$ group may be primary, secondary or tertiary nitrogen atoms.

If —$CH_3$ is replaced by O, the group formed is —OH.

When a carbon atom of $R_1$ and/or $R_2$ and/or $R_3$ is replaced by a heteroatom, it is suitably replaced by O or N, especially O.

When a carbon atom of $R_1$ and/or $R_2$ and/or $R_3$ is replaced by a group $S(O)_p$, variable p suitably represents 0 or 1. In one embodiment p represents 0 in another embodiment p represents 1. In another embodiment p represents 2.

When $R_1$ and/or $R_2$ and/or $R_3$ contain more than one heteroatom, these may, for example, be separated by two or more carbon atoms.

Suitably no carbon atoms of $R_1$, $R_2$ and $R_3$ are replaced by heteroatoms.

When a carbon atom of $R_1$ and/or $R_2$ and/or $R_3$ is replaced by a carbonyl, the carbonyl is suitably located adjacent to another carbon atom or a nitrogen atom. Suitably carbonyl groups are not located adjacent to sulfur or oxygen atoms.

For example $R_1$ and/or $R_2$ and/or $R_3$ may represent —$COC_{1-4}$alkyl e.g. —COMe. Suitably a carbon atom of $R_1$ is not replaced by a carbonyl. Suitably a carbon atom of $R_2$ is not replaced by a carbonyl. Suitably a carbon atom of $R_3$ is not replaced by a carbonyl.

When one or more carbon atoms of an $R_1$ and/or $R_2$ and/or $R_3$ group are substituted by one or more halogen atoms, exemplary halogen atoms are F, Cl and Br, especially F and Cl particularly F. An exemplary halogenated $R_1$ and/or $R_2$ and/or $R_3$ moiety is —$CF_3$.

For example, one or more of $R_1$, $R_2$ and $R_3$ may represent $C_{1-10}$alkyl (e.g. $C_{1-6}$alkyl) substituted by one or more (eg one) Cl or F atom (eg —$CH_2CH_2Cl$).

Suitably a carbon atom of $R_1$, $R_2$ and $R_3$ is not substituted by halogen.

When one or more $R_1$, $R_2$ and $R_3$ groups represent a $C_{1-10}$alkyl group (e.g. $C_{1-6}$alkyl group) suitably the groups represent $C_{1-4}$ alkyl (e.g. $C_{1-2}$ alkyl such as methyl).

When $R_1$ and/or $R_2$ and/or $R_3$ represent -alkylaryl, an example includes $C_{1-2}$alkylaryl e.g. benzyl.

When $R_1$ and/or $R_2$ and/or $R_3$ represent -alkenylaryl, an example includes $C_{2-3}$alkenylaryl e.g. -ethenylphenyl.

When $R_1$ and/or $R_2$ and/or $R_3$ represent -alkylheteroaryl, an example includes $C_{1-2}$alkylheteraryl e.g. -methylpyridinyl.

When $R_1$ and/or $R_2$ and/or $R_3$ represent -alkenylheteroaryl, an example includes $C_{2-3}$alkenylheteroaryl e.g. -ethenylpyridinyl.

Suitably $R_1$ does not represent hydrogen.

Suitably $R_1$ and $R_2$ do not both represent hydrogen. Suitably a carbon atom of $R_2$ is not replaced by any heteroatom.

When $X_1$ Represents $NR_1R_2$

When $X_1$ represents $NR_1R_2$, $R_1$ may for example represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl.

$R_2$ may for example represent H, alkyl (e.g. $C_{1-4}$alkyl), alkenyl (e.g. $C_{2-4}$alkenyl), or —Oalkyl (e.g. —$OC_{1-4}$alkyl), especially H or alkyl.

Exemplary $R_1$ groups include aryl or heteroaryl substituted by monocyclic aryl or monocyclic heteroaryl, —$C_{1-4}$alkyl, —$OC_{1-4}$alkyl, —$COC_{1-4}$alkyl or —$C_{2-4}$alkenyl or $R_1$ may represent alkyl or —Oalkyl. The aforementioned exemplary groups may, for example, be taken together $R_2$ representing H or alkyl.

Further exemplary $R_1$ groups include methyl, —$CF_3$, ethyl, isopropyl, —$CH_2CH=CH$, isobutyl, cyclohexyl. The aforementioned exemplary groups may, for example, be taken together with $R_2$ representing H or Me.

Further exemplary $R_1$ groups include optionally substituted pyridinyl or phenyl, for example phenyl substituted by phenyl. The aforementioned exemplary groups may, for example, be taken together with $R_2$ representing H, Me or —OMe.

Further exemplary $R_1$ groups include —OMe, —$OCF_3$, —Oethyl, O-isopropyl, —SMe, O-n-propyl, —O-n-butyl, —O-t-butyl, O-isobutyl, O—$CH_2C(Me)_3$. The aforementioned exemplary groups may, for example, be taken together with $R_2$ representing H, Me. ethyl, isopropyl or tert-butyl.

Further exemplary $R_1$ groups include —O-(optionally substituted phenyl). The aforementioned exemplary groups may, for example, be taken together with $R_2$ representing H, or Me.

Alternatively, $R_1$ and $R_2$ may be linked such that $NR_1R_2$ represents a saturated or unsaturated heterocyclic ring containing the specified nitrogen atom shown.

The heterocyclic ring that $NR_1R_2$ may represent typically contains 4-8 ring atoms, e.g. 5-7 ring atoms, particularly 5 or 6 ring atoms.

The heterocyclic ring that $NR_1R_2$ may, for example, represent typically contains only the nitrogen atom specified (e.g. it represents pyrrolidine or piperidine) or one or two (e.g. one) additional heteroatoms, especially a nitrogen or oxygen atom.

For example, the heterocyclic ring that $NR_1R_2$ may represent may be morpholinyl or 1,2-oxazinane (a six membered saturated ring containing O adjacent to N).

When $NR_1R_2$ represents a saturated or unsaturated heterocyclic ring containing the nitrogen atom specified and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring is fused to an aryl or heteroaryl ring, an example is tetrahydroquinolinyl.

Alternatively, suitably $NR_1R_2$ represents a 5-7 membered heterocyclic ring, such as a pyrrolidine, piperidine, morpholine or piperazine ring in which the 4-nitrogen of piperazine is optionally substituted by $C_{1-4}$alkyl.

In another embodiment, suitably $NR_1R_2$ represents a 5-7 membered heterocyclic ring, such as a pyrrolidine, piperidine, morpholine or piperazine ring in which the 4-nitrogen of piperazine is optionally substituted by $C_{1-4}$alkyl, and in which a carbon atom adjacent to a nitrogen atom within the ring is replaced with carbonyl. Thus, for example, $R_1$ and $R_2$ together with the nitrogen to which they are attached represent piperidinone.

In another embodiment, an oxygen atom is adjacent to the nitrogen atom to which $R_1$ and $R_2$ are attached. For example, $R_1$ may represent alkyl or alkenyl in which the methylene adjacent to the nitrogen atom to which $R_1$ is attached is replaced by O. For example $R_1$ may represent —$OC_{1-4}$alkyl e.g. OMe. Alternatively $R_1$ and $R_2$ are joined and the carbon atom adjacent to the nitrogen atom to which $R_1$ is attached is replaced by O e.g. to form a 1,2-oxazinane ring or a 1,2-isoxazolidine.

In another embodiment, $R_1$ and $R_2$ are linked such that $NR_1R_2$ represents a saturated or unsaturated heterocyclic ring containing the specified nitrogen atom and wherein one or more carbon atoms of said ring are optionally replaced by a further heteroatom selected from O, N and $S(O)_p$ in which p represents 0, 1 or 2 and wherein one or more carbon atoms of said ring are optionally replaced by carbonyl and which heterocyclic ring is fused to an aryl or heteroaryl ring (e.g. is fused to a phenyl or pyridinyl ring).

Exemplary moieties that $NR_1R_2$ may together form include morpholinyl, oxazinane (e.g. 1,2-oxazinane) and those disclosed in the following table:

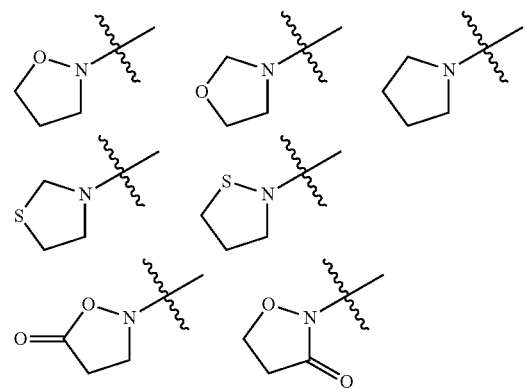

-continued
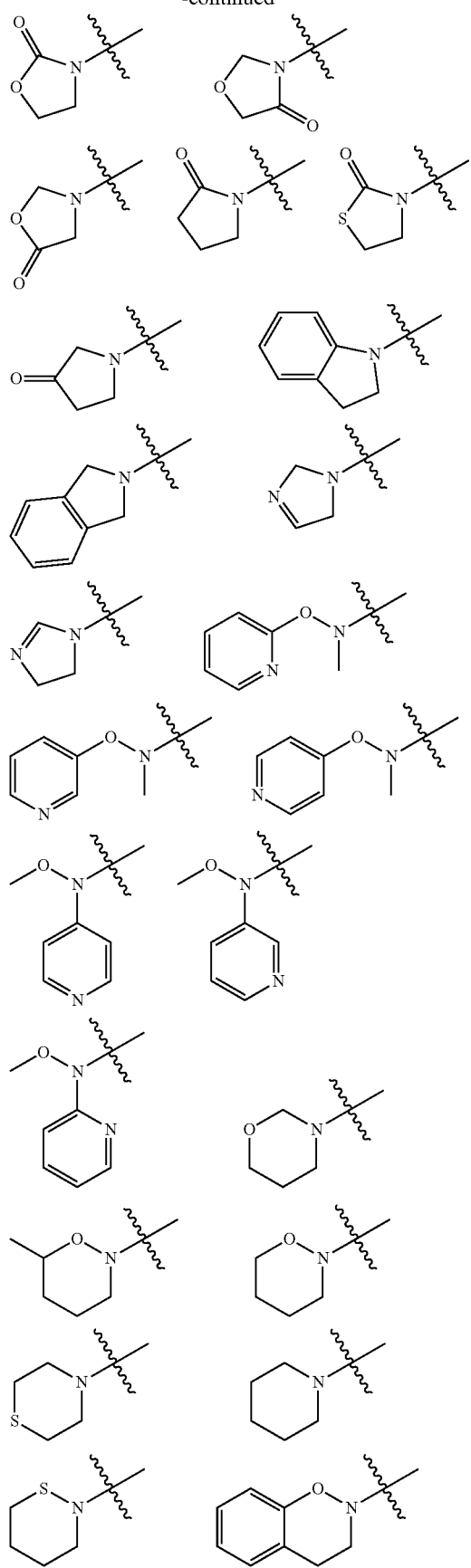
-continued
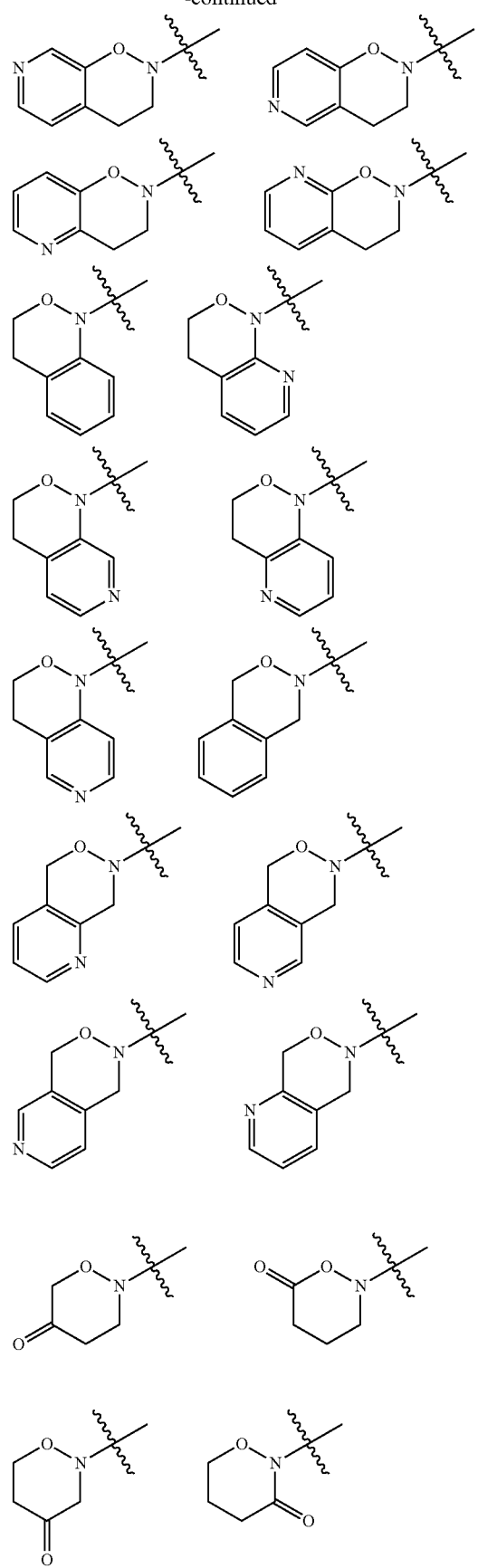

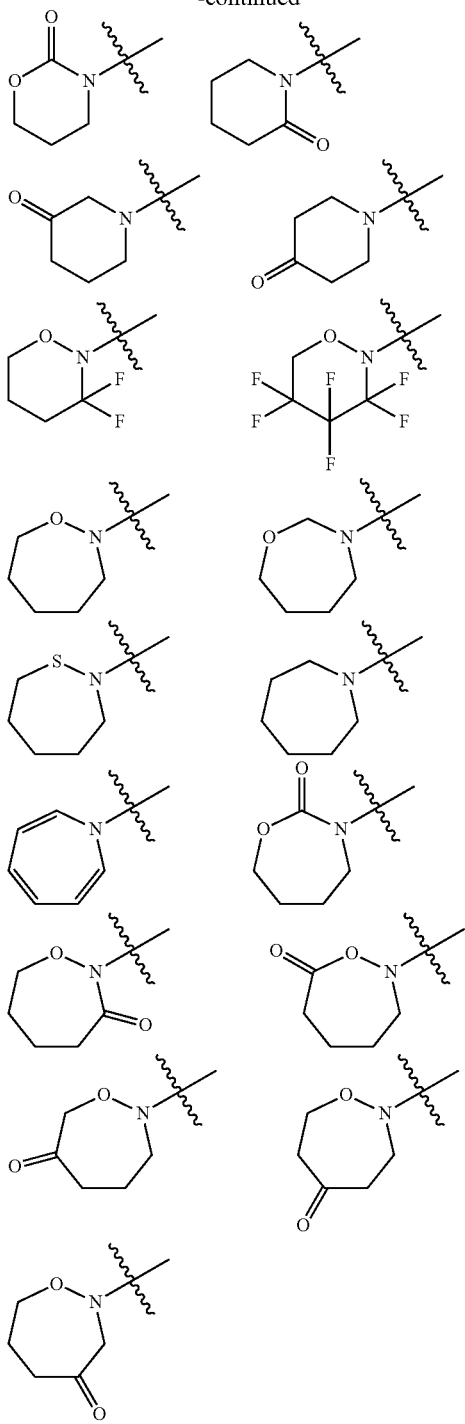

The aforementioned —NR₁R₂ moieties which comprise aryl or heteroaryl groups may also optionally bear on said groups one or more (e.g. one or two, such as one) ring substituents e.g. groups selected from $C_{1-4}$alkyl (e.g. methyl), halogen (e.g. Cl or F), $C_{1-4}$alkoxy (e.g. methoxy), hydroxyl, $CF_3$, cyano, nitro, $SO_2Me$ and $CONH_2$.

The aforementioned —NR₁R₂ moieties may optionally be substituted by one or more (e.g. one or two) halogen (e.g. F or Cl) atoms.

When $X_1$ Represents $OR_1$

When $X_1$ represents $OR_1$, $R_1$ may for example represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl.

In one embodiment $R_1$ represents aryl or heteroaryl optionally substituted by monocyclic aryl or monocyclic heteroaryl. $R_1$ may, for example, represent 4-biphenylyl in which either of the phenyl rings is optionally substituted.

In an embodiment, $R_1$ may represent aryl or heteroaryl substituted by monocyclic aryl or monocyclic heteroaryl, —$C_{1-4}$alkyl, —$OC_{1-4}$alkyl, —$COC_{1-4}$alkyl or —$C_{2-4}$alkenyl.

In an embodiment, $R_1$ represents $C_{1-6}$alkyl (such as $C_{4-6}$ alkyl), $C_{2-6}$alkenyl, $C_{1-4}$alkyl$C_{4-7}$cycloalkyl or $C_{1-4}$alkyl $C_{6-7}$cycloalkenyl.

Suitably $R_1$ is selected from $C_{2-10}$ alkyl (e.g. $C_{2-6}$ alkyl such as $C_{4-6}$ alkyl), $C_{2-10}$ alkenyl (e.g. $C_{2-6}$ alkenyl such as $C_{4-6}$ alkenyl), heteroaryl and aryl.

Thus, in one embodiment $R_1$ is selected from $C_{4-6}$ alkyl, $C_{2-6}$ alkenyl, heteroaryl and aryl.

In one embodiment, $R_1$ is selected from $C_{4-7}$cycloalkyl, $C_{1-2}$alkylaryl and $C_{1-2}$alkylheteroaryl.

Exemplary $R_1$ groups include cyclohexyl, -methylcyclopentyl, —$CH_2CH$=$CH_2$, ethyl, n-propyl, n-butyl, t-butyl, i-butyl, —$CH_2C(Me)_3$, n-pentyl, —$CH_2CH_2C(Me)_3$, n-hexyl, n-heptyl, -cyclopentyl, -methylcyclohexyl, phenyl, -methylphenyl, -methylpyridinyl, thiazole, triazole, imidazole, oxazole, furan, thiophene and tetrazole, for example are selected from —$CH_2CH$=$CH_2$, n-butyl, t-butyl, i-butyl, —$CH_2C(Me)_3$, n-pentyl, —$CH_2CH_2C(Me)_3$, n-hexyl, n-heptyl, -cyclopentyl, -methylcyclohexyl, phenyl, -methylphenyl, -methylpyridinyl, thiazole, triazole, imidazole, oxazole, furan, thiophene and tetrazole.

Further exemplary $R_1$ groups include those aryl or heteroaryl groups just mentioned in which the aryl or heteroaryl group is substituted.

When $X_1$ Represents $R_3$

When $X_1$ represents $R_3$, $R_3$ may for example represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocyclic aryl or monocyclic heteroaryl; and wherein one or more carbon atoms of $R_3$ not being part of an aryl or heteroaryl group are optionally replaced by a heteroatom selected from O, N and $S(O)_p$ in which p represents 0, 1 or 2 save that the atom adjacent to the carbonyl group to which $R_3$ is attached is not O or N and wherein one or more carbon atoms of $R_3$ are optionally replaced by carbonyl.

Suitably, $R_3$ may for example represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl.

Suitably $R_3$ represents $C_{1-6}$alkyl, $C_{2-6}$alkenyl, $C_{1-4}$alkyl $C_{4-7}$cycloalkyl or $C_{1-4}$alkyl$C_{5-7}$cycloalkenyl.

Exemplary $R_3$, groups include -methylcyclopentyl, -ethylcyclopentyl, n-propyl, —$CH(Me)(ethyl)$, t-butyl, —$CH(ethyl)_2$, —$CH(ethyl)(i-propyl)$, —$CH(Me)(i-butyl)$, $CH(Me)(n-propyl)$, —$CH(Me)(n-butyl)$, —$CH(methyl)(n-pentyl)$, —$CH(ethyl)(n-propyl)$, cyclopentyl, tetrahydrofuran, cyclohexyl, cycloheptyl, hexahydrooxepine, -methylcyclohexyl, -ethylcyclohexyl, —$CH(Me)(O-ethyl)$, —$CH(Me)(O-isopropyl)$, —$CH(OMe)(ethyl)$, —$CH(Me)(O-ethyl)$, —$CH(OMe)(i-propyl)$, —$CH(Me)(OMe)$, —$CH(Me)(O-n-propyl)$, —$CH(Me)(O-n-butyl)$, —$CH(ethyl)(O-ethyl)$, —$CH_2C(Me)_3$, —$CH_2CH_2C(Me)_3$, thiazole, imidazole, triazole, tetrazole, oxazole, furan, pyridine and phenyl.

Further exemplary $R_1$ groups include those aryl or heteroaryl groups just mentioned in which the aryl or heteroaryl group is substituted.

Further Suitable Embodiments

In a suitable embodiment of the invention, $X_1$ represents NMe(OMe), $R_4$ represents H, $R_5$ represents OH, $R_6$ represents H, $R_7$ represents F, $R_8$ represents H, $X_2$ represents C, $X_3$ represents C, $X_4$ represents C, $X_5$ represents C, $X_6$ represents C, n represents a single bond, and $R_9$ represents OH as represented by the following structure:

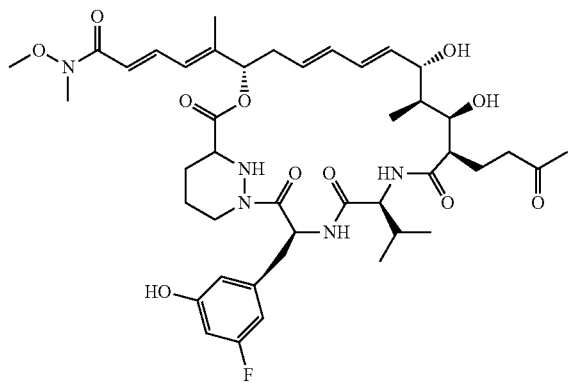 [SMILES: CON(C)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cc(O)cc(F)c2)C(=O)N2CCCC(N2)C(=O)O1]

In another suitable embodiment of the invention, $X_1$ represents NMe(OMe), $R_4$ represents H, $R_5$ represents OH, $R_6$ represents H, $R_7$ represents F, $R_8$ represents H, $X_2$ represents C, $X_3$ represents C, $X_4$ represents C, $X_5$ represents C, $X_6$ represents C, n represents a double bond, and $R_9$ represents H as represented by the following structure:

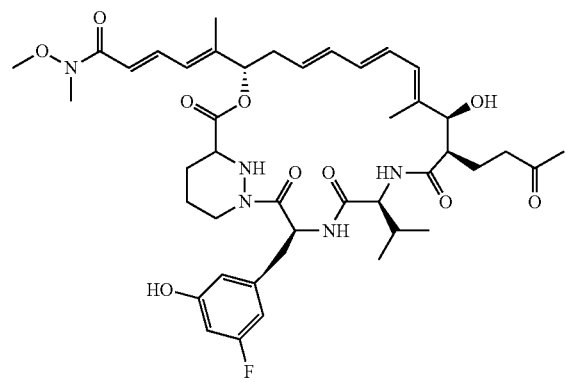 [SMILES: CON(C)C(=O)/C=C/C=C(\C)[C@@H]1C/C=C/C=C/C=C(\C)[C@@H](O)[C@@H](CCC(C)=O)C(=O)N[C@@H](C(C)C)C(=O)N[C@@H](Cc2cc(O)cc(F)c2)C(=O)N2CCCC(N2)C(=O)O1]

In another suitable embodiment of the invention, $X_1$ represents $NR_1R_2$ in which $R_1$ and $R_2$ together represent $CH_2CH_2CH_2CH_2O$ which are joined to form a heterocycle, $R_4$ represents H, $R_5$ represents OH, $R_6$ represents H, $R_7$ represents F, $R_8$ represents H, $X_2$ represents C, $X_3$ represents C, $X_4$ represents C, $X_5$ represents C, $X_6$ represents C, n represents a single bond, and $R_9$ represents OH as represented by the following structure:

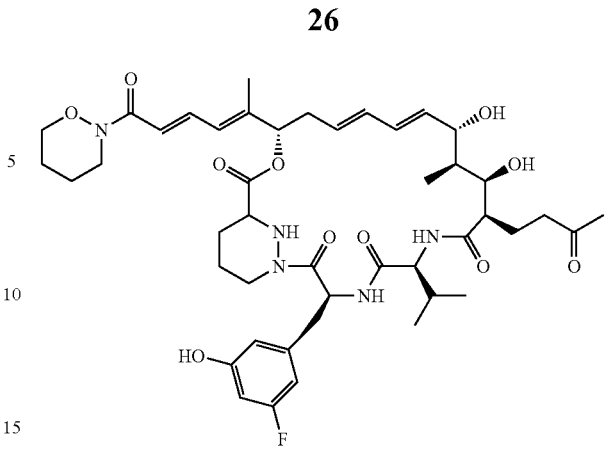

In another suitable embodiment of the invention, $X_1$ represents $NR_1R_2$ in which $R_1$ and $R_2$ together represent $CH_2CH_2CH_2CH_2O$ which are joined to form a heterocycle, $R_4$ represents H, $R_5$ represents OH, $R_6$ represents Me, $R_7$ represents H, $R_8$ represents H, $X_2$ represents C, $X_3$ represents C, $X_4$ represents C, $X_5$ represents C, $X_6$ represents C, n represents a single bond, and $R_9$ represents OH as represented by the following structure:

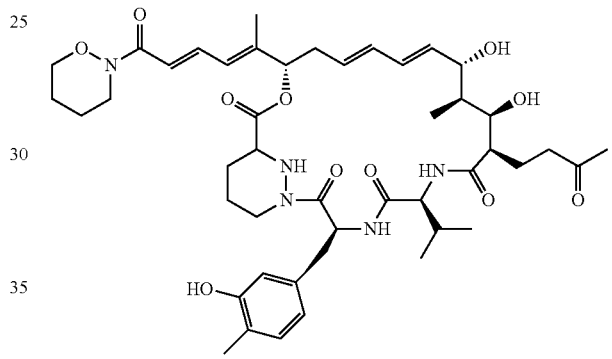

In another suitable embodiment of the invention, $X_1$ represents NMe(OMe), $R_4$ represents H, $R_5$ represents OH, $R_6$ represents F, $R_7$ represents F, $R_8$ represents H, $X_2$ represents C, $X_3$ represents C, $X_4$ represents C, $X_5$ represents C, $X_6$ represents C, n represents a single bond, and $R_9$ represents OH as represented by the following structure:

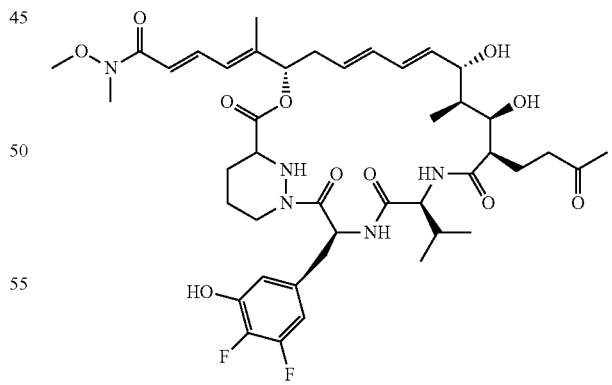

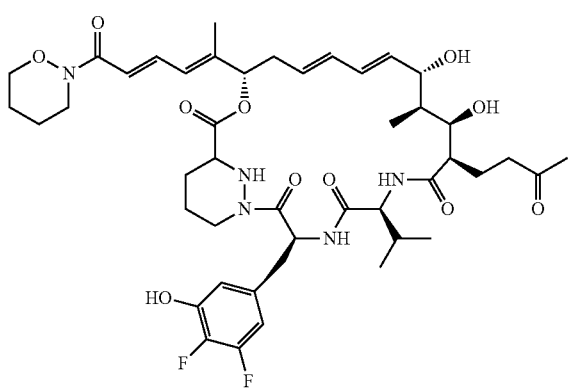 [SMILES: CC(=O)CC[C@H]1C(=O)N[C@@H](C(C)C)C(=O)N[C@@H](Cc2cc(O)c(F)c(F)c2)C(=O)N2CCCC(N2)C(=O)O[C@H](/C(C)=C/C=C/C(=O)N2CCCCO2)C/C=C/C=C/[C@H](O)[C@H](C)[C@H]1O]

In another suitable embodiment of the invention, $X_1$ represents NH(2-pyridinyl), $R_4$ represents H, $R_5$ represents OH, $R_6$ represents F, $R_7$ represents F, $R_8$ represents H, $X_2$ represents C, $X_3$ represents C, $X_4$ represents C, $X_5$ represents C, $X_6$ represents C, n represents a single bond, and $R_9$ represents OH as represented by the following structure:

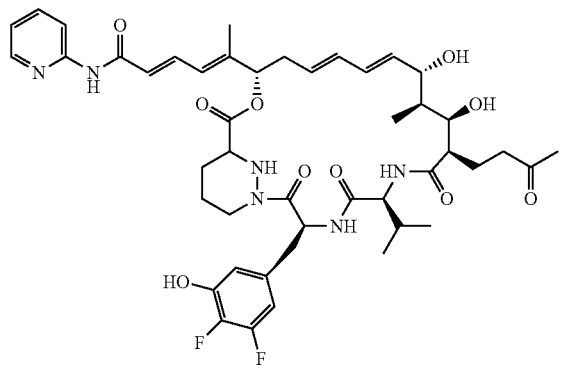 [SMILES: CC(=O)CC[C@H]1C(=O)N[C@@H](C(C)C)C(=O)N[C@@H](Cc2cc(O)c(F)c(F)c2)C(=O)N2CCCC(N2)C(=O)O[C@H](/C(C)=C/C=C/C(=O)Nc2ccccn2)C/C=C/C=C/[C@H](O)[C@H](C)[C@H]1O]

In another suitable embodiment of the invention, $X_1$ represents NH(2-pyridinyl), $R_4$ represents H, $R_5$ represents OH, $R_6$ represents F, $R_7$ represents H, $R_8$ represents H, $X_2$ represents C, $X_3$ represents C, $X_4$ represents C, $X_5$ represents C, $X_6$ represents C, n represents a single bond, and $R_9$ represents OH as represented by the following structure:

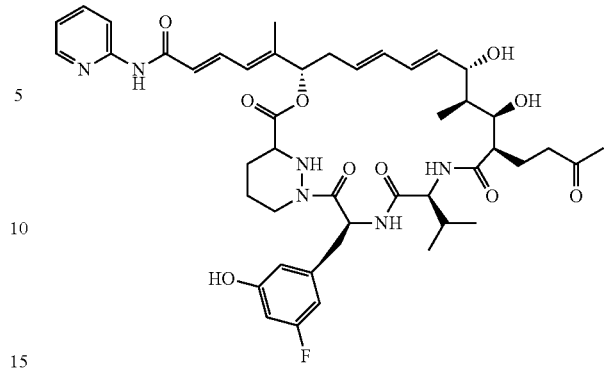

In some embodiments the double bond at the C26, 27 position (by reference to the structure of sanglifehrin A) may be in the cis form instead of the trans form.

In a suitable embodiment of the invention, the double bond at the C26, 27 position is in the cis form, as represented by the following formula:

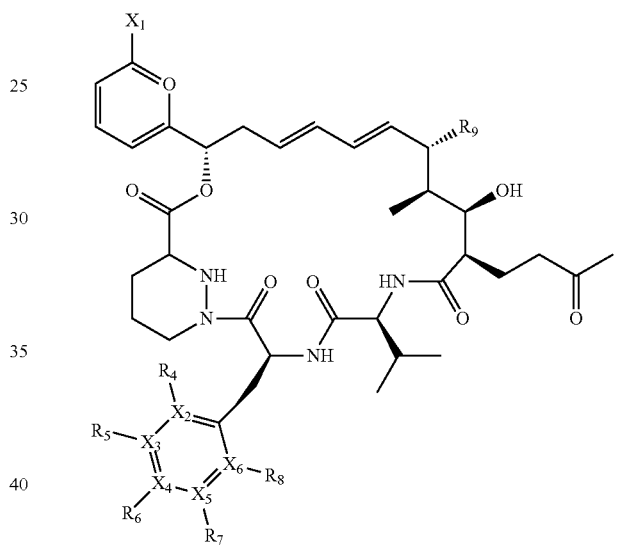

Such compounds may be produced during chemical synthesis.

In general, the compounds of the invention are prepared by mutasynthesis to generate compounds of formula (II), followed by semisynthesis.

Formula (IIA)

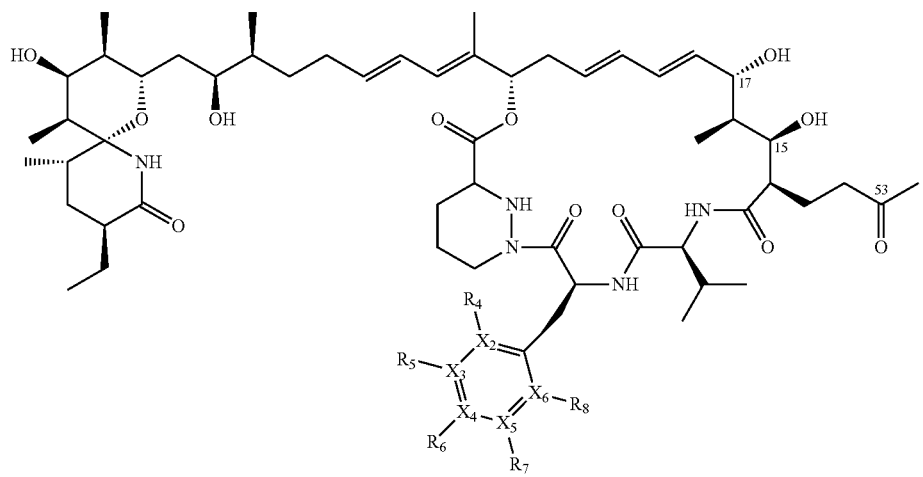

-continued

Formula (IIB)

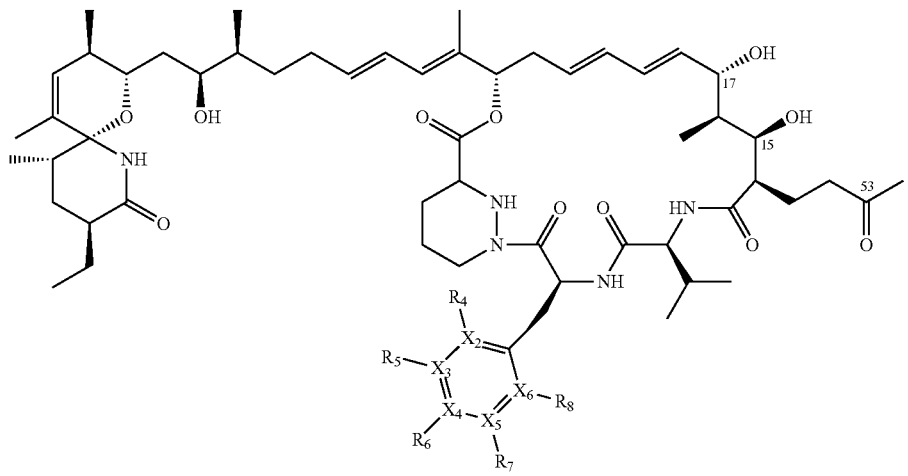

Suitable $X_2$, $X_3$, $X_4$, $X_5$, $X_6$, $R_4$, $R_5$, $R_6$, $R_7$ and $R_8$ groups in Formula (II) are as defined for compounds of formula (I).

In general, a process for preparing precursors of compounds of formula (I) or a pharmaceutically acceptable salt thereof comprises:

Inoculating a fermentation broth with a culture of a sanglifehrin producer (such as *Streptomyces* sp. A92-308110, also known as DSM 9954) or more preferably, a sanglifehrin producer with the sfaA gene or sfaA gene homologue inactivated or deleted;

Feeding the fermentation broth with a meta-tyrosine analogue (as shown in formula (III))

Allowing fermentation to continue until compounds of formula IIA and formula IIB are produced Extracting and isolating compounds of formula IIA and formula IIB Semisynthetic derivatisation of compounds of formula IIA and formula IIB to generate the compound of formula I.

Compounds of formula (III) are defined as follows:

Formula (III)

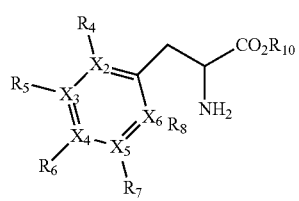

where $R_{10}$ represents H or an ester forming group such as an alkyl group, e.g. $C_{1-6}$alkyl such as Me.

Suitable $X_2$, $X_3$, $X_4$, $X_5$, $X_6$, $R_4$, $R_5$, $R_6$, $R_7$ and $R_8$ groups in Formula (III) are as defined for compounds of formula (I).

The feed may be racemic or the L-form of a compound of formula (III).

Compounds of formula (III) are either commercially available or prepared by standard organic synthetic chemistry techniques. One generic route to compounds of formula (III) is as shown in the following scheme 1.

Scheme 1:

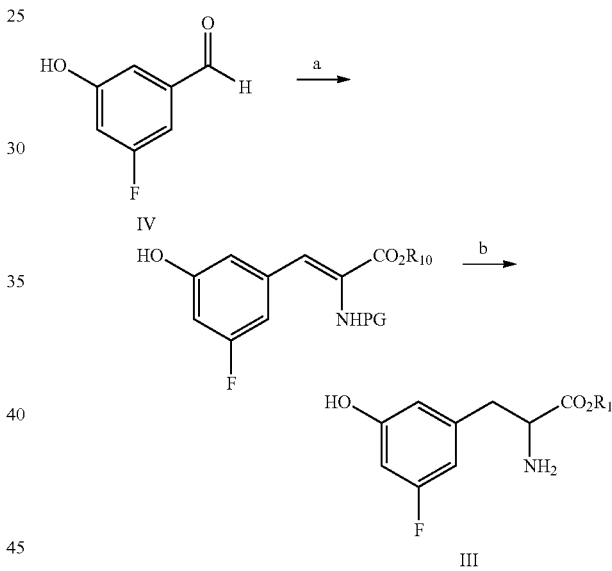

a) coupling aldehyde of formula (IV) with suitable fragment, e.g. $(R_{11}O)_2P(O)CH(NHPG)CO_2R_{10}$, and
b) hydrogenation and deprotection as necessary.
PG = protecting group.

Aldehydes of formula (IV) may be commercially available or readily synthesised by one skilled in the art. Protection and deprotection chemistry may need to be employed in generating compounds of formula (III) from compounds of formula (IV). These techniques are known to one skilled in the art and suitable protecting groups are described in Greene's Protective Groups in Organic Synthesis (Wuts and Greene, 4$^{th}$ Edition, 2007)

Following generation of compounds of formula (IIA) and formula (IIB), the compounds of the invention are prepared by semi-synthetic derivatisation. Semisynthetic methods for generating the sanglifehrin macrocylic aldehyde are described in U.S. Pat. No. 6,124,453, Metternich et al., 1999, Banteli et al., 2001 and Sedrani et al., 2003.

In general, the semisynthetic process for preparing certain compounds of formula (I) or a pharmaceutically acceptable salt thereof from a sanglifehrin mutasynthetic analogue comprises:

(a) dihydroxylation of the sanglifehrin analogue;
(b) oxidative cleavage of the 1,2-diol to yield an aldehyde; and
(c) coupling said aldehyde with a stabilised carbanion (or canonical form thereof), such as a phosphonate carbanion, using a compound of formula V.

This is shown retrosynthetically below:

Hence, a process for preparing compounds of the invention comprises reacting a compound of formula (V) with an aldehydic macrocycle (compound of formula (VI)).

The preparation of compounds of formula (VI) may be performed by a process analogous to that described previously for the conversion of sanglifehrin A to its corresponding aldehydic macrocycle (Metternich et al. 1999). Briefly, the

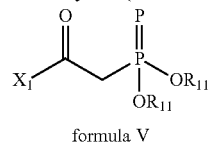

formula V

+

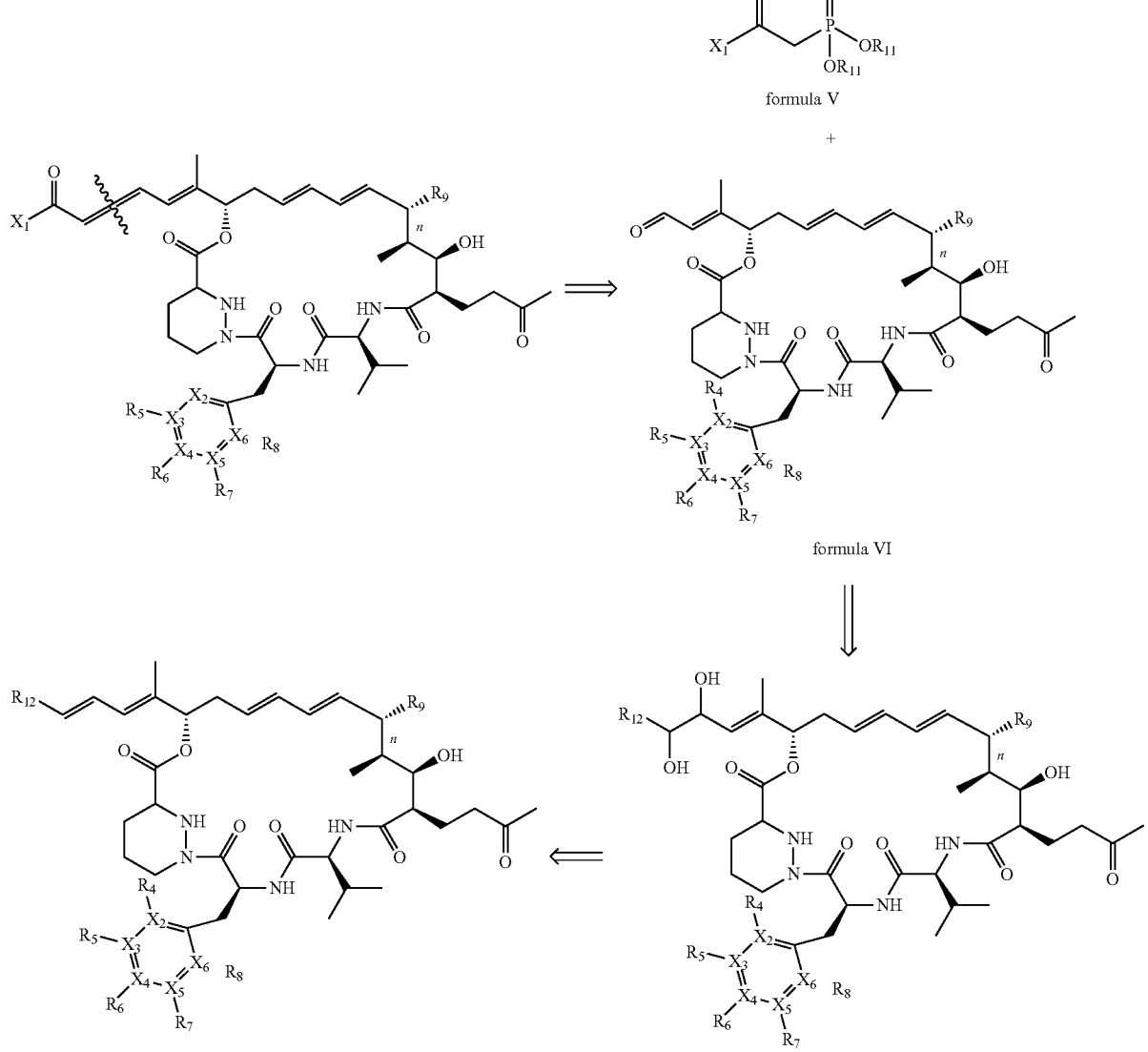

formula VI

Wherein for sanglifehrin A mutasynthetic analogues,

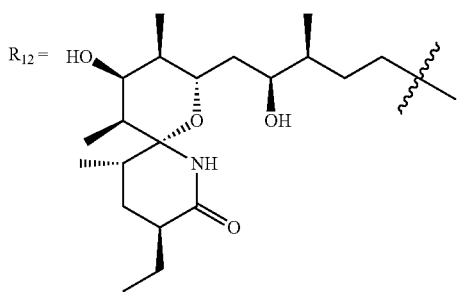 [SMILES: *CC[C@H](C)[C@@H](O)C[C@@H]1O[C@@]2(NC(=O)[C@@H](CC)C[C@@H]2C)[C@@H](C)[C@@H](O)[C@H]1C]

$R_{11}$ groups, which may be the same or different, independently represent alkyl (e.g. C1-4-alkyl) or benzyl.

compound of formula (II) is dihydroxylated using modified Sharpless conditions (catalytic osmium tetroxide). The use of the chiral ligands aids in promoting selectivity. The resultant diol can then be cleaved oxidatively, using for instance sodium periodate. The resultant compound of formula VI can then be used as a substrate for derivatisation to a homologated amide, ester or ketone. Typically a compound of formula (V) is dissolved in an aprotic solvent, cooled and the treated with a base, for example sodium hydride. A compound of formula (VI) is then added and the reaction warmed in temperature. After a suitable period of time the reaction is stopped and the compound of formula I is purified by standard conditions (e.g. preparative HPLC, preparative TLC etc, normal phase flash chromatography).

Derivatisations to introduce changes to groups $R_9$, and n can be carried out prior to generation of the compound of formula VI or after the reaction to form the homologated amide. Briefly, the hydroxyl at $R_9$ can be eliminated by treatment of a suitable substrate in acidic conditions in order to generate a conjugated triene.

Compounds of formula (V) may be known or may be prepared using known methods.

For example compounds of formula (V) in which $X_1$ represents $NR_1R_2$ may be readily synthesised from available amines (e.g. $R_1R_2NH$). As shown in scheme 1 (below) the amine may be used to treat chloroacetyl chloride or similar to form an alpha-chloroamide. The alpha-chloroamide is then treated in an Arbuzov reaction to generate a compound of formula V. Other routes to compounds of formula V will be apparent to one skilled in the art.

Scheme 1

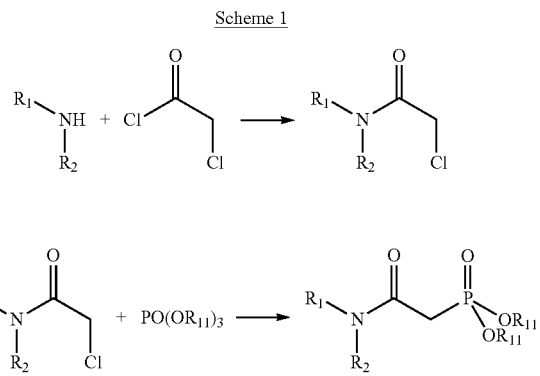

Further compounds of formula (V) in which $X_1$ represents $R_3$ may be known or readily synthesised from available carboxylic acid derivatives (e.g. $R_3COX$). As shown in scheme 2 (below) the carboxylic acid derivative may be coupled onto a methyl phosphonate after the phosphonate has been treated with base. This yields a compound of formula (V), though other routes to compounds of formula V will be apparent to one skilled in the art.

Scheme 2

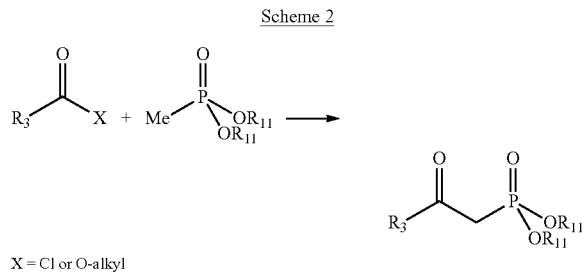

X = Cl or O-alkyl

Further compounds of formula (V) in which $X_1$ represents $OR_1$ may be known or readily synthesised from available alcohols (e.g. $R_1OH$). As shown in scheme 3 (below) the alcohol may be used to treat chloroacetyl chloride or similar to form an alpha-chloroester. The alpha-chloroester is then treated in an Arbuzov reaction to generate the compound of formula II. Other routes to compounds of formula II will be apparent to one skilled in the art.

Scheme 3

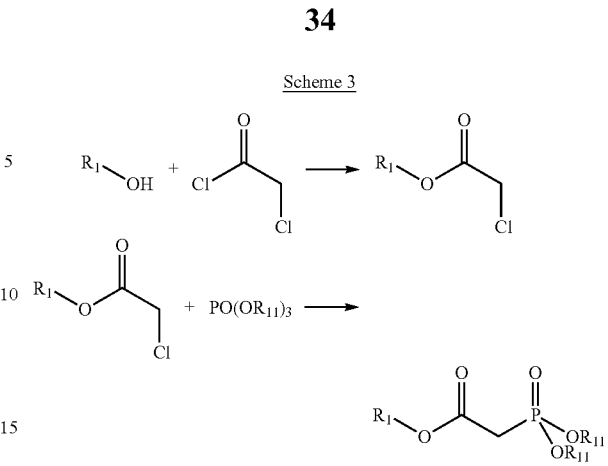

If desired or necessary, protecting groups may be employed to protect functionality in the aldehydic macrocycle, macrocycle, alcohol ($R_1OH$), carboxylic acid derivative ($R_1R_2R_3COX$) or the amine ($R_1R_2NH$), or in compounds of formula V as described in T. W. Green, P. G. M. Wuts, *Protective Groups in Organic Synthesis*, Wiley-Interscience, New York, 1999.

In addition to the specific methods and references provided herein a person of skill in the art may also consult standard textbook references for synthetic methods, including, but not limited to Vogel's Textbook of Practical Organic Chemistry (Furniss et al., 1989) and March's Advanced Organic Chemistry (Smith and March, 2001).

A sanglifehrin analogue according to the invention may be administered alone or in combination with other therapeutic agents. Co-administration of two (or more) agents may allow for lower doses of each to be used, thereby reducing side effect, can lead to improved potency and therefore higher SVR, and a reduction in resistance.

Therefore in one embodiment, the mutasynthetic sanglifehrin analogue is co-administered with one or more therapeutic agent/s for the treatment of HCV infection, taken from the standard of care treatments. This could be an interferon (e.g. pIFNα and/or ribavirin).

In an alternative embodiment, a sanglifehrin macrocycle of the invention is co-administered with one or more other antiviral agents, such as a STAT-C (specifically targeted agent for treatment of HCV) or DAA (direct acting antivirals), which could be one or more of the following: Non-nucleoside Polymerase inhibitors (e.g. ABT-333, ABT-072, BMS 791325, IDX375, VCH-222, BI 207127, ANA598, VCH-916, GS 9190, PF-00868554 (Filibuvir) or VX-759), Nucleoside or nucleotide polymerase inhibitors (e.g. 2'-C-methylcytidine, 2'-C-methyladenosine, R1479, PSI-6130, R7128, R1626, PSI 7977 or IDX 184), Protease inhibitors (e.g. ABT-450, ACH-1625, BI 201355, BILN-2061, BMS-650032, CTS 1027, Danoprevir, GS 9256, GS 9451, MK 5172, IDX 320, VX-950(Telaprevir), SCH503034(Boceprevir), TMC435350, MK-7009 (Vaneprivir), R7227/ITMN-191, EA-058, EA-063 or VX 985), NS5A inhibitors (e.g. A-831, BMS 790052, BMS 824393, CY-102 or PPI-461), silymarin, NS4b inhibitors, serine C-palmitoyltransferase inhibitors, Nitazoxanide or viral entry inhibitors (e.g. PRO206).

In an alternative embodiment, a sanglifehrin macrocycle of the invention is co-administered with one or more other antiviral agents (such as highly active antiretroviral therapy (HAART)) for the treatment of HIV, which could be one or more of the following: nucleoside reverse transcriptase inhibitors (NRTI) (e.g. Emtricitabine or Tenofovir), non-nucleoside reverse transcriptase inhibitors (NNRTI) (e.g. Rilipivirine or Efavirenz), protease inhibitors (PI) (e.g. Ritonavir or Lopinavir), fusion inhibitors (e.g. Maraviroc or Enfuvirtide), CCR5 inhibitors (e.g. Aplaviroc or Vicriviroc), maturation inhibitors (e.g. Bevirimat), CD4 monoclonal antibodies (e.g. Ibalizumab) and integrase inhibitors (e.g. Eltiegravir).

In an alternative embodiment, a sanglifehrin macrocycle of the invention is co-administered with one or more other antiviral agents for the treatment of HBV, which could be one or more of the following: interferons (e.g. interferon alpha or pegylated interferon alpha), nucleoside or nucleotide analogues (e.g. lamivudine, entecavir, adefovir dipivoxil or telbivudine), other immunomodulators (e.g. Thymosin alpha, CYT107 or DV-601) or HMG CoA reductase inhibitors (e.g. Simvastatin).

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds of the invention will normally be administered orally in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above the formulations of this invention may include other agents conventional in the art having regard to the type of formulation in question, for example those suitable for oral administration may include flavouring agents.

Advantageously, agents such as preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Further Aspects of the Invention Include:

- A compound according to the invention for use as a pharmaceutical;
- A compound according to the invention for use as a pharmaceutical for the treatment of viral infections (especially RNA virus infections) such as HCV or HIV infection, for use as an anti-inflammatory or for prophylaxis of organ transplant rejection;
- A pharmaceutical composition comprising a compound according to the invention together with a pharmaceutically acceptable diluent or carrier;
- A pharmaceutical composition comprising a compound according to the invention together with a pharmaceutically acceptable diluent or carrier further comprising a second or subsequent active ingredient, especially an active ingredient indicated for the treatment of viral infections such as HCV or HIV infection, for use as an anti-inflammatory or for prophylaxis of organ transplant rejection;

A method of treatment of viral infections (especially RNA virus infections) such as HCV or HIV infection, for use as an anti-inflammatory or for prophylaxis of organ transplant rejection which comprises administering to a subject a therapeutically effective amount of a compound according to the invention;

Use of a compound according to the invention for the manufacture of a medicament for the treatment of viral infections such as HCV or HIV infection, for use as an anti-inflammatory or for prophylaxis of organ transplant rejection.

General Methods
Materials and Methods
Bacterial Strains and Growth Conditions

The sanglifehrin producer *Streptomyces* sp. A92-308110 (DSM no 9954, purchased from DSMZ, Braunschweig, Germany) also termed BIOT-4253 and BIOT-4370 or its derivatives, such as BIOT-4585 are maintained on medium oatmeal agar, MAM, ISP4 or ISP2 (see below) at 28° C.

BIOT-4585 (for construction methodology, see Example 1) was grown on oatmeal agar at 28° C. for 7-10 days. Spores from the surface of the agar plate were collected into 20% w/v sterile glycerol in distilled and stored in 0.5-ml aliquots at −80° C. Frozen spore stock was used for inoculating seed media SGS or SM25-3. The inoculated seed medium was incubated with shaking between 200 and 300 rpm at 5.0 or 2.5 cm throw at 27° C. for 24 hours. The fermentation medium SGP-2 or BT6 were inoculated with 2.5%-10% of the seed culture and incubated with shaking between 200 and 300 rpm with a 5 or 2.5 cm throw at 24° C. for 4-5 days. The culture was then harvested for extraction.

Meta-Tyrosine Analogues

Methyl (2S)-2-amino-3-(6-hydroxy(2-pyridyl))propanoate, L-3-aminophenylalanine methyl ester, L-4-methyl-meta-tyrosine methyl ester, L-4-fluoro-meta-tyrosine methyl ester and L-4,5-difluoro-meta-tyrosine methyl ester were purchased from Netchem (USA).

DL-3-fluorophenylalanine and L-phenylalanine were purchased from Sigma (UK).

DL-meta-tyrosine was purchased from Fluorochem (UK).

L-meta-tyrosine was purchased from Alfa Aesar (UK).

(S)-methyl 2-amino-3-(3-fluoro-5-hydroxyphenyl)propanoate was purchased from NetChem (USA). (3-bromo-5-fluoroanisole (9-1) was purchased from Accela ChemBio Co., Ltd., (Shanghai, China) and can also be purchased from Amfinecom Inc (USA) or Apollo Scientific Ltd. (UK)).

DL-5-fluoro-meta-tyrosine (8), DL-5-fluoro-meta-tyrosine (9), methyl 2-amino-3-(3-fluoro-5-hydroxyphenyl)propanoate (10), methyl 2-amino-3-(2-fluoro-5-hydroxyphenyl)propanoate (11), methyl 2-amino-3-(2-fluoro-3-hydroxyphenyl)propanoate (12) and methyl 2-amino-3-(2,6-difluoro-3-hydroxyphenyl)propanoate (13) were synthesised as follows:

DL-4-fluoro-meta-tyrosine (8)

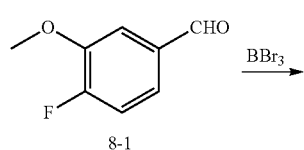

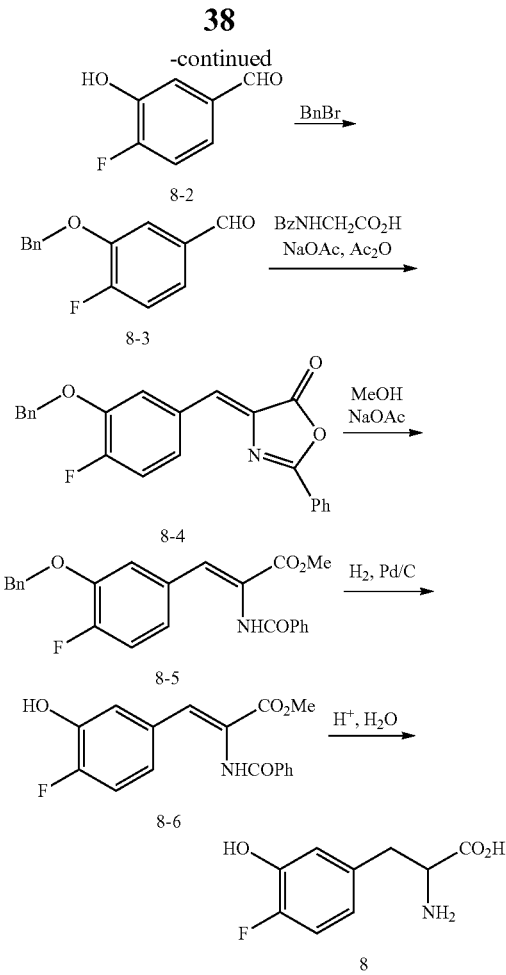

To a solution of 8-1 (3 g, 19.5 mmol) in dry DCM (150 mL) was added dropwise BBr₃ (4 M in DCM, 14.6 ml, 58.5 mmol) at −70° C. After the addition, the reaction mixture was stirred at −20° C. for 3 h, ice-water was added carefully, and extracted with DCM. The organic layers were washed with water and brine, dried over $Na_2SO_4$, filtered and concentrated. The residue was purified by flash chromatographed on silica to give the desired compound 8-2.

To a solution of 8-2 (0.9 g, 6.4 mmol) in acetone (40 mL) was added $K_2CO_3$ (2.2 g, 16 mmol) at room temperature. The reaction mixture was stirred at room temperature overnight. Water was added and acetone was removed under vacuum, and then extracted with EtOAc, the organic layers were washed with water and brine, dried over $Na_2SO_4$, filtered and concentrated. The residue was purified by flash chromatographed on silica to give the desired compound 8-3.

A mixture of 8-3 (1 g, 4.34 mmol), hippuric acid (860 mg, 4.80 mmol), NaOAc (400 mg) and $Ac_2O$ (2.2 mL) was stirred at 80° C. for 2 h. The yellow reaction mixture was cooled and cold EtOH (10 mL) was added, the mixture was cooled in an ice bath for 15 min and then was poured into 30 mL of ice water, chilled and the product was collected by filtration. The solid was dried in vacuo to yield 8-4.

A solution of 8-4 (300 mg, 0.8 mmol) and NaOAc (71 mg, 0.87 mmol) in MeOH (50 mL) was stirred at room temperature overnight. The solvent was removed by rotary evaporation and the reside was dissolved in 50 mL of EtOAc, the EtOAc solution was washed two times with water and concentrated to give 8-5.

A solution of 8-5 (360 mg, 0.89 mmol) in MeOH (50 mL) was hydrogenated over 10% Pd/C (77 mg) at normal pressure for 20 h. After removal of the catalyst by filtration, the solvent was evaporated to give the product 8-6.

A solution of 8-6 (210 mg) in 3 N HCl (10 mL) was refluxed for 24 h. the solution was concentrated to dryness and the residue was purified by reverse-combiflash to give the target product 8.

DL-5-fluoro-meta-tyrosine (9) and methyl 2-amino-3-(3-fluoro-5-hydroxyphenyl)propanoate (10)

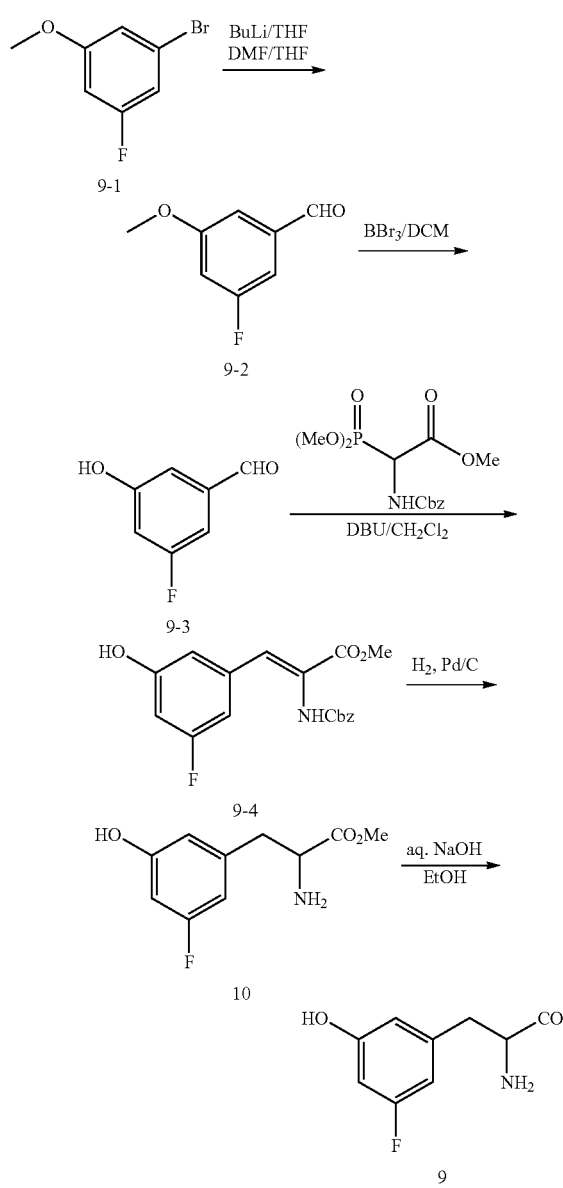

To a solution of 9-1 (20 g, 97.55 mmol) in tetrahydrofuran (100 mL) was added dropwise n-butyl lithium (43 mL, 2.5 M, 107.3 mmol) at −78° C. It was stirred for 30 minutes and N,N-dimethylformamide (15.1 mL, 195.1 mmol) was added at this temperature. It was stirred for another 30 minutes and the cold bath was removed. After 1 hour, the reaction was quenched with saturated aqueous ammonium chloride. The organic layer was washed with water and saturated aqueous sodium chloride, dried (sodium sulfate), filtered and concentrated. The residue was purified by chromatography on silica to give 9-2.

To a solution of 9-2 (6 g, 38.9 mmol) in dry DCM (200 mL) was added dropwise $BBr_3$ (4 M in DCM, 30 ml, 116.8 mmol) at −70° C. After the addition, the reaction mixture was stirred at −20° C. for 3 hours, ice-water was added carefully, and extracted with DCM. The organic layers were washed with water and brine, dried over $Na_2SO_4$, filtered and concentrated. The residue was purified by flash chromatographed on silica to give the desired compound 9-3.

To a solution of methyl 2-(benzyloxycarbonylamino)-2-(dimethoxyphosphoryl)acetate (4.64 g, 14 mmol) in DCM (150 mL) was added DBU (4.26 g, 28 mmol) at room temperature. After 10 min, 9-3 (1.95 g, 14 mmol) was added and the resulting mixture was stirred at room temperature overnight. The solution was diluted with EtOAc (150 mL), separated and the organic layer was washed with 1 N HCl, dried over $Na_2SO_4$, filtered and concentrated. The residue was purified by flash chromatography on silica to give 9-4.

A solution of 9-4 (1 g) in MeOH (20 mL) was hydrogenated over 200 mg of 10% Pd/C at normal pressure overnight. After removal of the catalyst by filtration, the solvent was evaporated to give 10.

To a solution of 10 (300 mg, 1.4 mmol) in EtOH (30 mL) was added aq. NaOH (2 N, 4 mL), the reaction was stirred at room temperature for 30 minutes. The solvent was removed and the residue was neutralized to pH=6 with 2 N HCl and the white crystals that formed were collected by filtration to give the target compound 9.

Alternative route to methyl 2-amino-3-(3-fluoro-5-hydroxyphenyl)propanoate (10)

(3,5-Difluorobromobenzene (9a-1) was purchased from Darui Fine Chemicals Co., Ltd., (Shanghai, China) and can also be purchased from Alfa Aesar or Sigma Aldrich.)

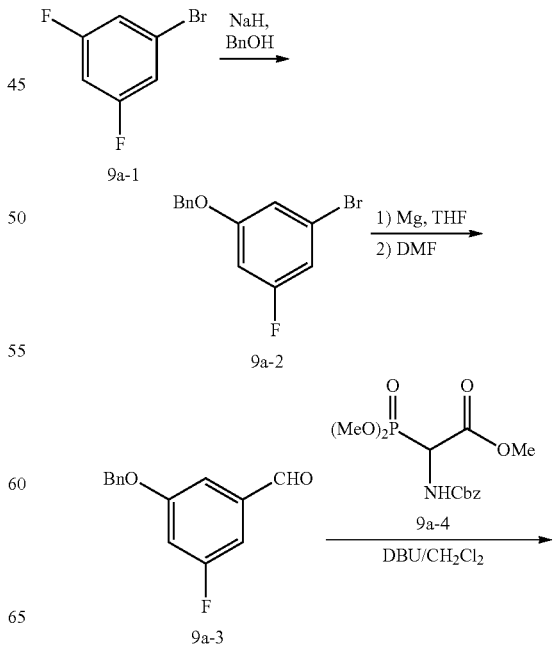

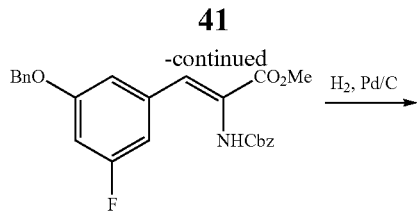

9a-5

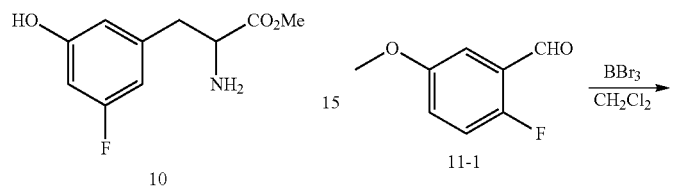

10

Preparation of 9a-2

To a solution of BnOH (1.61 mL, 15.54 mmol) in DMF (30 mL) was added NaH (622 mg, 60% dispersion in mineral oil, 15.54 mmol) at 0° C. Stirring was continued at room temperature for 0.5 h to give a clear solution. 9a-1 (1.79 mL, 15.54 mmol) was added at such a rate to maintain the temperature below 40° C. The mixture was stirred at room temperature overnight to give a yellow solution. The reaction was quenched by water and extracted with petroleum ether (35 mL×4). The combined organic layers were concentrated. And the residue was purified by silica gel chromatography eluting with petroleum ether to afford 9a-2 (2.544 g) as colorless oil.

Preparation of 9a-3

To a dry three flask were added Mg (170.1 mg, 7.10 mmol), anhydrous THF (10 mL), and a small quantity of iodine under nitrogen. ⅓ of 9a-2 (1.664 g, 5.9192 mmol) in THF (2 mL) was added. The mixture was heated to reflux. During this time, the yellow mixture gradually became bright yellow. Then the remaining ⅔ of 9a-2 was added dropwise, and the reaction mixture was refluxed for another 0.5 h.

To the above mixture was added DMF (0.504 mL, 6.51 mmol) slowly at 0° C. Stirring was continued for 0.5 h at room temperature. HCl (2 M, 10 mL) was added, and THF was evaporated. The residue was extracted with ethyl acetate (25 mL×3). And the combined organic layers were washed with brine and concentrated in vacuo. The residue was purified by silica gel chromatography eluting with petroleum ether to petroleum ether/ethyl acetate=20/1 to give 9a-3 (694 mg) as colorless oil.

Preparation of 9a-5

To a solution of methyl 2-(benzyloxycarbonylamino)-2-(dimethoxyphosphoryl)acetate, 9a-4 (993 mg, 3.00 mmol) in DCM (30 mL) was added DBU (832 □uL, 5.57 mmol) at room temperature. After 10 min, 9a-3 (694 mg, 3.01 mmol) was added and the resulting mixture was stirred at room temperature for 1 hr. The solution was washed with HCl (1 M, 10 mL), and the combined organic layers were dried and concentrated in vacuo. The residue was purified by flash chromatography on silica (eluting with dichloromethane/ethyl acetate=10/1) to give 9a-5 (1.11 g).

Preparation of 10

A solution of 9a-5 (100 mg) in MeOH (50 mL) was hydrogenated over 20 mg of 10% Pd/C at normal pressure for 2 hrs. After removal of the catalyst by filtration, the solvent was evaporated to give 10 (33 mg).

Methyl 2-amino-3-(2-fluoro-5-hydroxyphenyl)propanoate (11)

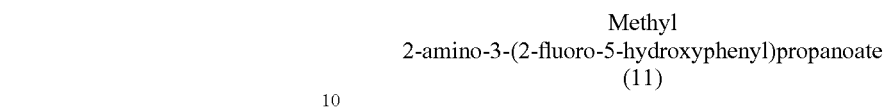

11-1

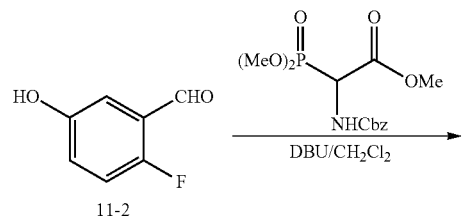

11-2

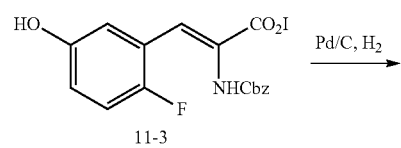

11-3

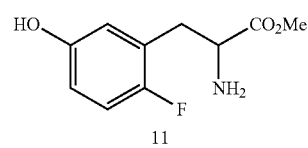

11

To a solution of the compound 11-1 (1.4 g, 9 mmol) in 50 mL DCM was added dropwise BBr$_3$ (4M in DCM, 3.6 mL, 13.5 mmol) at −78° C. After the addition, the reaction was stirred at −20° C. for 4 hours. Then slow addition of ice/water, the layers was separated, the organic layers was washed with water and brine, dried over Na$_2$SO$_4$ and evaporated to dryness. The residue was used to next step without further purification.

To a solution of methyl 2-(benzyloxycarbonylamino)-2-(dimethoxyphosphoryl)acetate (3 g, 9 mmol) in 100 mL DCM was added DBU (2.8 g, 18 mmol) at room temperature, after 10 mins, the compound 11-2 (crude compound from last step) was added, stirred at room temperature for 2 hours. The solution was then diluted with DCM (50 mL), washed with 1N HCl (20 mL), dried over Na$_2$SO$_4$ and evaporated to dryness. The residue was purified by silica gel chromatography (petroleum ether/ethyl acetate=5/1) to give 11-3.

A mixture of the compound 11-3 (500 mg, 1.5 mmol) in MeOH (20 mL) was hydrogenated over 50 mg of 10% Pd/C at normal pressure overnight. After removal of the catalyst by filtration, the solvent was evaporated to get the crude product, which was purified by reverse-combiflash to get 11 as a white solid.

Methyl 2-amino-3-(2-fluoro-3-hydroxyphenyl)propanate (12)

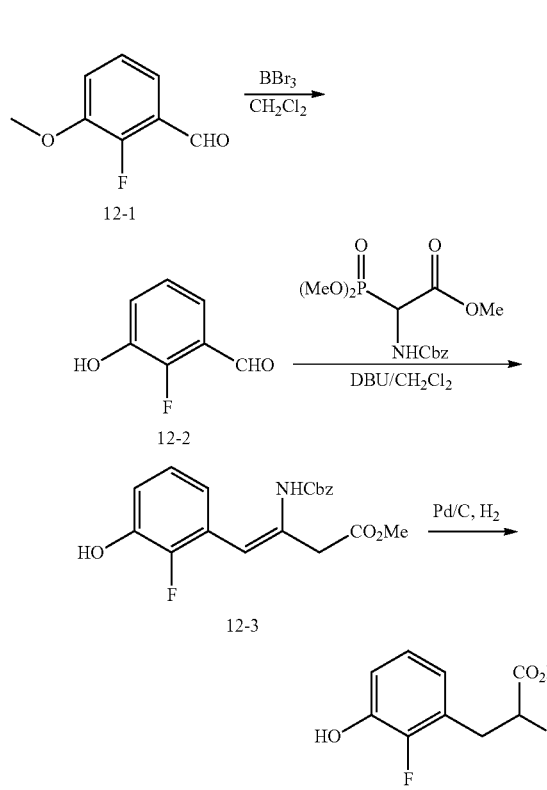

which was purified by reverse-combiflash to get the desired compound 12 as a white solid.

Methyl 2-amino-3-(1,6-difluoro-3-hydroxyphenyl)propanoate (13)

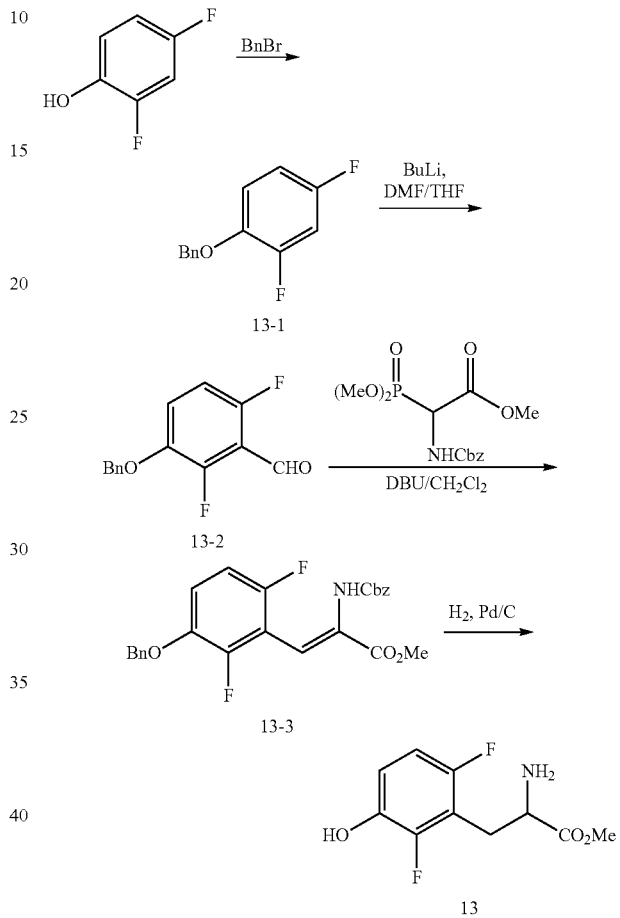

To a solution of the compound 12-1 (1.4 g, 9 mmol) in 50 mL DCM was added dropwise BBr$_3$ (4M in DCM, 3.6 mL, 13.5 mmol) at −78° C. After the addition, the reaction was stirred at −20° C. for 4 hours. After slow addition of ice/water, the layers were separated, the organic layer was washed with water and brine, dried over Na$_2$SO$_4$ and evaporated to dryness. The residue was used to next step without further purification.

To a solution of methyl 2-(benzyloxycarbonylamino)-2-(dimethoxyphosphoryl)acetate (3 g, 9 mmol) in 100 mL DCM was added DBU (2.7 mL, 18 mmol) at room temperature, after 10 mins, the compound 12-2 (crude compound from last step) was added, stirred at room temperature for 2 hours. The solution was then diluted with DCM (100 mL), washed with 1N HCl (30 mL), dried over Na$_2$SO$_4$ and evaporated to dryness. The residue was purified by silica gel chromatography (petroleum ether/ethyl acetate=5/1) to give 12-3.

A mixture of the compound 12-3 (500 mg, 1.44 mmol) in MeOH (10 mL) was hydrogenated over 100 mg of 10% Pd/C at normal pressure overnight. After removal of the catalyst by filtration, the solvent was evaporated to get the crude product, To a solution of 2,4-difluorophenol (2 g, 15.4 mmol) in 50 mL DMF was added K$_2$CO$_3$ (3.2 g, 23.1 mmol) and BnBr (2.2 mL, 18.5 mmol) at 0° C. The reaction was stirred at room temperature for 2 hours. Water (100 mL) and EA (200 mL) was added, the organic layers was washed with water (50 mL) and brine (50 mL), dried over Na$_2$SO$_4$ and evaporated to dryness. The residue was purified by silica gel chromatography (petroleum ether/ethyl acetate=10/1) to give the crude 13-1.

To a solution of the compound 13-1 (2 g, 9 mmol) in 10 mL THF was added dropwise n-BuLi (4 mL, 2.5 M) at −78° C. and stirred for 30 mins. DMF (1.3 g, 0.018 mmol) was added and stirred for 30 mins again. The cold bath was then removed and the reaction mixture was stirred at room temperature for 1 hour before being quenched with water. It was extracted with ethyl acetate (20 mL×3), dried over Na$_2$SO$_4$ and evaporated to dryness. The residue was purified by silica gel chromatography (petroleum ether/ethyl acetate=10/1) to give 13-2 as a yellow solid.

To a solution of methyl 2-(benzyloxycarbonylamino)-2-(dimethoxyphosphoryl)acetate (728 mg, 2.2 mmol) in 20 mL DCM was added DBU (319 mg, 2.1 mmol) at room temperature. After 10 mins, the compound 13-2 (500 mg, 2 mmol)

was added and stirred at room temperature for 2 hours. The solution was then diluted with DCM (50 mL), washed with 1N HCl (20 mL), dried over $Na_2SO_4$ and evaporated to dryness. The residue was purified by silica gel chromatography (petroleum ether/ethyl acetate=5/1) to give 13-3 as a yellow oil.

The compound 13-3 (600 mg, 1.32 mmol) in MeOH (20 mL) was hydrogenated over 60 mg of 10% Pd/C at normal pressure overnight. After removal of the catalyst by filtration, the solvent was evaporated to get the crude product, which was purified by reverse-combiflash to get the desired compound 13 as a white solid.

Media Recipes

Water Used for Preparing Media was Prepared Using Millipore Elix Analytical Grade Water Purification System SGS Seed Medium

| Ingredient (and supplier) | Recipe |
| --- | --- |
| Glucose (Sigma, G7021) | 7.50 g |
| Glycerol (Fisher scientific, G/0650/25) | 7.50 g |
| yeast extract (Becton Dickinson, 212770) | 1.35 g |
| malt extract (Becton Dickinson, 218630) | 3.75 g |
| potato starch (soluble) (Signma, S2004) | 7.50 g |
| NZ-amine A (Sigma, C0626) | 2.50 g |
| toasted soy flour, Nutrisoy (ADM, 063-160) | 2.50 g |
| L-asparagine (Sigma, A0884) | 1.00 g |
| $CaCO_3$ (Calcitec, V/40S) | 0.05 g |
| NaCl (Fisher scientific, S/3160/65) | 0.05 g |
| $KH_2PO_4$ (Sigma, P3786) | 0.25 g |
| $K_2HPO_4$ (Sigma, P5379) | 0.50 g |
| $MgSO_4 \cdot 7H_2O$ (Sigma, M7774) | 0.10 g |
| trace element solution B | 1.00 mL |
| agar | 1.00 g |
| SAG471 Antifoam (GE Silicones, SAG471) | * 0.20 mL |
| RO $H_2O$ to final vol. of | ** 1.00 L | pre-sterilisation pH was adjusted to pH 7.0 with 10M NaOH/10M $H_2SO_4$
sterilised by heating 121° C., 20-30 min (autoclaving)
Notes
* antifoam only used in seed fermenters, NOT seed flasks
** final volume adjusted accordingly to account for seed volume Trace Element Solution B

| Ingredient | Recipe |
| --- | --- |
| $FeSO_4 \cdot 7H_2O$ (Sigma, F8633) | 5.00 g |
| $ZnSO_4 \cdot 7H_2O$ (Sigma, Z0251) | 4.00 g |
| $MnCl_2 \cdot 4H_2O$ (Sigma, M8530) | 2.00 g |
| $CuSO_4 \cdot 5H_2O$ (Aldrich, 20, 919-8) | 0.20 g |
| $(NH_4)_6Mo_7O_{24}$ (Fisher scientific, A/5720/48) | 0.20 g |
| $CoCl_2 \cdot 6H_2O$ (Sigma, C2644) | 0.10 g |
| $H_3BO_3$ (Sigma, B6768) | 0.10 g |
| KI (Alfa Aesar, A12704) | 0.05 g |
| $H_2SO_4$ (95%) (Fluka, 84720) | 1.00 mL |
| RO $H_2O$ to final vol. of | 1.00 L |

SGP2 Production Medium

| Ingredient | Recipe |
| --- | --- |
| toasted soy flour (Nutrisoy) (ADM, 063-160) | 20.00 g |
| Glycerol (Fisher scientific, G/0650/25) | 40.00 g |
| MES buffer (Acros, 172595000) | 19.52 g |
| SAG471 Antifoam (GE Silicones, SAG471) | *0.20 mL |
| RO $H_2O$ to final vol. of | **1.00 L | pre-sterilisation pH adjusted to pH 6.8 with 10M NaOH sterilised by heating 121° C., 20-30 min (autoclaving)
Notes
*final volume adjusted accordingly to account for seed volume
**antifoam was used only in fermentors not flasks SM25-3 Medium (Also Termed SM25)

| Ingredient | |
| --- | --- |
| Glycerol (Fisher scientific, G/0650/25) | 40 g |
| Soy Peptone A3 SC (Organotechnie) | 10 g |
| Malt extract (Difco) | 21 g |
| to final vol. of | 1 L | pre-sterilisation pH not adjusted (i.e. pH 7.0)

ISP4 Medium

| Ingredient | |
| --- | --- |
| Soluble Starch (Difco) | 10 g |
| K2HPO4 | 1 g |
| MgSO4•7H2O | 1 g |
| NaCl | 1 g |
| (NH4)2SO4 | 2 g |
| CaCO3 | 2 g |
| ISP Trace Salts Solution | 1 mL |
| Agar | 20 g |
| to final vol. of | 1 L |

Make a paste with the starch in a small volume of cold water and bring to volume of 500 ml Add other ingredients to solution II in 500 mls water pH should be between pH 7.0 and pH 7.4 (pH 7.3) Mix two solutions together and add agar ISP Trace Salts

| Ingredient | |
| --- | --- |
| FeSO4•7H2O | 1 g |
| MnCl2•4H2O | 1 g |
| ZnSO4•7H2O | 1 g |
| to final vol. of | 1 L |

Store at 4 degrees C.

Oatmeal Agar (ISP3)

| Ingredient | Recipe |
| --- | --- |
| Oatmeal | 20.00 g |
| ISP trace element solution | 1.00 mL |
| Bacto Agar (Becton Dickinson) | 18.00 g |
| RO $H_2O$ to final vol. of | 1.00 L |

20 g oatmeal is cooked in 1 L water on a hotplate (or microwave) for 20 minutes. The cooked mixture is filtered through muslin/cheesecloth and brought to pH 7.2 and remade up to 1 L. 1 ml ISP trace elements solution is added. 18 g per L agar is then added before sterilizing.

MAM Agar

| Ingredient | Recipe |
| --- | --- |
| Wheat starch (Sigma) | 10.00 g |
| Corn steep powder (Roquette) | 2.50 g |
| Yeast extract (Becton Dickinson) | 3.00 g |
| $CaCO_3$(Calcitec) | 3.00 g |
| $FeSO_4$ (Sigma) | 0.300 g |
| Bacto Agar (Becton Dickinson) | 20.00 g |
| RO $H_2O$ to final vol. of | 1.00 L | pH 5.8 prior to autoclaving

BT6 Production Media

| Ingredient | Recipe |
| --- | --- |
| Glucose (Sigma) | 50.00 g |
| Nutrisoy (ADM) | 30.00 g |
| NaCl (Fisher) | 5.00 g |
| $(NH_4)_2SO_4$ (Sigma) | 3.00 g |
| $CaCO_3$(Calcitec) | 6.00 g |
| RO $H_2O$ to final vol. of | 1.00 L |

Adjust pH to 7.0 then add $CaCO_3$

ISP agar

| Ingredient | Recipe |
| --- | --- |
| Yeast extract (Becton Dickinson) | 4.00 g |
| Malt Extract (Becton Dickinson) | 10.0 g |
| Dextrose (Sigma) | 4.00 g |
| Bacto Agar (Becton Dickinson) | 20.0 g |
| RO $H_2O$ to final vol. of | 1.00 L |

Adjust pH to 7.3 prior to adding agar and sterilizing.

General Fermentation Method

Cryopreserved spore stocks of BIOT-4585 (for construction methodology, see Example 1) were thawed at room temperature. Vegetative cultures (seed cultures) were prepared by transferring 4.0 mL of spore stock into 400 mL medium SM25 in 2 L Erlenmeyer flasks with foam plug. Cultivation was carried out for 48 hours at 27° C. and 250 rpm (5.0 cm throw). From the seed culture 25 mL was transferred into 250 mL production medium SGP2+5% HP20 in 2 L Erlenmeyer flasks with foam plug. After 24 hours cultivation at 24° C. and 250 rpm (2.5 cm throw), 2 mL of a 250 mM racemic or 125 mM enantiomerically pure solution of the desired precursor in 1M hydrochloric acid and 2 mL of a 250 mM methanolic solution of DL-piperazic acid was added to each production flask to give a final 1 mM concentration of the individual enantiomers of the precursors. DMSO may optionally be used in place of 1M hydrochloric acid. The DL-piperazic acid may optionally be omitted. Cultivation was continued for further four days at 24° C. and 250 rpm (2.5 cm throw).

Analysis of Culture Broths by LC-UV and LC-UV-MS

Culture broth (1 mL) and ethyl acetate (1 mL) is added and mixed for 15-30 min followed by centrifugation for 10 min. 0.4 mL of the organic layer is collected, evaporated to dryness and then re-dissolved in 0.20 mL of acetonitrile.

HPLC Conditions:
018 Hyperclone BDS 018 Column 3 u, 4.6 mm×150 mm
Fitted with a Phenomenex Analytical C18 Security Guard Cartridge (KJO-4282)
Column temp at 50° C.
Flow rate 1 mL/min
Monitor UV at 240 nm
Inject 20 uL aliquot
Solvent Gradient:
0 min: 55% B
1.0 min: 55% B
6.5 min: 100% B
10.0 min: 100% B
10.05 min: 55% B
13.0 min: 55% B
Solvent A is Water+0.1% Formic Acid
Solvent B is Acetonitrile+0.1% Formic Acid
Under these conditions SfA elutes at 5.5 min
Under these conditions SfB elutes at 6.5 min LCMS is performed on an integrated Agilent HP1100 HPLC system in combination with a Bruker Daltonics Esquire 3000+ electrospray mass spectrometer operating in positive ion mode using the chromatography and solvents described above.

QC LC-MS Method
HPLC conditions:
C18 Hyperclone BDS C18 Column 3 u, 4.6 mm×150 mm
Fitted with a Phenomenex Analytical C18 Security Guard Cartridge (KJ0-4282)
Column temp at 50° C.
Flow rate 1 mL/min
Monitor UV at 210, 240 and 254 nm
Solvent Gradient:
0 min: 10% B
2.0 min: 10% B
15 min: 100% B
17 min: 100% B
17.05 min: 10% B
20 min: 10% B
Solvent A is Water+0.1% Formic Acid
Solvent B is Acetonitrile+0.1% Formic Acid
MS Conditions:
MS operates in switching mode (switching between positive and negative), scanning from 150 to 1500 amu.

In Vitro Replicon Assay for Assessment of HCV Antiviral Activity

Antiviral efficacy against genotype 1 HCV may be tested as follows: One day before addition of the test article, Huh5.2 cells, containing the HCV genotype 1b 13891uc-ubi-neo/NS3-3'/5.1 replicon (Vrolijk et al., 2003) and subcultured in cell growth medium [DMEM (Cat No. 41965039) supplemented with 10% FCS, 1% non-essential amino acids (11140035), 1% penicillin/streptomycin (15140148) and 2% Geneticin (10131027); Invitrogen] at a ratio of 1.3-1.4 and grown for 3-4 days in 75 $cm^2$ tissue culture flasks (Techno Plastic Products), were harvested and seeded in assay medium (DMEM, 10% FCS, 1% non-essential amino acids, 1% penicillin/streptomycin) at a density of 6 500 cells/well (100 μL/well) in 96-well tissue culture microtitre plates (Falcon, Beckton Dickinson for evaluation of the anti-metabolic effect and CulturPlate, Perkin Elmer for evaluation of antiviral effect). The microtitre plates are incubated overnight (37° C., 5% $CO_2$, 95-99% relative humidity), yielding a non-confluent cell monolayer.

Dilution series are prepared; each dilution series is performed in at least duplicate. Following assay setup, the microtitre plates are incubated for 72 hours (37° C., 5% $CO_2$, 95-99% relative humidity).

For the evaluation of anti-metabolic effects, the assay medium is aspirated, replaced with 75 μL of a 5% MTS (Promega) solution in phenol red-free medium and incubated for 1.5 hours (37° C., 5% $CO_2$, 95-99% relative humidity). Absorbance is measured at a wavelength of 498 nm (Safire$^2$, Tecan) and optical densities (OD values) are converted to percentage of un-treated controls.

For the evaluation of antiviral effects, assay medium is aspirated and the cell monolayers are washed with PBS. The wash buffer is aspirated, 25 μL of Glo Lysis Buffer (Cat. N°. E2661, Promega) is added after which lysis is allowed to proceed for 5 min at room temperature. Subsequently, 50 μL of Luciferase Assay System (Cat. N°. E1501, Promega) is added and the luciferase luminescence signal is quantified immediately (1000 ms integration time/well, Safire$^2$, Tecan). Relative luminescence units are converted to percentage of untreated controls.

The EC50 and EC90 (values derived from the dose-response curve) represent the concentrations at which respectively 50% and 90% inhibition of viral replication would be observed. The CC50 (value derived from the dose-response curve) represents the concentration at which the metabolic activity of the cells would be reduced to 50% of the metabolic activity of untreated cells. The selectivity index (SI), indicative of the therapeutic window of the compound, is calculated as $CC_{50}/EC_{50}$.

A concentration of compound is considered to elicit a genuine antiviral effect in the HCV replicon system when, at that particular concentration, the anti-replicon effect is above the 70% threshold and no more than 30% reduction in metabolic activity is observed.

In Vitro Replicon Assay for Assessment of HCV Antiviral Activity in Genotypes 1a and 2a The replicon cells (subgenomic replicons of genotype 1a (H77) and 2a (JFH-1)) are grown in Dulbecco's modified essential media (DMEM), 10% fetal bovine serum (FBS), 1% penicillin-streptomycin (pen-strep), 1% glutamine, 1% non-essential amino acids, 250 µg/ml G418 in a 5% $CO_2$ incubator at 37° C. All cell culture reagents may be purchased from Mediatech (Herndon, Va.).

The replicon cells are trypsinized and seeded at $5\times10^3$ cells per well in 96-well plates with the above media without G418. On the following day, the culture medium is replaced with DMEM containing compounds serially diluted in the presence of 5% FBS. The HCV replicon antiviral assay examines the effects of compounds in a serial of compound dilutions. Briefly, the cells containing the HCV replicon are seeded into 96-well plates. Test article is serially diluted with DMEM plus 5% FBS. The diluted compound is applied to appropriate wells in the plate. After 72 hr incubation at 37° C., the cells are processed. The intracellular RNA from each well is extracted with an RNeasy 96 kit (Qiagen). The level of HCV RNA is determined by a reverse transcriptase-real time PCR assay using TaqMan® One-Step RT-PCR Master Mix Reagents (Applied Biosystems, Foster City, Calif.) and an ABI Prism 7900 sequence detection system (Applied Biosystems) a as described previously (Vrolijk et al., 2003). The cytotoxic effects are measured with Taq Man® Ribosomal RNA Control Reagents (Applied Biosystems) as an indication of cell numbers. The amount of the HCV RNA and ribosomal RNA is then used to derive applicable $IC_{50}$ values (concentration inhibiting on replicon replication by 50%).

Assessment of Microsome Metabolism (Microsome Stability Assay)

Rate of Metabolism in Microsomes May be Tested as Follows:

Mouse or human liver microsomes were diluted with buffer C (0.1 M Potassium Phosphate buffer, 1.0 mM EDTA, pH 7.4) to a concentration of 2.5 mg/mL. Microsomal stability samples were then prepared by adding 50 µL of 5 µM compound spiking solution (0.5 µL 10 mM DMSO stock solution in 9.5 µL ACN, added to 990 µL Buffer C) to 50 µL of microsomal solution (2.5 mg/mL), 110 µL Buffer C and mixed well. All samples were pre-incubated for approximately 15 minutes at 37° C. Following this, the reaction was initiated by adding 40 µL of the NADPH solution (12.5 mM) with gentle mixing. Aliquots (40 µL) were removed at 0, 15, 30, 45 and 60 minutes and quenched with ACN containing internal standard (120 µL). Protein was removed by centrifugation (4000 rpm, 15 min) and the sample plate analysed for compound concentration by LC-MS/MS. Half-lives were then calculated by standard methods, comparing the concentration of analyte wth the amount originally present.

Assessment of Hepatocyte Stability

Cryopreserved hepatocytes, previously stored in liquid nitrogen are placed in a 37±1° C. shaking water bath for 2 min±15 sec. The hepatocytes are then added to 10× volume of pre-warmed Krebs-Henseleit bicarbonate (KHB) buffer (2000 mg/L glucose, no calcium carbonate and sodium bicarbonate, Sigma), mixed gently and centrifuged at 500 rpm for 3 minutes. After centrifugation, the supernatant is carefully removed and a 10× volume of pre-warmed KHB buffer added to resuspend the cell pellet. This is mixed gently and centrifuged at 500 rpm for 3 minutes. The supernatant is then removed and discarded. The cell viability and yield are then determined by cell counts, and these values used to generate human hepatocyte suspensions to the appropriate seeding density (viable cell density=$2\times10^6$ cells/mL). A 2× dosing solution is prepared in pre-warmed KHB (1% DMSO) (200 µM spiking solution: 20 µL of substrate stock solution (10 mM) in 980 µL of DMSO, 2× dosing solution: 10 µL of 200 µM spiking solution in 990 µL of KHB (2 µM after dilution).

50 µL of pre-warmed 2× dosing solution is added to the wells and 50 µL of pre-warmed hepatocyte solution ($2\times10^6$ cells/mL) added and timing started. The plate is then incubated at 37° C. 100 µL of acetonitrile containing internal standard is added to each the wells after completion of incubation time (0, 15, 30, 60 and 120 minutes) mixed gently, and 50 µL of pre-warmed hepatocyte solution added ($2\times10^6$ cells/mL). At the end of the incubation, cell viability is determined. Samples are centrifuged at 4000 rpm for 15 minutes at 4° C., supernatants diluted 2-fold with ultrapure water and compound levels analysed by LC-MS/MS.

Assessment of Water Solubility

Water solubility may be tested as follows: A 10 mM stock solution of the sanglifehrin analogue is prepared in 100% DMSO at room temperature. Triplicate 0.01 mL aliquots are made up to 0.5 mL with either 0.1 M PBS, pH 7.3 solution or 100% DMSO in amber vials. The resulting 0.2 mM solutions are shaken, at room temperature on an IKA® vibrax VXR shaker for 6 h, followed by transfer of the resulting solutions or suspensions into 2 mL Eppendorf tubes and centrifugation for 30 min at 13200 rpm. Aliquots of the supernatant fluid are then analysed by the LCMS method as described above.

Alternatively, solubility in PBS at pH7.4 may be tested as follows: A calibration curve is generated by diluting the test compounds and control compounds to 40 µM, 16 µM, 4 µM, 1.6 µM, 0.4 µM, 0.16 µM, 0.04 µM and 0.002 µM, with 50% MeOH in $H_2O$. The standard points are then further diluted 1:20 in MeOH:PBS 1:1. The final concentrations after 1:20 dilution are 2000 nM, 800 nM, 200 nM, 80 nM, 20 nM, 8 nM, 2 nM and 1 nM. Standards are then mixed with the same volume (1:1) of ACN containing internal standard (hydroxy-macrocycle, 6). The samples are centrifuged (5 min, 12000 rpm), then analysed by LC/MS.

| Solution (µL) | MeOH/$H_2O$ (1:1) (µL) | | Working solution (µM) | Solution (µL) | MeOH/buffer (1:1) (µL) | | Final solution (nM) |
|---|---|---|---|---|---|---|---|
| 10 mM 10 | 240 | → | 400 | | | | |
| 400 µM 50 | 450 | → | 40 | 20 | 380 | → | 2000 |
| 20 | 480 | → | 16 | 20 | 380 | → | 800 |
| 40 µM 50 | 450 | → | 4 | 20 | 380 | → | 200 |
| 16 µM 50 | 450 | → | 1.6 | 20 | 380 | → | 80 |
| 4 µM 50 | 450 | → | 0.4 | 20 | 380 | → | 20 |
| 1.6 µM 50 | 450 | → | 0.16 | 20 | 380 | → | 8 |
| 0.4 µM 50 | 450 | → | 0.04 | 20 | 380 | → | 2 |
| 0.04 µM 50 | 950 | → | 0.002 | 20 | 380 | → | 1 |

Test compounds are prepared as stock solutions in DMSO at 10 mM concentration. The stock solutions are diluted in duplicate into PBS, pH7.4 in 1.5 mL Eppendorf tubes to a target concentration of 100 μM with a final DMSO concentration of 1% (e.g. 4 μL of 10 mM DMSO stock solution into 396 μL 100 mM phosphate buffer). Sample tubes are then gently shaken for 4 hours at room temperature. Samples are centrifuged (10 min, 15000 rpm) to precipitate undissolved particles. Supernatants are transferred into new tubes and diluted (the dilution factor for the individual test article is confirmed by the signal level of the compound on the applied analytical instrument) with PBS. Diluted samples are then mixed with the same volume (1:1) of MeOH. Samples are finally mixed with the same volume (1:1) of ACN containing internal standard (hydroxymacrocycle, 6) for LC-MS/MS analysis.

Assessment of Cell Permeability

Cell permeability may be tested as follows: The test compound is dissolved to 10 mM in DMSO and then diluted further in buffer to produce a final 10 μM dosing concentration. The fluorescence marker lucifer yellow is also included to monitor membrane integrity. Test compound is then applied to the apical surface of Caco-2 cell monolayers and compound permeation into the basolateral compartment is measured. This is performed in the reverse direction (basolateral to apical) to investigate active transport. LC-MS/MS is used to quantify levels of both the test and standard control compounds (such as Propanolol and Acebutolol).

In Vivo Assessment of Pharmacokinetics

In vivo assays may also be used to measure the bioavailability of a compound. Generally, a compound is administered to a test animal (e.g. mouse or rat) both intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

Mice are dosed with 1, 10, or 100 mg/kg of the compound of the invention or the parent compound i.v. or p.o. . Blood samples are taken at 5, 10, 15, 30, 45, 60, 90, 120, 180, 240, 360, 420 and 2880 minutes and the concentration of the compound of the invention or parent compound in the sample is determined via HPLC. The time-course of plasma concentrations can then be used to derive key parameters such as the area under the plasma concentration-time curve (AUC—which is directly proportional to the total amount of unchanged drug that reaches the systemic circulation), the maximum (peak) plasma drug concentration, the time at which maximum plasma drug concentration occurs (peak time), additional factors which are used in the accurate determination of bioavailability include: the compound's terminal half life, total body clearance, steady-state volume of distribution and F %. These parameters are then analysed by non-compartmental or compartmental methods to give a calculated percentage bioavailability, for an example of this type of method see Egorin et al. 2002, and references therein.

In Vivo Assessment of Oral and Intravenous Pharmacokinetics (Specific Method)

For sanglifehrin analogues, whole blood is analysed. Compounds are formulated in 5% ethanol/5% cremophor EL/90% saline for both p.o. and i.v. administration. Groups of 3 male CD1 mice are dosed with either 1 mg/kg i.v. or 5 or 10 mg/kg p.o. Blood samples (40 μL) are taken via saphenous vein, pre-dose and at 0.25, 0.5, 2, 8, and 24 hours, and diluted with an equal amount of $dH_2O$ and put on dry ice immediately. Samples are stored at −70° C. until analysis. The concentration of the compound of the invention or parent compound in the sample is determined via LCMS as follows: 20 μL of blood:$H_2O$ (1:1, v/v)/PK sample is added with 20 μL Internal standard (hydroxyl macrocycle, 6) at 100 ng/mL, 20 μL working solution/MeOH and 150 μL of ACN, vortexed for 1 minute at 1500 rpm, and centrifuged at 12000 rpm for 5 min. The supernatant is then injected into LC-MS/MS. The time-course of blood concentrations is plotted and used to derive area under the whole blood concentration-time curve (AUC—which is directly proportional to the total amount of unchanged drug that reaches the systemic circulation). These values are used to generate PK parameters where possible.

In Vitro Assessment of Cytotoxicity

Huh-7 and HepG2 cells obtained from ATCC are grown in Dulbecco's modified essential media (DMEM) containing 10% fetal bovine serum (FBS), 1% penicillin-streptomycin (pen-strep) and 1% glutamine; whereas CEM cells (human T-cell leukemia cells obtained from ATCC) are grown in RPMI 1640 medium with 10% FBS, 1% pen-strep and 1% glutamine. Fresh human PBMCs are isolated from whole blood obtained from at least two normal screened donors.

Briefly, peripheral blood cells are pelleted/washed 2-3 times by low speed centrifugation and resuspension in PBS to remove contaminating platelets. The washed blood cells are then diluted 1:1 with Dulbecco's phosphate buffered saline (D-PBS) and layered over 14 mL of Lymphocyte Separation Medium (LSM; cellgrow by Mediatech, Inc.; density 1.078+/−0.002 g/ml; Cat. #85-072-CL) in a 50 mL centrifuge tube and centrifuged for 30 minutes at 600×g. Banded PBMCs are gently aspirated from the resulting interface and subsequently washed 2× with PBS by low speed centrifugation. After the final wash, cells are counted by trypan blue exclusion and resuspended at $1 \times 10^7$ cells/mL in RPMI 1640 supplemented with 15% Fetal Bovine Serum (FBS), 2 mM L-glutamine, 4 μg/mL PHA-P. The cells are allowed to incubate for 48-72 hours at 37° C. After incubation, PBMCs are centrifuged and resuspended in RPMI 1640 with 15% FBS, 2 mM L-glutamine, 100 U/mL penicillin, 100 μg/mL streptomycin, 10 μg/mL gentamycin, and 20 U/mL recombinant human IL-2.

Compound cytotoxicity is evaluated by testing half-log concentrations of each compound in triplicate against the cells described above. Cell containing medium alone served as the cell control (CC). Huh-7 and HepG2 cells are seeded in 96-well plates at a concentration of $5 \times 10^3$ cells per well. On the following day, the media is aspirated, and 100 μL of corresponding media containing 5% FBS is added. Test drug dilutions are prepared at a 2× concentration in microtiter tubes and 100 μL of each concentration is placed in appropriate wells in a standard format. After 72 hours, the cells are processed for cytotoxicity assessment.

PBMCs are diluted in fresh medium and plated in the interior wells of a 96 well round bottom microplate at $5 \times 10^4$ cells/well in a volume of 100 L. Similarly, CEM cells are plated at $1 \times 10^4$ cells/well. Then, 100 μL of 2× preparations of the test drugs are added in appropriate wells in a standard format. The cultures are maintained for six to seven days and then processed for cytotoxicity determination.

Cytotoxicity is determined using CytoTox-ONE™ homogeneous membrane integrity assay kit (Promega). The assay measures the release of lactate dehyrodgenase (LDH) from cells with damaged membranes in a fluorometric, homogeneous format. LDH released into the culture medium is measured with a coupled enzymatic assay that results in the conversion of resazurin into a fluorescent resorufin product. The amount of fluorescence produced is proportional to the number of lysed cells. Six serially diluted concentrations of each compound are applied to the cells to derive where applicable TC50 (toxic concentration of the drug decreasing cell viability by 50%) and TC90 (toxic concentration of the drug decreasing cell viability by 90%) values.

In Vitro Assessment of Inhibition of MDR1 and MRP2 Transporters

To assess the inhibition and activation of the MDR1 (P-glycoprotein 1) and MRP2 transporters, an in vitro ATPase assay from Solvo Biotechnology Inc. can be used (Glavinas et al., 2003). The compounds (at 0.1, 1, 10 and 100 µM) are incubated with MDR1 or MRP2 membrane vesicles both in the absence and presence of vanadate to study the potential ATPase activation. In addition, similar incubations are conducted in the presence of verapamil/sulfasalazine in order to detect possible inhibition of the transporter ATPase activity. ATPase activity is measured by quantifying inorganic phosphate spectrophotometrically. Activation is calculated from the vanadate sensitive increase in ATPase activity. Inhibition is determined by decrease in verapamil/sulfasalazine mediated ATPase activity.

In Vitro Assessment of Inhibition of Pgp Transporters Using MDCK Cells

To assess the inhibition of the P-glycoprotein (Pgp/MDR1) transporter, an in vitro ATPase assay from Cyprotex was used. MDR1-MDCK cells obtained from the NIH (Rockville, Md., USA) were used. Following culture, the monolayers were prepared by rinsing both basolateral and apical surfaces twice with buffer at pH 7.4 and 37° C. Cells were then incubated with pH 7.4 buffer in both apical and basolateral compartments for 40 min at 37° C. and 5% $CO_2$ with a relative humidity of 95% to stabilise physiological parameters. For the apical to basolateral study (A-B), buffer at pH 7.4 was removed from the apical compartment and replaced with loperamide dosing solutions before being placed in the 'companion' plates. The solutions were prepared by diluting loperamide in DMSO with buffer to give a final loperamide concentration of 5 µM (final DMSO concentration adjusted to 1%). The fluorescent integrity marker Lucifer yellow was also included in the dosing solution. The experiment was performed in the presence and absence of the test compound (applied to both the apical and basolateral compartments). For basolateral to apical (B-A) study, the P-glycoprotein substrate, loperamide (final concentration=5 µM) was placed in the basolateral compartment. The experiment was performed in the presence and absence of the test compound (applied to the apical and basolateral compartments). Incubations were carried out in an atmosphere of 5% $CO_2$ with a relative humidity of 95% at 37° C. for 60 min. After the incubation period, the companion plate was removed and apical and basolateral samples diluted for analysis by LC-MS/MS. A single determination of each test compound concentration was performed. On each plate, a positive control inhibitor was also screened. The test compound was assessed at 0.1, 0.3, 1, 3, 10, 30 and 50 µM. The integrity of the monolayers throughout the experiment was checked by monitoring Lucifer yellow permeation using fluorimetric analysis. After analysis, an $IC_{50}$ was calculated (i.e., inhibitor concentration (test drug) achieving half maximal inhibition effect).

In Vitro Assessment of Inhibition of Uptake Transporters

To assess the inhibition of the OAT1B1 and OAT1B3 uptake transporters, an in vitro uptake transporter assay from Solvo Biotechnology Inc. was used. Uptake experiments with Test Article (TA) at 0.068, 0.2, 0.62, 1.8, 5.5, 16.7 and 50 µM, were performed on CHO cells stably expressing human SLC transporters OATP1B1 and OATP1B3. Parental cell line CHO-K was used as negative control. Cells ($1\times10^5$ in 200 µl 1:1 mixture of Dulbecco's Modified Eagle's Medium and Ham's F-12 DMEM (F-12, Lonza, N.J., US) supplemented with 5 mM sodium butyrate) were plated on standard 96-well tissue culture plates and incubated 24 hours before the experiment at 37° C. in an atmosphere of 5% $CO_2$ and 95% air. Before experiments the medium was aspirated by vacuum suction, cells were washed with 2×100 µl of Krebs-Henseleit buffer pH 7.3 (prepared from Sigma chemicals, Sigma-Aldrich, St Louis, Mo.). Uptake experiments were carried out at 37° C. in 50 µl of Krebs-Henseleit buffer (pH 7.3) containing the probe substrate and the TA or solvent, respectively. The organic solvent concentration was equal in each well, and did not exceed 1% v/v. The probe substrate for the OATP1B1 assay was E3S (0.1 µM) and for the OATP1B3 assay was Fluo-3 (10 µM). The translocated amount of probe substrate was determined for each well in cpm. Relative activities were calculated from the equation:

$$\text{Activity}\% = (A-B)/(C-D) \times 100$$

Where A=translocated amount of substrate in the presence of TA on transfected cells, B=translocated amount of substrate in the presence of TA on parental cells, C=translocated amount of substrate in the presence of solvent on transfected cells and D=translocated amount of substrate in the presence of solvent on parental cells. $IC_{50}$ was defined as the TA concentration needed to inhibit transport of the probe substrate by 50%. $IC_{50}$ was derived from the three-parameter logistic equation; a curve fitted onto the relative activity vs. TA concentration plot by non-linear regression.

In Vitro Assessment of Inhibition of Efflux Transporters

To assess the inhibition of the MRP2, MRP3 and BSEP efflux transporters, an in vitro vesicular transporter assay from Solvo Biotechnology Inc. was used. The Test Articles (TAs) (at 0.068, 0.2, 0.62, 1.8, 5.5, 16.7 and 50 µM) were incubated with efflux transporter membrane vesicles (Solvo Biotechnology Inc.) both in the absence and presence of 4 mM ATP to distinguish between transporter mediated uptake and passive diffusion of TA's into the vesicles. In the case of MRP2 and MRP3 transporters reactions were carried out in the presence of 2 mM glutathione. Reaction mixtures were preincubated for ten minutes at 37° C. Reactions were started by the addition of 25 µl of 12 mM MgATP (4 mM final concentration in assay) or assay buffer for background controls. Reactions were stopped by adding 200 µl of ice-cold washing buffer and immediately followed by filtration on glass fiber filters in a 96-well format (filter plate). Scintillation buffer was added to the washed and dried filter plate and scintillation was counted subsequently. Probe substrates were taurocholate (2 µM) for BSEP vesicles and $E_217\beta G$ (1 µM) for MRP2 and MRP3 vesicles. For all wells the translocated amount of the probe substrate was determined in cpm units. Relative activities were calculated with the following equation: Activity %=(A−B)/(C−D)×100 Where A=translocated amount of substrate in the presence of TA and ATP, B=translocated amount of substrate in the presence of TA, C=translocated amount of substrate in the presence of solvent and ATP and D=translocated amount of substrate in the presence of solvent. $IC_{50}$ was defined as the TA concentration needed to inhibit transport of the probe substrate by 50%. $IC_{50}$ was derived from the three-parameter logistic equation; a curve fitted onto the relative activity vs. TA concentration plot by non-linear regression.

In Vitro Assay for Assessment of HIV Antiviral Activity

Antiviral efficacy against HIV may be tested as follows: Blood derived CD4+ T-lymphocytes and macrophages are isolated as described previously (Bobardt et al., 2008). Briefly, human PBMCs were purified from fresh blood by banding on Ficoll-Hypaque (30 min, 800 g, 25° C.). Primary human CD4+ T cells were purified from PBMCs by positive selection with anti-CD4 Dynabeads and subsequent release using Detachabead. Cells were cultured in RPMI medium 1640 (Invitrogen) supplemented with 10% FCS, MEM amino acids, L-glutamine, MEM vitamins, sodium pyruvate, and penicillin plus streptomycin and were subsequently activated with bacterial superantigen staphylococcal enterotoxin B (SEB; 100 ng/ml) and mitomycin C-killed PBMC from another donor (10:1 PBMC:CD4 cell ratio). Three days after stimulation, cells were split 1:2 in medium containing IL-2 (200 units/ml final concentration). Cultures were then split 1:2 every 2 days in IL-2 medium and infected with HIV at 7 days after stimulation. For generating primary human macrophages, monocytes were purified from human PBMCs by negative selection and activated and cultured at a cell concentration of 106/ml in DMEM, supplemented with 10% FCS, MEM amino acids, L-glutamine, MEM vitamins, sodium pyruvate, and penicillin (100 units/ml), streptomycin (100 mg/ml), and 50 ng/ml recombinant human granulocyte-macrophage colony-stimulating factor (GM-CSF) and maintained at 37° C. in a humidified atmosphere supplemented with 5% $CO_2$. To obtain monocyte-derived macrophages, cells were allowed to adhere to plastic and cultured for 6 days to allow differentiation.

CD4+ HeLa cells, Jurkat cells, activated CD4+ peripheral blood T-lymphocytes and macrophages (500,000 cells/100 µL) were incubated with pNL4.3-GFP(X4 virus) or pNL4.3-BaL-GFP(R5 virus) (100 ng of p24) in the presence of increasing concentrations of test article, Forty-eight hours later, infection was scored by analyzing the percentage of GFP-positive cells by FACS and $EC_{50}$ calculated.

In Vitro Assay for Assessment of HBV Antiviral Activity

Antiviral efficacy against HBV may be tested as follows: HepG2 2.2.15 cells are plated in 96-well microtiter plates. After 16-24 hours the confluent monolayer of HepG2 2.2.15 cells is washed and the medium is replaced with complete medium containing various concentrations of a test compound in triplicate (eg six half-log concentrations). Three days later the culture medium is replaced with fresh medium containing the appropriately diluted test compounds. Six days following the initial administration of the test compound, the cell culture supernatant is collected, treated with pronase and then used in a real-time quantitative TaqMan qPCR assay. The PCR-amplified HBV DNA is detected in real-time by monitoring increases in fluorescence signals that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($IC_{50}$). A dye uptake assay is then employed to measure cell viability, which is used to calculate toxicity ($TC_{50}$). The therapeutic index (TI) is calculated as $TC_{50}/IC_{50}$.

In Vitro Mixed Lymphocyte Reaction (MLR) Assay for Assessment of Immunosuppressant Activity Immunosuppressant activity was tested as follows: Peripheral blood mononuclear cell (PBMC) populations were purified from the blood of two normal, unrelated volunteer donors (A & B), using centrifugation over histopaque. Cells were counted and plated out at $1\times10^5$ cells per well in 96 well plates in RPMI media, with supplements and 2% Human AB serum. Culture conditions included: cell populations A & B alone and a mixed population of cells A&B in the absence or presence of test compounds, each at 6 different concentrations. Compounds were tested at doses ranging from 10 µM to 0.0001 µM in 1-log increments. Control wells contained a comparable concentration of vehicle (0.5% DMSO) to that present in the test compound wells. Cultures were established in triplicate in a 96 well plate and incubated at 37° C. in 5% $CO_2$ in a humidified atmosphere. 3H-thymidine was added on day 6 after assay set up and harvested 24 hrs later. The levels of proliferation between the different culture conditions were then compared.

The ability of each dilution of test compound to inhibit proliferation in the MLR was calculated as percentage inhibition. This allowed estimation of the $IC_{50}$ (concentration of test compound which resulted in a 50% reduction of counts per minute). In order to calculate the $IC_{50}$, the X axis was transformed to a log scale. Non-linear regression was used to fit to the mean data points. A sigmoidal variable slope was selected.

ELISA Analysis of Cyp-NS5A Interaction

This assay was used to measure the disruption of Cyp-NS5A complexes, which can be used to show the potency of interaction with Cyclophilin D. Briefly, production and purification of recombinant GST, GST-CypD and Con1 NS5A-His proteins was carried out as described previously (Chatterji et al., 2010). Nunc MaxiSorb 8-well strip plates were coated with GST or GST-CypD for 16 h at 4° C. and blocked. Recombinant NS5A-His (1 ng/mL) was added to wells in 50 µL of binding buffer (20 mM Tris pH 7.9, 0.5 M NaCl, 10% glycerol, 10 mM DTT and 1% NP-40) for 16 h at 4° C. Captured NS5A-His was subsequently detected using mouse anti-His antibodies (1 µg/mL) (anti-6×His, Clontech) and rabbit anti-mouse-horseradish peroxidase phosphatase (HRP) antibodies (1:1000 dilution). All experiments were conducted twice using two different batches of recombinant CypD and NS5A proteins.

Anti-PPIAse Analysis of Cyclophilin Inhibition

An alternative methodology for analysing interaction with cyclophilins is described as follows: The PPlase activity of recombinant CypA or D, produced by thrombin cleavage of GST-CypA or D, was determined by following the rate of hydrolysis of N-succinyl-Ala-Ala-Pro-Phe-p-nitroanilide by chymotrypsin. Chymotrypsin only hydrolyzes the trans form of the peptide, and hydrolysis of the cis form, the concentration of which is maximized by using a stock dissolved in trifluoroethanol containing 470 mM LiCl, is limited by the rate of cis-trans isomerization. CypA or D was equilibrated for 1 h at 5° C. with selected test article using a drug concentration range from 0.1 to 20 nM. The reaction was started by addition of the peptide, and the change in absorbance was monitored spectrophotometrically at 10 data points per second. The blank rates of hydrolysis (in the absence of CypA or D) were subtracted from the rates in the presence of CypA or D. The initial rates of the enzymatic reaction were analyzed by first-order regression analysis of the time course of the change in absorbance.

EXAMPLES

Example 1

Construction of an sfaA Deletion Mutant of *Streptomyces* sp. A92-308110 (DSM9954)

1.1 Construction of the sfaA Deletion Construct

The ~7 kb EcoRV-StuI fragment of cosmid TL3006 (SEQ ID NO. 3) encompassing sfaA (nucleotide position 14396-21362, NCBI sequence accession number FJ809786) was excised by digestion with EcoRV and StuI and the resulting isolated fragment ligated directly into pKC1139 that had previously been digested with EcoRV and treated with shrimp alkaline phosphatase (Roche). This plasmid was designated pSGK268.

An in frame deletion of the sfaA gene contained within this clone was performed using the Red/ET recombination kit supplied by Gene Bridges (catalog number K006).

```
SfaA17161f
                                                             (SEQ ID NO. 1)
5'-CGCTCTGTGGCGCCTGGTTTCCAAGCGGCTCGCGGACCGGCACCGGCACATGCATAATTA

ACCCTCACTAAAGGGCG-3'

SfaA17825r
                                                             (SEQ ID NO. 2)
5'-TGGATGTATCGTCGCAGGACGCCCAGAATTCACCTGCGACGTCCTCCAGATGCATTAATAC

GACTCACTATAGGGCTC-3'
```

Two oligonucleotides, SfaA17161f and SfaA17825r were used to amplify the neomycin marker from the FRT-PGK-gb2-neo-FRT template DNA supplied in the kit using KOD DNA polymerase. The resulting ~1.7 kb amplified product was isolated by gel electrophoresis and purified from the gel with QiaEX resin.

Plasmid pSGK268 was transformed into *E. coli* DH10B using standard techniques and selected on plates containing apramycin (50 μg/ml). Introduction of the deletion construct was performed essentially following the Gene Bridges kit protocol. A single colony was grown overnight in 2TY apramycin (50 μg/ml) and transformed with the pRedET (tet) plasmid and selected on apramycin (50 μg/ml) and tetracycline (3 μg/ml) at 30° C. A single colony was used to prepare an overnight culture of this strain in 3 ml 2TY apramycin (50 μg/ml) and tetracycline (3 μg/ml) at 30 C. 0.5 ml of this culture was used to inoculate 10 ml 2TY apramycin (50 μg/ml) and tetracycline (3 μg/ml) at 30° C. and grown to an $OD_{600nm}$ ~0.5. 1.4 ml of this culture was transferred to each of 2 eppendorf tubes and 50 μl 10% arabinose added to one tube to induce expression of the Red/ET recombination proteins. Tubes were shaken for ~1 hour at 37° C. Induced and non-induced cells were pelleted in a bench top centrifuge and washed twice with chilled sterile water; resuspending and centrifuging to pellet the cells each time. The resulting pellets were suspended in about 30-40 μl of water and kept on ice. The 1.7 kb disruption fragment isolated previously was added to the induced and non-induced tubes and transferred to 1 mm Biorad electrocuvettes on ice. The samples were electroporated (Biorad Micropulser at 1.8 kV, resulting time constant ~4 ms) and 1 ml 2TY (no antibiotics) added and mixed to remove the cells from the cuvette. Cells were incubated for ~3 hours at 37° C. with shaking (1100 rpm, eppendorf thermomixer compact) before plating onto 2TY plates containing apramycin (50 μg/ml and kanamycin 25 μg/ml and incubating over night at 37° C. Colonies from the induced sample plates were streaked onto 2TY plates containing kanamycin at 50 μg/ml to purify and confirm introduction of the kanamycin resistance cassette. PCR on individual bacterial colonies was used to confirm the introduction of the cassette. Plasmids were prepared from these cultures and digested to confirm the expected plasmid pSGK270. Plasmids were then digested with NsiI to remove the marker fragment, and the remainder religated to produce the sfaA in-frame deletion construct pSGK271.

1.2 Conjugation of *Streptomyces* sp. A92-308110 (DSM9954) and Introduction of an sfaA Deletion Plasmid pSGK271 was transformed into *E. coli* ET12567 pUZ8002 using standard techniques and selected on 2TY plates containing apramycin (50 μg/ml), kanamycin (25 μg/ml) and chloroamphenicol (10 μg/ml). The resulting strain was inoculated into 3 ml liquid 2TY containing apramycin (50 μg/ml), kanamycin (25 μg/ml) and chloroamphenicol (10 μg/ml) and incubated overnight at 37° C., 250 rpm. 0.8 ml of this culture was used to inoculate 10 ml liquid 2TY containing apramycin (50 μg/ml), kanamycin (25 μg/ml) and chloroamphenicol (10 μg/ml) in a 50 ml Falcon tube and incubated at 37° C. 250 rpm until $OD_{600nm}$ ~0.5 was reached. The resulting culture was centrifuged at 3500 rpm for 10 minutes at 4° C., washed twice with 10 ml 2TY media using centrifugation to pellet the cells after each wash. The resulting pellet was resuspended in 0.5 ml 2TY and kept on ice before use. This process was timed to coincide with the complete preparation of *Streptomyces* spores described below.

Spores of *Streptomyces* sp. A92-308110 (DSM9954) (Biot-4370) were harvested from a 1-2 week old confluent plate by resuspending in ~3 ml 20% glycerol. Spores were centrifuged (5000 rpm, 10 minutes room temperature) and washed twice with 50 mM TES buffer before resuspending in 1 ml 50 mM TES buffer and splitting between 2 eppendorf tubes. These tubes were heat shocked at 50° C. for 10 minutes in a water bath before adding 0.5 ml 2TY and incubating in an Eppendorf Thermomixer compact at 37° C. for 4-5 hours.

The prepared *E. coli* ET12567 pUZ8002 pSGK271 and Biot-4370 were mixed at ratios 1:1 (250 μL each strain) and 1:3 (100 μL *E. coli*) and immediately spread on R6 plates and transferred to a 37° C. incubator. After approximately 2 hours incubation these plates were overlaid with 2 ml of sterile water containing nalidixic acid to give a final in-plate concentration of 25 μg/L. Plates were returned to the 37° C. incubator overnight before overlaying with 2 ml of sterile water containing apramycin to give a final in-plate concentration of 20-25 μg/L. Ex-conjugant colonies appearing after ~4-7 days were patched to ISP4 media containing apramycin (25 μg/L) and nalidixic acid (25 μg/L) and incubated at 37° C. Once adequate mycelial growth was observed strains were repatched to ISP4 media containing apramycin (25 μg/L) at 37° C. and allowed to sporulate. Strains were then subcultured three times (to promote removal of the temperature sensitive plasmid) by patching to ISP4 (without antibiotic) and incubating at 37° C. for 3-4 days. Strains were finally patched to ISP4 and incubated at 28° C. to allow full sporulation (5-7 days). Spores were harvested and serially diluted onto ISP4 plates at 28° C. to allow selection of single colonies. Sporulated single colonies were doubly patched to ISP4 plates with or without apramycin (25 μg/L) to confirm loss of plasmid and allowed to grow ~7 days before testing for production of sanglifehrins.

1.3 Screening Strains for Production of Sanglifehrins in Falcon Tubes

A single ~7 mm agar plug of a well sporulated strain was used to inoculate 7 ml of sterile SM25-3 media and incubated at 27° C. 200 rpm in a 2" throw shaker. After 48 hours of growth 0.7 ml of this culture was transferred to a sterilised falcon tube containing 7 ml of SGP2 media with 5% HP20 resin. Cultures were grown at 24° C. 300 rpm on a 1 inch throw shaking incubator for 5 days before harvest. 0.8 ml bacterial culture was removed and aliquoted into a 2 ml eppendorf tube ensuring adequate dispersal of the resin in throughout the culture prior to aliquoting. 0.8 ml acetonitrile and 15 μl of formic acid were added and the tube mixed for about 30 minutes. The mixture was cleared by centrifugation and 170 μl of the extract removed into a HPLC vial and analysed by HPLC.

1.4 Analysis of Strains for Reversion to Wild Type or sfaA Phenotype.

Extracts of strains were analysed by HPLC. Strains that produced sanglifehrin A and B were not analysed further as these had reverted to wild type. Strains lacking sanglifehrin A and B production showed small levels (~1-2 mg/L) of a peak retention time 6.5 minutes that displayed a sanglifehrin like chromophore. Analysis by LCMS indicated this peak had a m/z 1073, −16 units from the expected m/z of sanglifehrin. It was postulated this peak was due to incorporation of phenylalanine in absence of meta-hydroxytyrosine.

Eight strains showing loss of sanglifeherin production were subsequently regrown to assess whether the potential sfaA mutation could be complemented chemically allowing a mutasynthetic process to novel sanglifehrins. Strains were grown in SM25-3 seed media for 48 hours before transferring to SGP2 production media with 5% resin. After a further 24 hours growth strains were fed in triplicate with 2 mM DL meta-hydroxytyrosine (addition of 100 ul of a 0.16M solution in 1M HCL) or 2 mM L-phenylalanine with an unfed strain used as control. Strains were also fed pipecolic acid (2 mM) in methanol) to enhance product yields. Strains were harvested after a further 4 days growth and extracted and analysed by HPLC. Meta-hydroxy tyrosine was shown to completely complement the sfaA mutation and addition of L-phenylalanine increased levels of the −16 amu compound. Strain Biot-4585 was chosen for further study as the sfaA deletion mutant.

Example 2

Other Methods for Construction of the sfaA Deletion Construct

Other methods can be used to generate sfaA deletion mutants. Examples include sfaA insertional inactivation mutants (such as example 12 from WO2010/034243). This strain was generated as described in WO2010/034243, and given the strain designation BIOT-4452.

In an alternative procedure to generate the deletion of sfaA two oligonucleotides 15209F 5'-CAGAGAATTCGCGG-TACGGGGCGGACGACAAGGTGTC-3' (SEQ ID NO. 4) and 17219R 5'-GCGCATGCATGTGCCGGTGCCGGTC-CGCGAGCCGCTTGG-3' (SEQ ID NO. 5) are used to amplify an upstream region of homology using cosmid TL3006 (SEQ ID NO. 3) as template and KOD DNA polymerase. The amplified product is treated with T4 polynucleotide kinase (NEB) and cloned into pUC18 that has been dephosphorylated by treating with shrimp alkaline phosphatase (Roche). The resulting construct is checked by restriction digestion and thoroughly sequenced to ensure the desired sequence is generated and that errors have not been introduced during polymerase amplification. This construct is digested with EcoRI and NsiI and the products analysed by gel electrophoresis. The desired sequence-containing band (i.e. upstream homology ~2 kb) is excised from the gel and purified using standard procedures (QiaEX resin). A second series of oligonucleotides: 17766F 5'-CCTCATGCATCTGGAGGACGTCGCAGGT-GAATTCTGGGCG-3' (SEQ ID NO. 6) and 19763R 5'-GGGCAAGCTTCTCCTGGCTGAGCTTGAACATCG-3' (SEQ ID NO. 7) are used to amplify a downstream region of homology using cosmid TL3006 (SEQ ID NO. 3) as template and KOD DNA polymerase. The amplified product is treated with T4 polynucleotide kinase (NEB) and cloned into pUC18 that has been dephosphorylated by treating with shrimp alkaline phosphatase (Roche). The resulting construct is analysed by restriction digestion and thoroughly sequenced to ensure the desired sequence is generated and that errors have not been introduced during polymerase amplification. This construct is digested with HindIII and NsiI and the products analysed by gel electrophoresis. The desired sequence-containing band (i.e. downstream homology ~2 kb) is excised from the gel and purified using standard procedures (QiaEX resin). Vector pKC1139 is digested with EcoRI and HindIII and the large vector fragment isolated by gel electrophoresis and purified by standard methods (QiaEX resin). The isolated upstream and downstream homology fragments are then cloned into this fragment of pKC1139 in a three-way ligation to generate the desired sfaA deletion construct.

In a further alternative procedure for generation of a sfaA deletion construct commercial gene synthesis (i.e. Genscript or other vendor) is used to generate a construct containing the desired sequence (SEQ ID NO. 8). This purchased construct is digested using BamHI and XbaI to excise the sequence of interest and the products analysed by gel electrophoresis. The desired sequence-containing band (~4 kb) is excised from the gel and purified using standard procedures. Vector pKC1139 is digested with BamHI and XbaI and the large fragment isolated by gel electrophoresis and purified by standard methods. The two isolated fragments are then ligated together to generate the desired sfaA deletion construct.

These alternative sfaA deletion constructs are introduced into *Streptomyces* sp. A92-308110 (DSM9954) by conjugation and selection for the secondary cross using the methods described in Example 1.2. Growth and analysis of strains constructed in this way also follows the methods described in Example 1.2

Example 3

Array Feed of the sfaA Deletion Mutant

Spore stocks of a mutant disrupted in sfaA (BIOT-4452 or BIOT-4585) were prepared after growth on MAM, ISP4, ISP3 or ISP2 medium, and preserved in 20% w/v glycerol in distilled water and stored at −80° C. Vegetative cultures (seed cultures) were prepared by inoculating spore stock (1% v/v) into 7 mL seed medium (SM25 medium) in 50 mL centrifuge tubes with foam plugs. The culture tubes were incubated at 27° C., 250 rpm (5 cm throw) for 48 h. From the seed culture 10% (v/v) was transferred into 7 mL production medium SGP-2 in 50 mL centrifuge tubes with foam plugs. Cultivation was carried out at 24° C. and 300 rpm (2.5 cm throw). For production of sanglifehrin mutasynthetic analogues, 0.05 mL of a 0.32 M solution (in 1N HCl) of the feed compound (mutasynthon) was added to each tube at 24 hours post inoculation to give a final concentration of 2 mM. Additionally, 0.05 ml of a 0.32 M solution of piperazic acid (in methanol) was added to each tube at 24 hours to give a final concentration of 2 mM. Cultivation was continued for an additional four days post feeding.

Samples were extracted by transferring 0.8 ml of the whole broth into a 2 ml capped eppendorf tube. 0.8 ml of acetonitrile was added, along with 0.015 ml of formic acid. The mixture was then shaken for 30 minutes on a vibrax. The tube was then centrifuged at 13000 rpm for 10 minutes and 0.15 ml of the supernatant was removed for analysis. Extracts were analysed as described in general methods.

Table 1 shows the mutasynthons that were fed in this way, along with the LCMS H+ and Na+ adducts, anticipated molecular mass and retention time of the sanglifehrin mutasynthetic products observed. The major peaks, relating to the sanglifehrin A analogues, are shown. In all cases, LCMS peaks were also seen for the sanglifehrin B analogues (Mass—18).

TABLE 1

| mutasynthon fed | mutasynthon name | $[M - H]^-$ observed (m/z) | $[M + Na]^+$ observed (m/z) | molecular mass (amu) | retention time (minutes) |
|---|---|---|---|---|---|
| (HO, F on phenyl, CO2H, NH2) | 2-amino-3-(4-fluoro-3-hydroxyphenyl)propanoic acid | 1106.4 | 1130.4 | 1107.4 | 5.5 |
| (HO, F on phenyl, CO2H, NH2) | 2-amino-3-(3-fluoro-5-hydroxyphenyl)propanoic acid | 1106.4 | 1130.4 | 1107.4 | 5.7 |
| (HO, F on phenyl, CO2Me, NH2) | methyl 2-amino-3-(3-fluoro-5-hydroxyphenyl)proprionate | 1106.4 | 1130.4 | 1107.4 | 5.7 |
| (HO, Me on phenyl, CO2Me, NH2) | methyl (S)-2-amino-3-(3-hydroxy-4-methylphenyl)propanoate | 1102.5 | 1126.7 | 1103.5 | 6.0 |
| (F on phenyl, CO2H, NH2) | 2-amino-3-(3-fluorophenyl)propanoic acid | 1090.4 | 1114.5 | 1091 | 6.1 |
| (pyridone, CO2Me, NH2) | methyl (2S)-2-amino-3-(3-hydroxy(2-pyridyl))propanoate | 1089.5 | 1113.7 | 1090.5 | 4.4 |
| (HO, F on phenyl, CO2Me, NH2) | methyl 2-amino-3-(2-fluoro-5-hydroxyphenyl)propanoate | 1106.5 | 1130.6 | 1107.5 | 5.5 |
| (F, HO on phenyl, CO2Me, NH2) | methyl 2-amino-3-(2-fluoro-3-hydroxyphenyl)propanoate | 1106.5 | 1130.6 | 1107.5 | 5.1 |
| (F, HO, F on phenyl, CO2Me, NH2) | methyl 2-amino-3-(2,6-difluoro-3-hydroxyphenyl)propanoate | 1124.4 | 1148.5 | 1125.5 | 5.1 |

Example 4

Isolation of 63-Fluoro Sanglifehrin A, Intermediate Compound 14

Fermentation carried out as described in general methods utilising methyl 2-amino-3-(3-fluoro-5-hydroxyphenyl)propanoate and DL-piperazic acid as precursors, both were added at 26 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using a magnetic stirrer. The acetonitrile extract was recovered either by centrifugation or by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (1.3 g).

The crude extract (1.3 g) was dissolved in ethyl acetate (2 ml) and loaded onto a silica gel column (10×2 cm) conditioned with ethyl acetate (500 ml). The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (278 mg) was dissolved in methanol (1.8 ml) and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (20 mg).

Example 5

Isolation of 62,63-Fluoro Sanglifehrin A, Intermediate Compound 15

Fermentation carried out as described in general methods utilising methyl (S)-2-amino-3-(3,4-difluoro-5-hydroxyphenyl)propanoate and DL-piperazic acid as precursors, both were added at 26 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using a magnetic stirrer. The acetonitrile extract was recovered either by centrifugation or by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (1.6 g).

The crude extract (1.6 g) was dissolved in 2 ml ethyl acetate and loaded onto a silica gel column (10×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (188 mg) was dissolved in 1.8 ml methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. These fractions were taken to dryness under reduced pressure to yield the target compound as an off-white amorphous solid (15 mg).

Example 6

Isolation of 62-Fluoro Sanglifehrin A, Intermediate Compound 16

Employed methyl (S)-2-amino-3-(4-fluoro-3-hydroxyphenyl)propanoate and DL-piperazic acid precursors. Carried out in accordance with general method with exception that precursors were added at 27 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using magnetic stirrer. The acetonitrile extract was recovered either by centrifugation or by allowing it to settle under gravity. A second acetonitrile extraction of the cells and resin was then performed under the same conditions.

The combined acetonitrile extracts were concentrated to a residual aqueous volume under reduced pressure and then adjusted to pH 6. This was extracted twice with ethyl acetate and the combined organics taken to dryness under reduced pressure to give the final oily crude (4.2 g).

The crude extract (4.2 g) was dissolved in 4 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (390 mg) was dissolved in 2.4 ml methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (38 mg).

Example 7

Isolation of 62-Methyl Sanglifehrin A, Intermediate Compound 17

Cryopreserved spore stocks of BIOT-4585 were thawed at room temperature. Vegetative cultures (seed cultures) were prepared by transferring 0.4 mL of spore stock into 400 mL medium SM25 in 2 L Erlenmeyer flasks with foam plug. Cultivation was carried out for 48 hours at 27° C. and 250 rpm (2.5 cm throw). From the seed culture 20 mL was transferred into 400 mL production medium SGP2+5% HP20 in 2 L Erlenmeyer flasks with foam plug. After 24 hours cultivation at 24° C. and 250 rpm (2.5 cm throw), 2 mL of a 200 mM solution of methyl (S)-2-amino-3-(3-hydroxy-4-methylphenyl)propanoate in 1M hydrochloric acid and 2 mL of a 400 mM methanolic solution of DL-piperazic acid was added to each production flask to give a final 1 mM concentration of the individual enantiomers of the precursors. Cultivation was continued for further four days at 24° C. and 250 rpm (2.5 cm throw).

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (7.6 g).

The crude extract (7.6 g) was dissolved in 5 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (319 mg) was dissolved in 2.4 ml methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (14.9 mg).

Example 8

Isolation of 61-Deshydroxy Sanglifehrin A, Intermediate Compound 18

Cryopreserved spore stocks of BIOT-4585 were thawed at room temperature. Vegetative cultures (seed cultures) were prepared by transferring 0.4 mL of spore stock into 400 mL medium SM25 in 2 L Erlenmeyer flasks with foam plug. Cultivation was carried out for 48 hours at 27° C. and 250 rpm (2.5 cm throw). From the seed culture 500 mL was transferred into 4.5 L production medium SGP2+5% HP20 in a 7 L Applikon fermenter and cultivated at 24° C., 400 rpm (cascade DOT control), 2.5 L/min air flow and 30% DOT (cascade agitation control). After 24 hours cultivation, 7.5 mL of a 667 mM solution of (S)-2-amino-3-phenylpropanoic acid in 1M hydrochloric acid was added to the fermenter to give a final 1 mM concentration of the precursor. Cultivation was continued for further four days at 24° C., 400 rpm (cascade DOT control), 2.5 L/min air flow and 30% DOT (cascade agitation control).

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered by allowing it to settle under gravity. A second acetonitrile extraction of the cells and resin was then performed under the same conditions, but with the second extract being recovered by centrifugation. The combined acetonitrile extracts were concentrated to a residual aqueous volume under reduced pressure and then adjusted to pH 6. This was extracted twice with ethyl acetate and the combined organics taken to dryness under reduced pressure to give the final crude (55 g).

The crude extract (55 g) was suspended in 80% methanol in water and extracted with 300 ml hexane twice. The target compound was found in methanol/water part and which were taken to dryness. This dried extract (48 g) dissolved in 30 ml ethyl acetate and loaded onto a silica gel column (20×5 cm) conditioned with 1 L ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (813 mg) was dissolved in methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (34 mg).

Example 9

Isolation 58-des(3-hydroxyphenyl)-58-(3-hydroxy(2-pyridyl)-sanglifehrin A, intermediate compound 19

Employed methyl (2S)-2-amino-3-(3-hydroxy(2-pyridyl)) propanoate and DL-piperazic acid precursors. Carried out in accordance with general method with exception that the incubator throw during vegetative (seed) cultivation was 2.5 cm.

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (7 g).

The crude extract (7 g) was dissolved in 4 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate to 100% acetone then 1% methanol to stepwise 5% methanol in acetone). Approx. 250 mL fractions were collected and the target compound identified by analytical LC, combined and taken to dryness. This material (204 mg) was dissolved in methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (4 mg).

Example 10

Isolation of 61-Deshydroxy-61-Fluoro Sanglifehrin A Intermediate Compound 20

Cryopreserved spore stocks of BIOT-4585 were thawed at room temperature. Vegetative cultures (seed cultures) were prepared by transferring 0.4 mL of spore stock into 400 mL medium SM25 in 2 L Erlenmeyer flasks with foam plug. Cultivation was carried out for 48 hours at 27° C. and 250 rpm (2.5 cm throw). From the seed culture 20 mL was transferred into 400 mL production medium SGP2+5% HP20 in 2 L Erlenmeyer flasks with foam plug. After 24 hours cultivation at 24° C. and 250 rpm (2.5 cm throw), 2 mL of a 400 mM solution of 2-amino-3-(3-fluorophenyl)propanoic acid in 1M hydrochloric acid and 2 mL of a 400 mM methanolic solution of DL-piperazic acid was added to each production flask to give a final 1 mM concentration of the individual enantiomers of the precursors. Cultivation was continued for further four days at 24° C. and 250 rpm (2.5 cm throw).

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered either by allowing it to settle under gravity. A second acetonitrile extraction of the cells and resin was then performed under the same conditions. A third extract was obtained by centrifugation of the residual cell and resin mix. The combined acetonitrile extracts were concentrated to a residual aqueous volume under reduced pressure and then adjusted to pH 6. This was extracted twice with ethyl acetate and the combined organics taken to dryness under reduced pressure to give the final crude (10.5 g).

The crude extract (10.5 g) was dissolved in 7 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (342 mg) was dissolved in methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 53% B for 30 minutes following the injection. Pure fractions were identified by HPLC-UV and combined. These fractions were taken to dryness under reduced pressure to yield the target compound as an off-white amorphous solid (6 mg).

Example 11 synthesis of diethyl (2-(1,2-oxazinan-2-yl)-2-oxoethyl)phosphonate

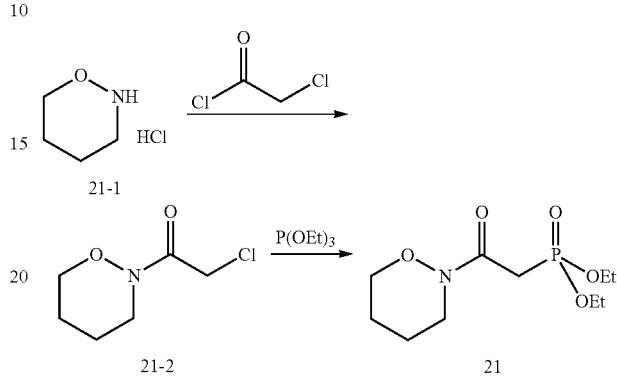

To a solution of 21-1 (ChemCollect, Germany)(100 mg, 0.81 mmol), Et₃N (246 mg, 2.43 mmol) in dry DCM (5 mL) was added dropwise chloroacetyl chloride (138 mg, 1.22 mmol). The reaction mixture was stirred at room temperature for 3 h, poured into ice water, and extracted with ethyl acetate. The organic layer was washed with brine and dried over Na₂SO₄, filtered, concentrated in vacuo. The residue (21-2) was used to the next step without any further purification. (123 mg, 90% yield).

A mixture of 21-2 (123 mg, 0.75 mmol) and triethyl phosphite (250 mg, 1.50 mmol) were stirred at 140° C. for 6 h. The reaction mixture was cooled to room temperature and was purified by flash chromatography to yield 21.

Alternative synthesis of synthesis of diethyl (2-(1,2-oxazinan-2-yl)-2-oxoethyl)phosphonate, 21

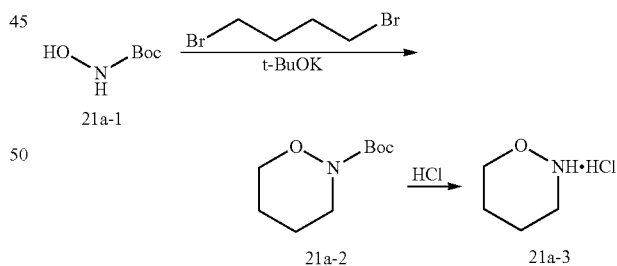

General Procedure for Preparation of 21a-2

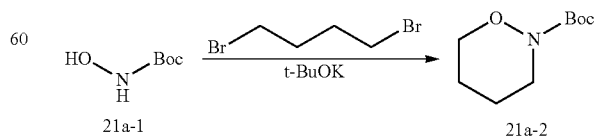

To a solution of t-BuOK (84.0 g, 0.75 mol) in tetrahydrofuran (2.0 L) was added 21a-1 (50.0 g, 0.38 mol) portion-wise at room temperature. the mixture was stirred for 1 h at room temperature. 1,4-Dibromobutane (81.2 g, 0.38 mol) was added dropwise at room temperature. Then the mixture was stirred at 80° C. for 16 h. After cooling down, water (2000 mL) was added, the mixture was extracted with ethyl acetate (2×1000 mL). The combined organic later was dried over anhydrous Na$_2$SO$_4$ for 16 h, after filtration and concentration, the residue was purified by silica-gel column chromatography (eluent: petroleum ether:ethyl acetate=100:1 to 10:1) to give 21a-2 (57 g) as a colorless oil.

General Procedure for Preparation of 21a-3

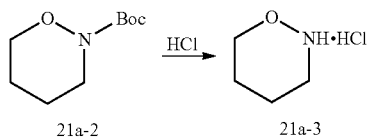

To a solution of 21a-2 (55 g, 0.29 mol) in tert-butyl methyl ether, TBME (80 mL) was added a solution of 4N HCl (600 ml, in TBME) at room temperature, the mixture was stirred for 3 h at room temperature. The precipitated solid was filtered and washed with TBME (50 mL) to give 21a-3 (30 g) as a white solid.

General Procedure for Preparation of 21

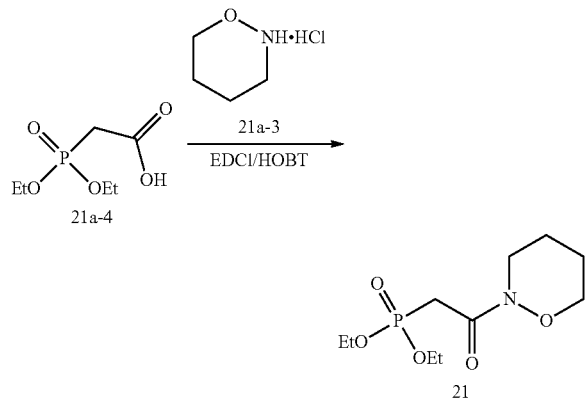

To a stirred solution of 21a-4 (35 g, 0.18 mol), hydroxybenzotriazole (HOBT) (29 g, 0.21 mol) and Et$_3$N (71 mL, 0.51 mol) in anhydrous dichloromethane (550 mL) was added 1-Ethyl-3-(3-dimethylaminopropyl)carbodiimide (EDCI) (41 g, 0.21 mol) portion-wise at 0° C. The reaction mixture was stirred at 0° C. for 0.5 h, then 21a-3 (24 g, 0.20 mol) was added at 0° C. and stirred for 16 h. Then TLC (petroleum ether/ethyl acetate: 3/1) showed that the reaction was complete. At this time the reaction mixture was slowly poured into water (500 mL) with vigorous stirring. The mixture was extracted with dichloromethane (2×200 mL). The combined organic layer was washed with brine (2×100 mL), dried with Na$_2$SO$_4$, filtered and concentrated to afford crude product. Chromatography (petroleum ether/ethyl acetate, 100:1 to 10:1) gave 21 (38 g) as a yellow oil.

Example 12 synthesis of diethyl (2-oxo-2-(pyridin-2-ylamino)ethyl)phosphonate

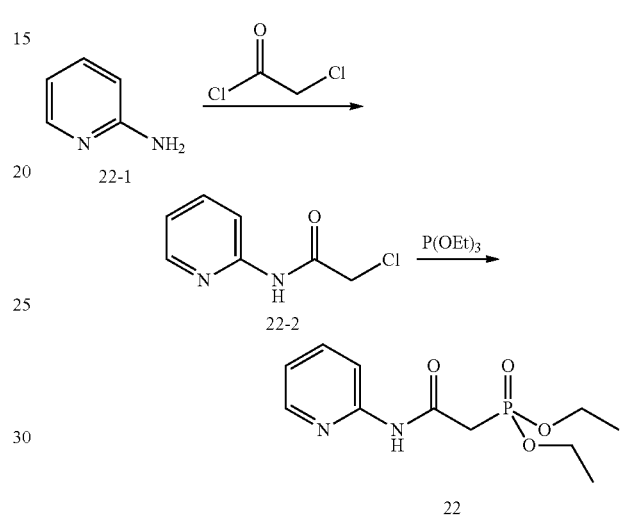

To a solution of 22-1 (1 g, 10.6 mmol), Et$_3$N (1.075 g, 10.6 mmol) in dry methylene chloride (50 mL) was added dropwise chloroacetyl chloride (1.2 g, 10.6 mmol). The reaction mixture was stirred at room temperature for 3 h, poured into ice water, and extracted with ethyl acetate. The organic layer was washed with brine and dried over Na$_2$SO$_4$, filtered and concentrated in vacuo. The residue was purified by reversed phase-combiflash to yield 22-2.

A mixture of 22-2 (170 mg, 1.00 mmol) and triethyl phosphite (332 mg, 2.00 mmol) was stirred at 140° C. for 6 h. The reaction mixture was cooled to room temperature and was purified by flash chromatography to yield 22.

Example 13

Preparation of Compound 23

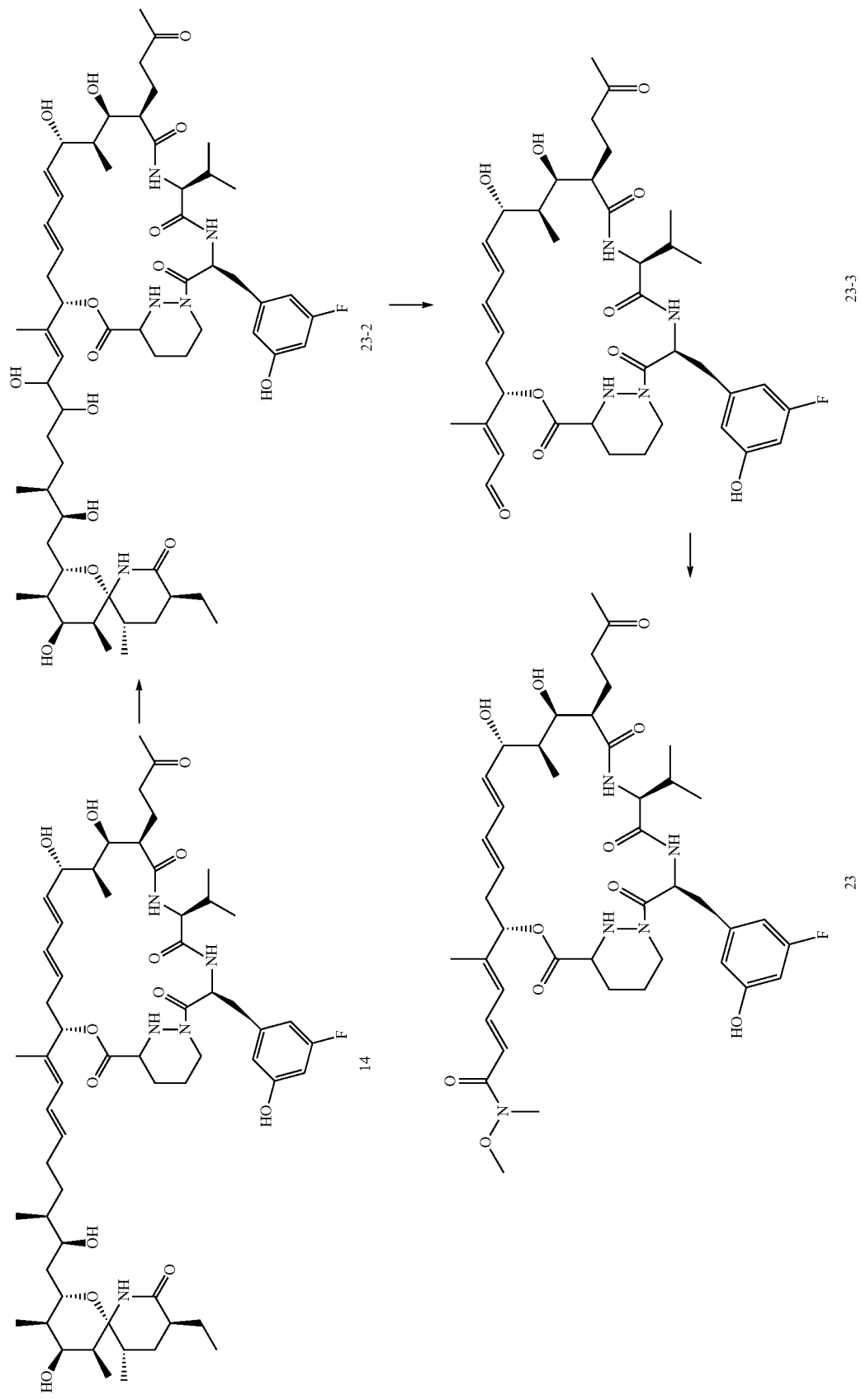

To a stirred solution of 14 (430 mg, 0.38 mmol), (DHQ)$_2$PHAL (18.6 mg, 0.024 mmol), osmium tetroxide (0.156 mL, 0.012 mmol) in tert-butyl alcohol (2.5 wt %, 0.079 mmol/ml), and methanesulfonamide (74 mg, 0.77 mmol) in 20 mL tert-butyl alcohol were added at room temperature, a solution of potassium ferricyanide (382 mg, 1.16 mmol) and potassium carbonate (160 mg, 1.16 mmol) in 20 mL water, resulting in a brown emulsion. After 2 h a solution of sodium sulfite was added, and stirring was continued for 20 min. The resulting mixture was extracted with ethyl acetate (3×50 ml). The combined organic layers were washed with brine, dried over anhydrous sodium sulfate, filtered, and concentrated under reduced pressure, purified by reverse-phase flash chromatography to yield 23-2 as a white solid.

To a stirred solution of 23-2 (240 mg, 0.21 mmol) in 24 mL of a 2:1 mixture of THF and water was added sodium periodate (91 mg, 0.42 mmol). The resulting mixture was stirred at room temperature for 3 h, and then saturated aqueous sodium bicarbonate was added. This mixture was extracted with three portions of ethyl acetate. The combined organic layers were washed with one portion of water and two portions of saturated brine, dried over anhydrous sodium sulfate, filtered, and concentrated under reduced pressure. The residue was purified by reverse-phase flash chromatography to yield 23-3.

To a solution of diethyl (2-(methoxy(methyl)amino)-2-oxoethyl)phosphonate (91 mg, 0.368 mmol) in THF (5.0 mL) was added NaH (2.8 mg, 0.1104 mmol) in anhydrous THF (0.2 mL) at 0° C. with stirring. The solution was then stirred at 20° C. until it became clear. Then 23-3 (70 mg, 0.092 mmol) was added to the clear solution and the mixture stirred at 20° C. for 2 h. The mixture was quenched with water (10 mL) and extracted with ethyl acetate (3×30 mL). The organic layer was washed with brine and dried over Na$_2$SO$_4$, filtered and reduced in vacuo. The residue was purified by preparative HPLC to obtained 23 as a white solid.

Example 14

Preparation of Compound 24

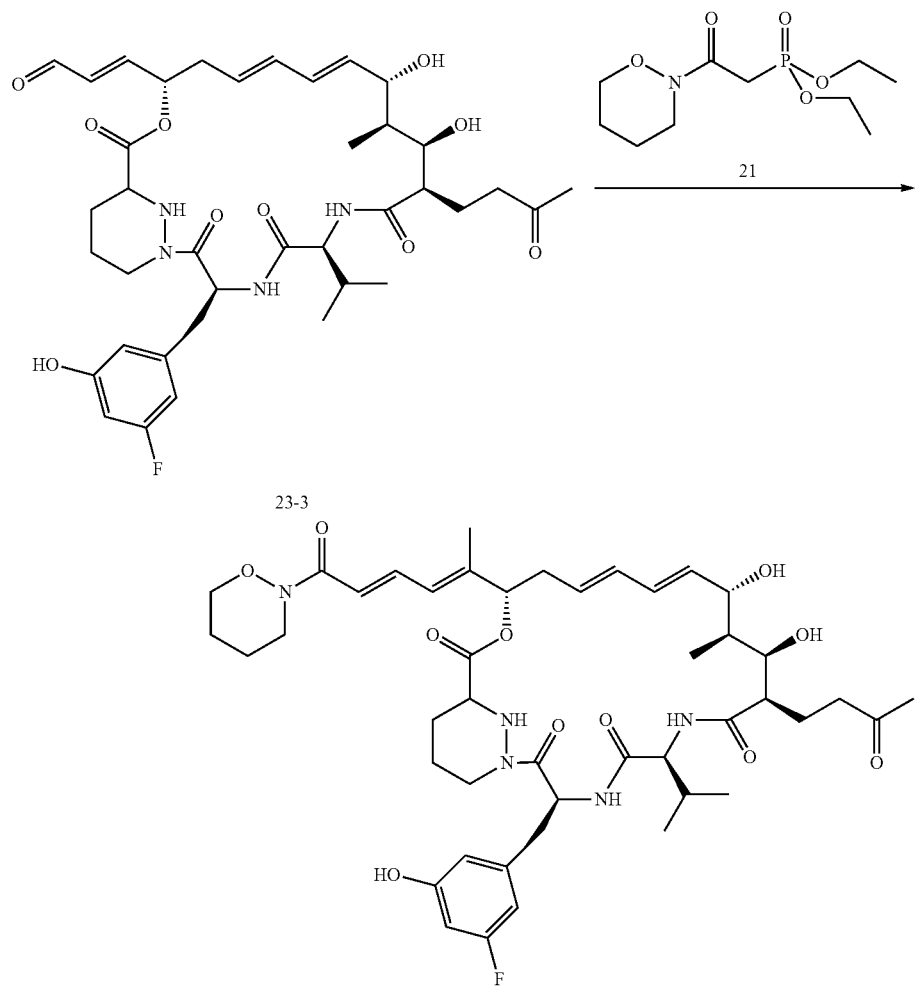

To a solution of 21 (42 mg, 0.168 mmol) in THF (2.0 mL) was added NaH (1.2 mg, 0.05 mmol) in anhydrous THF (0.2 mL) at 0° C. with stirring. The solution was then stirred at 20° C. until it became clear. Then 23-3 (30 mg, 0.042 mmol) was added to the clear solution and the mixture stirred at 20° C. for 2 h. The mixture was quenched with water (10 mL) and extracted with ethyl acetate (3×20 mL). The organic layer was washed with brine and dried over Na$_2$SO$_4$, filtered and reduced in vacuo. The residue was purified by preparative HPLC to obtained 24 as a white solid.

Example 15

Preparation of Compound 25

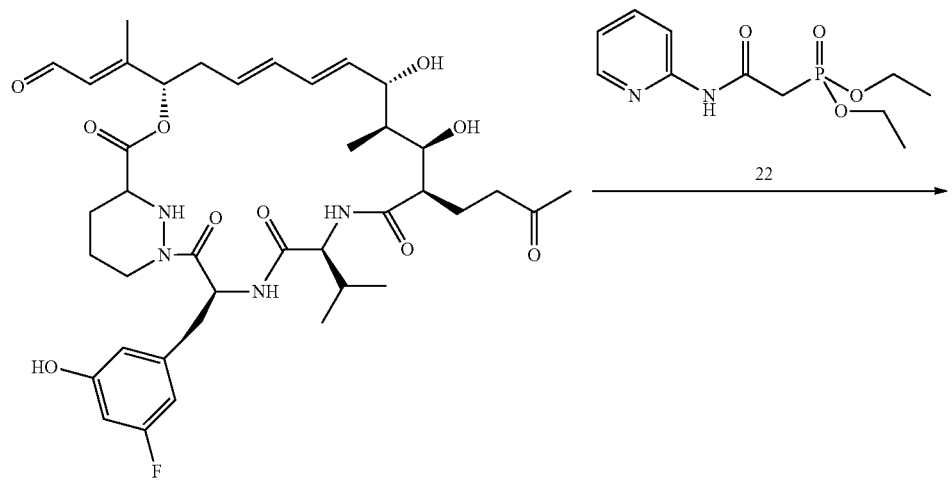

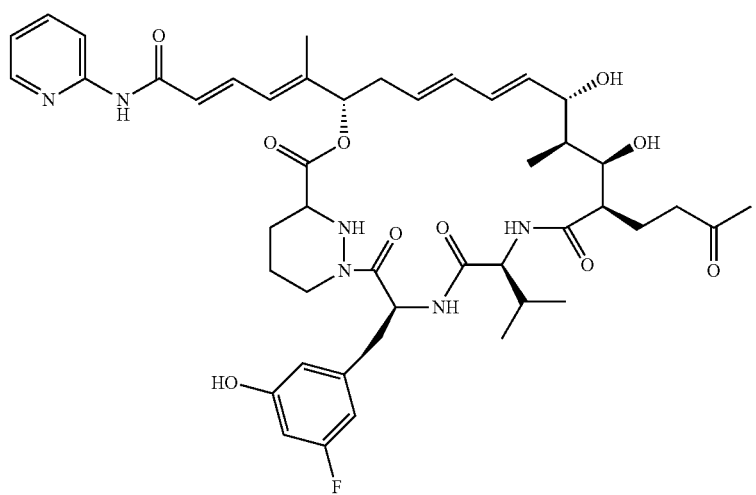

To a solution of 22 (48 mg, 0.168 mmol) in THF (2.0 mL) was added NaH (1.2 mg, 0.05 mmol) in anhydrous THF (0.2 mL) at 0° C. with stirring. The solution was then stirred at 20° C. until it became clear. Then 23-3 (30 mg, 0.042 mmol) was added to the clear solution and the mixture stirred at 20° C. for 2 h. The mixture was quenched with water (10 mL) and extracted with ethyl acetate (3×20 mL). The organic layer was washed with brine and dried over $Na_2SO_4$, filtered and reduced in vacuo. The residue was purified by preparative HPLC to obtained 25 as a white solid.

Example 16

Preparation of Compound 26

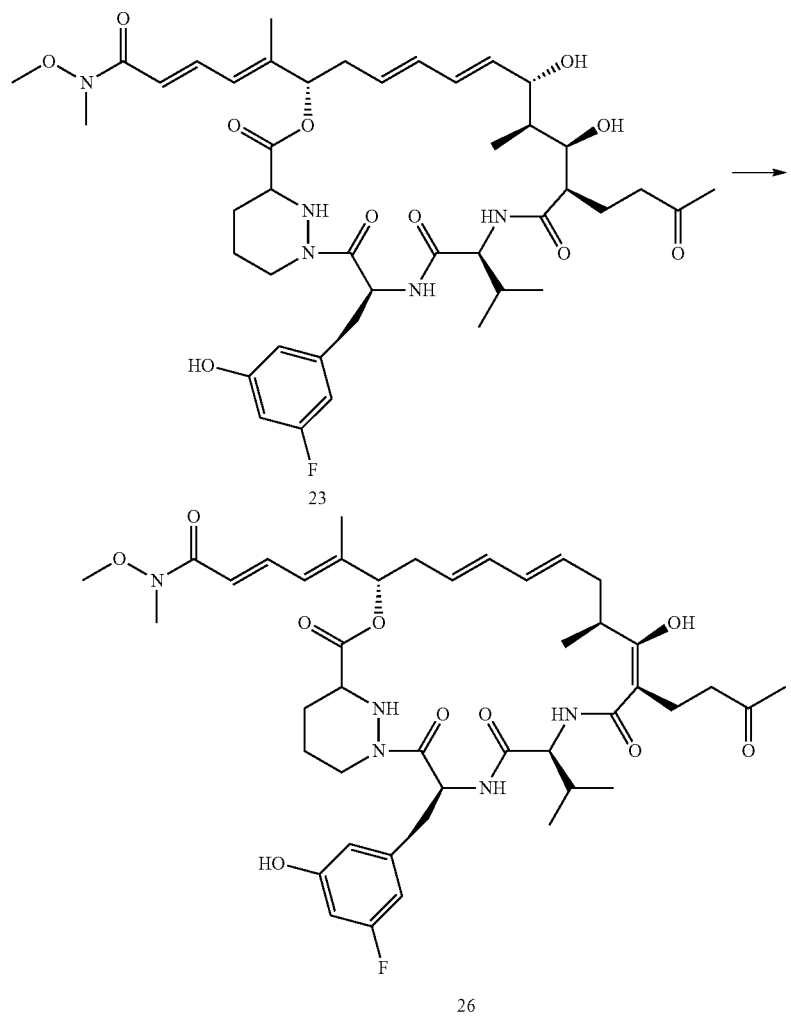

To a solution of 23 (13 mg, 0.015 mmol) dissolved in dioxane (1 mL) was added aqueous HCl solution (2 M, 0.080 ml, 0.16 mmol). The reaction was stirred at 20° C. for 24 h and the reaction was quenched with water and extracted with ethyl acetate (3×10 mL). The organic phase was dried over sodium sulfate and evaporated. The residue was purified by preparative HPLC to obtained 26 as a white solid.

Example 17

Preparation of Compound 27

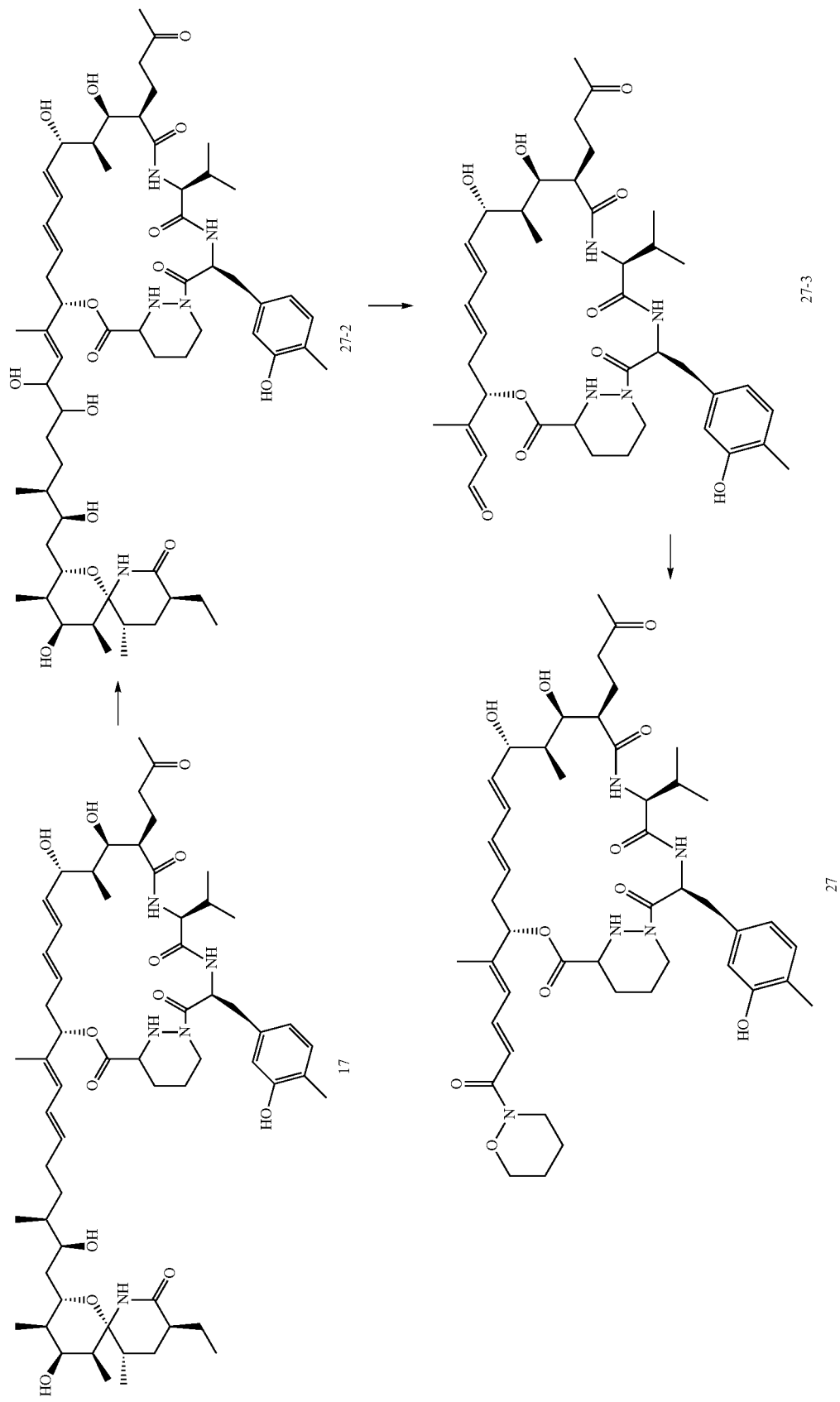

To a stirred solution of 17 (99 mg, 0.09 mmol), (DHQ)₂PHAL (4.2 mg, 0.0054 mmol), osmium tetroxide (0.034 mL, 0.0027 mmol) in tert-butyl alcohol (2.5 wt %, 0.079 mmol/ml), and methanesulfonamide (18 mg, 0.18 mmol) in 5 mL tert-butyl alcohol were added at room temperature, a solution of potassium ferricyanide (90 mg, 0.27 mmol) and potassium carbonate (37 mg, 0.27 mmol) in 5 mL water, resulting in a brown emulsion. After 2 h a solution of sodium sulfite was added, and stirring was continued for 20 min. The resulting mixture was extracted with ethyl acetate (3×20 ml). The combined organic layers were washed with brine, dried over anhydrous sodium sulfate, filtered, and concentrated under reduced pressure, purified by reverse-phase flash chromatography to yield 27-2 as a white solid.

To a stirred solution of 27-2 (40 mg, 0.035 mmol) in 3 mL of a 2:1 mixture of THF and water was added sodium periodate (15 mg, 0.07 mmol). The resulting mixture was stirred at room temperature for 3 h, and then saturated aqueous sodium bicarbonate was added. This mixture was extracted with three portions of ethyl acetate. The combined organic layers were washed with one portions of water and two portions of saturated brine, dried over anhydrous sodium sulfate, filtered, and concentrated under reduced pressure. The residue was purified by reverse-phase flash chromatography to yield 27-3 as a white solid To a solution of 21 (28 mg, 0.104 mmol) in THF (2.0 mL) was added NaH (0.75 mg, 0.0312 mmol) in anhydrous THF (0.2 mL) at 0° C. with stirring. The solution was then stirred at 20° C. until it became clear. Then 27-3 (19.6 mg, 0.026 mmol) was added to the clear solution and the mixture stirred at 20° C. for 2 h. The mixture was quenched with water (10 mL) and extracted with ethyl acetate (3×10 mL). The organic layer was washed with brine and dried over Na₂SO₄, filtered, and concentrated under reduced pressure. The residue was purified by preparative HPLC to obtained 27 as a white solid.

Example 18

Preparation of Compound 28

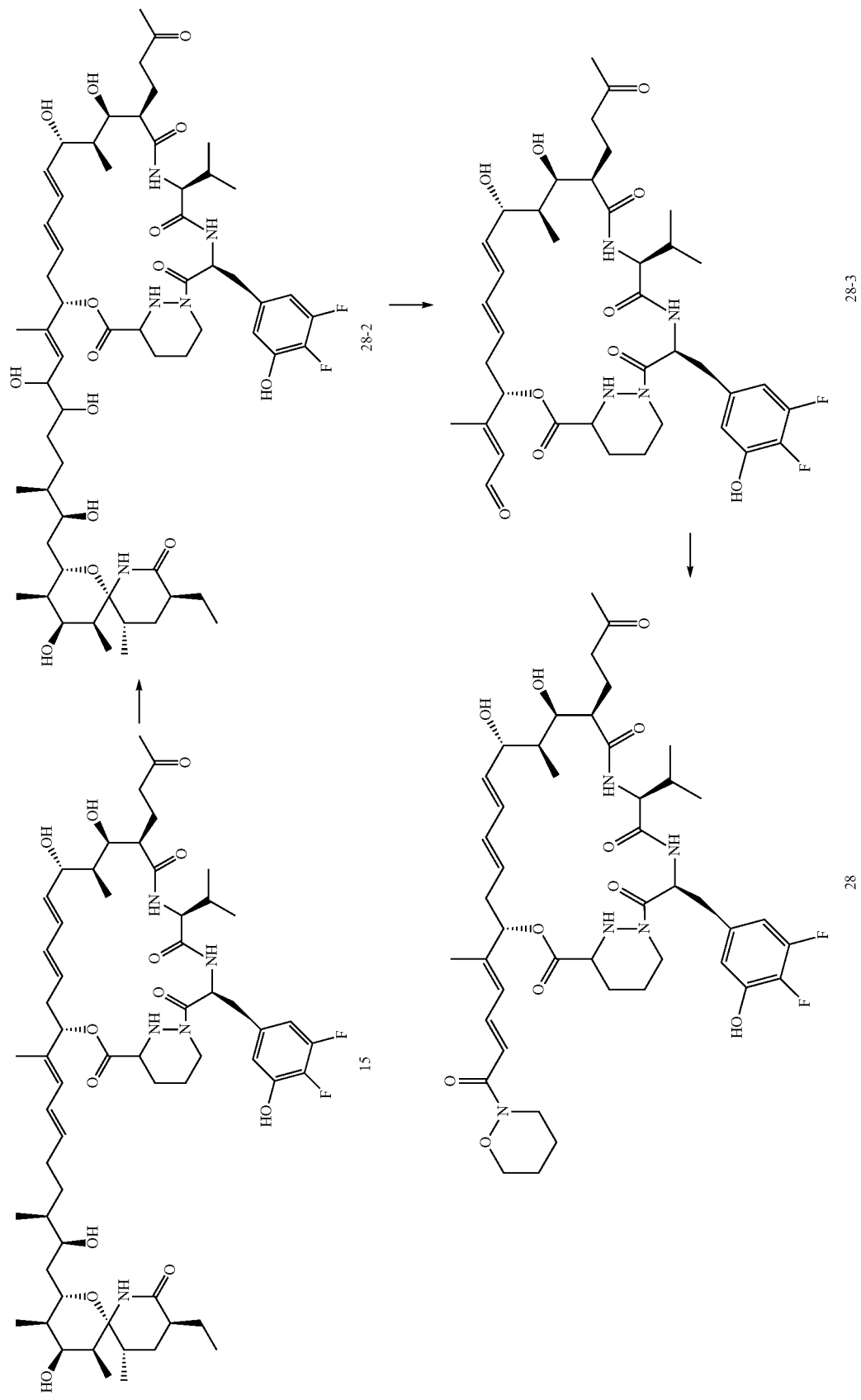

To a stirred solution of 15 (349 mg, 0.31 mmol), (DHQ)₂PHAL (14 mg, 0.0186 mmol), osmium tetroxide (0.117 mL, 0.0093 mmol) in tert-butyl alcohol (2.5 wt %, 0.079 mmol/ml), and methanesulfonamide (59 mg, 0.62 mmol) in 15 mL tert-butyl alcohol was added at room temperature, a solution of potassium ferricyanide (128 mg, 0.93 mmol) and potassium carbonate (306 mg, 0.93 mmol) in 15 mL water, resulting in a brown emulsion. After 2 h a solution of sodium sulfite was added, and stirring was continued for 20 min. The resulting mixture was extracted with ethyl acetate (3×50 ml). The combined organic layers were washed with brine, dried over anhydrous sodium sulfate, filtered, and concentrated under reduced pressure, purified by reverse-phase flash chromatography to yield 28-2 as a white solid.

To a stirred solution of 28-2 (170 mg, 0.1466 mmol) in 15 mL of a 2:1 mixture of THF and water was added sodium periodate (62 mg, 0.2931 mmol). The resulting mixture was stirred at room temperature for 3 h, and then saturated aqueous sodium bicarbonate was added. This mixture was extracted with three portions of ethyl acetate. The combined organic layers were washed with one portion of water and two portions of saturated brine, dried over anhydrous sodium sulfate, filtered, and concentrated under reduced pressure. The residue was purified by reverse-phase flash chromatography to yield 28-3 as a white solid.

To a solution of 21 (41 mg, 0.155 mmol) in THF (1.0 mL) was added NaH (2.3 mg, 0.0575 mmol) in anhydrous THF (0.2 mL) at 0° C. with stirring. The solution was then stirred at 20° C. until it became clear. Then 28-3 (30 mg, 0.0387 mmol) was added to the clear solution and the mixture stirred at 20° C. for 2 h. The mixture was quenched with water (10 mL) and extracted with ethyl acetate (3×20 mL). The organic layer was washed with brine and dried over Na₂SO₄, filtered, evaporated. The residue was purified by preparative HPLC to obtained 28 as a white solid.

Example 19

Preparation of Compound 29

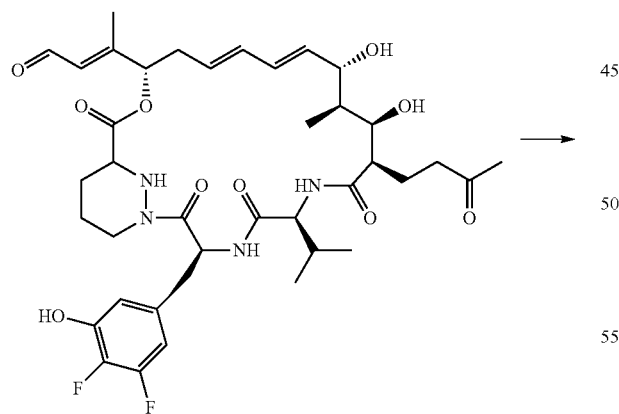

28-3

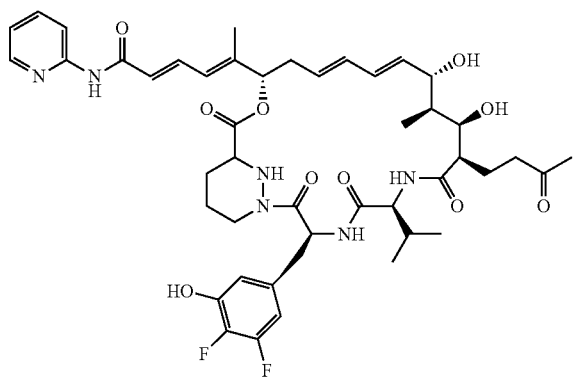

29

To a solution of 22 (42 mg, 0.155 mmol) in THF (1.0 mL) was added NaH (2.3 mg, 0.0575 mmol) in anhydrous THF (0.2 mL) at 0° C. with stirring. The solution was then stirred at 20° C. until it became clear. Then 28-3 (30 mg, 0.0387 mmol) was added to the clear solution and the mixture stirred at 20° C. for 2 h. The mixture was quenched with water (10 mL) and extracted with ethyl acetate (3×20 mL). The organic layer was washed with brine and dried over Na₂SO₄, filtered, evaporated. The residue was purified by preparative HPLC to obtained 29 as a white solid.

Example 20

Preparation of Compound 30

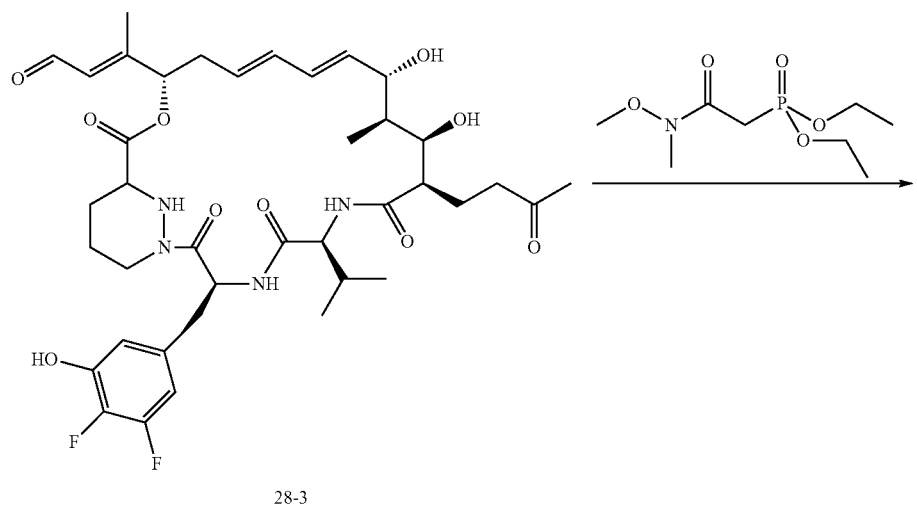

28-3

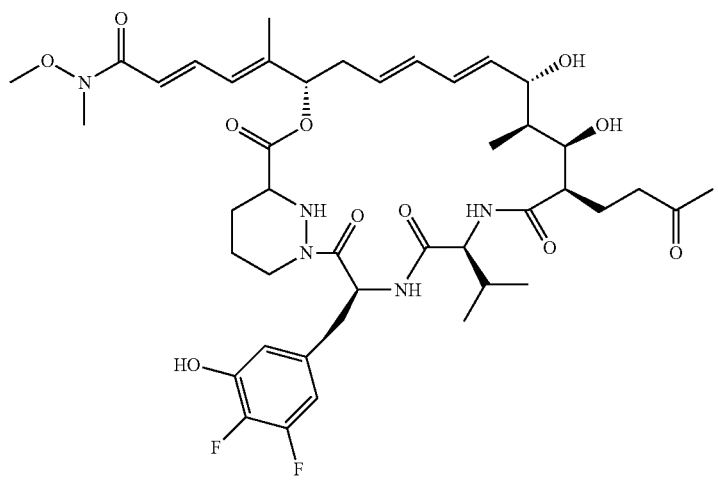

30

To a solution of diethyl (2-(methoxy(methyl)amino)-2-oxoethyl)phosphonate (37 mg, 0.155 mmol) in THF (1.0 mL) was added NaH (2.3 mg, 0.0575 mmol) in anhydrous THF (0.2 mL) at 0° C. with stirring. The solution was then stirred at 20° C. until it became clear. Then 28-3 (30 mg, 0.0387 mmol) was added to the clear solution and the mixture stirred at 20° C. for 2 h. The mixture was quenched with water (10 mL) and extracted with ethyl acetate (3×20 mL). The organic layer was washed with brine and dried over $Na_2SO_4$, filtered, evaporated. The residue was purified by preparative HPLC to obtained 30 as a white solid.

Example 21

Biological Data—HCV Replicon and Analysis

Compounds were analysed in the genotype 1b replicon assay using Huh5.2 cells as described in the General Methods. Cyclosporine A, 1, DEBIO-025, 2, sanglifehrin A, 5, and the hydroxymacrocycle, 6 were included as a comparison.

| Compound | EC50 (μM) | CC50 (μM) | Selectivity index (CC50/EC50) |
|---|---|---|---|
| Cyclosporine A, 1 | 0.62 | 28 | 52 |
| DEBIO-025, 2 | 0.096 | 11.2 | 111 |
| Sanglifehrin A, 5 | 0.318 | 9.1 | 28.7 |
| Hydroxymacrocycle, 6 | 8.4 | 83.6 | 9.9 |
| 23 | 0.067 | >100 | >1493 |
| 24 | 0.033 | >100 | >3030 |
| 25 | 0.066 | >100 | >1515 |
| 26 | 0.1 | >100 | >1000 |
| 27 | 0.121 | >100 | >826 |

As can be seen, the compounds of the invention, 23, 24, 25, 26 and 27 are all significantly more potent in the Huh5.2 replicon assay (as shown by the low $EC_{50}$), with significantly better selectivity against the cell line (as shown by a high selectivity index) as compared to CsA, Debio-025, SfA and the hydroxymacrocycle.

Example 22

Biological Data—Activity Against HIV

Compounds were analysed in an HIV antiviral assay using HeLa cells as described in the General Methods. Cyclosporine A, 1, DEBIO-025, 2, and the HIV antivirals emtricitabine and tenofovir were included as a comparison.

| Compound | HeLa cells $EC_{50}$ (μM) |
|---|---|
| Cyclosporine A, 1 | 5.3 |
| DEBIO-025, 2 | 1.5 |
| Emtricitabine | 0.4 |
| Tenofovir | 1.05 |
| 24 | 0.13 |

As can be seen, the compound of the invention, 24, is significantly more potent than CsA, DEBIO-025, emtricitabine and tenofovir at inhibiting HIV infection in this assay.

Example 23

Biological Data—Mouse In Vivo Oral and iv PK

To assess the pharmacokinetics of the compounds in an in vivo setting, compounds were dosed po at 10 or 5 mg/kg and iv at 1 mg/kg to groups of CD1 mice. Pharmacokinetic analysis was carried out as described in the general methods. The PK parameters are shown below.

| Compound | Dose level (mg/kg) | Clearance (L/hr/kg) | po $AUC_{last}$ (ng*hr/mL) |
|---|---|---|---|
| Sanglifehrin A, 5 | 10 | 0.054 | 2332 |
| 23 | 5 | 0.039 | 2760 |
| 24 | 5 | 0.017 | 8223 |

As can be seen, compounds 23 and 24 have reduced clearance and increased oral exposure (as shown by a high po $AUC_{last}$), compared to sanglifehrin A.

Example 24

Biological Data—Inhibition of CypA PPlase Activity

To assess the direct inhibition of CypA Peptidyl Prolyl cis-trans Isomerase (PPlase) activity, a method was used as described in the general methods. Cyclosporine A, 1, DEBIO-025, 2 and Sanglifehrin A, 5 were included as controls.

| Compound | CypA PPlase $IC_{50}$ (nM) |
|---|---|
| Cyclosporine A, 1 | 9.7 |
| DEBIO-025, 2 | 0.8 |
| Sanglifehrin A, 5 | 2.4 |
| 23 | 0.33 |
| 24 | 0.31 |
| 25 | 1.15 |
| 27 | 0.35 |

As can be seen, compounds of the invention, 23, 24, 25 and 27 all inhibit CypA PPlase activity more potently than Sanglifehrin A, DEBIO-025 and Cyclosporine A.

Example 25

Biological Data—Inhibition of Bilirubin Transporters

To assess the potential of off-target inhibition of bilirubin transporters, thought to be the reason for the dose-limiting hyperbilirubinaemia seen with DEBIO-025, in vitro analysis of transporter inhibition was carried out as described in the general methods.

| Compound | OATP1B1 $IC_{50}$ (μM) | OATP1B3 $IC_{50}$ (μM) | MRP2 $IC_{50}$ (μM) | MRP3 $IC_{50}$ (μM) |
|---|---|---|---|---|
| Cyclosporine A, 1 | 0.85 | 0.13 | 4.1 | 3.1 |
| DEBIO-025, 2 | 0.45 | 0.19 | 16.0 | >50 |
| 24 | 4.3 | 1.8 | >50 | >50 |

As can be seen, the compound of the invention, 24, shows much less inhibition of conjugated and unconjugated bilirubin transporters as compared to DEBIO-025 and Cyclosporine A.

Example 26

Biological Data—Inhibition of Xenobiotic Transporters

To assess the potential of Drug Drug Interactions (DDIs) via inhibition of xenobiotic transporters, in vitro analysis of P-glycoprotein (Pgp/MDR1) and Bile Salt Export Pump (BSEP) inhibition was carried out as described in the general methods.

| Compound | Pgp $IC_{50}$ (μM) | BSEP $IC_{50}$ (μM) |
|---|---|---|
| Cyclosporine A, 1 | 0.73 | 0.46 |
| DEBIO-025, 2 | 0.72 | 0.18 |
| 24 | >50 | 12.3 |

As can be seen, the compound of the invention, 24, shows much less inhibition of xenobiotic transporters, potentially involved in Drug-Drug Interactions, as compared to DEBIO-025 and Cyclosporine A.

References

Appel, N., T. Schaller, et al. (2006). "From structure to function: new insights into hepatitis C virus RNA replication." *J Biol Chem* 281(15): 9833-6.

Banteli, R., J. Wagner, et al. (2001). "Synthesis of derivatives of the novel cyclophilin-binding immunosuppressant sanglifehrin A with reduced numbers of polar functions." *Bioorg Med Chem Lett* 11(12): 1609-12.

Chatterji, U., M. Bobardt, et al. (2009). "The isomerase active site of cyclophilin a is critical for HCV replication." *J Biol Chem*.

Colgan, J., M. Asmal, et al. (2000). "Isolation, characterization and targeted disruption of mouse ppia: cyclophilin A is not essential for mammalian cell viability." *Genomics* 68(2): 167-78.

Crabbe, R., G. Vuagniaux, et al. (2009). "An evaluation of the cyclophilin inhibitor Debio 025 and its potential as a treatment for chronic hepatitis C." *Expert Opin Investig Drugs* 18(2): 211-20.

Dolinski, K., S. Muir, et al. (1997). "All cyclophilins and FK506 binding proteins are, individually and collectively, dispensable for viability in *Saccharomyces cerevisiae.*" *Proc Natl Acad Sci USA* 94(24): 13093-8.

E. Lawitz, R. R., T. Nguyen, M. Huang, J. Ke, J. Praestgaard, D. Serra, M. Koziel, T. Evans (2009). "Safety And Antiviral Efficacy Of 14 Days Of The Cyclophilin Inhibitor Nim811 In Combination With Pegylated Interferon 0.2a In Relapsed Genotype 1 Hcv Infected Patients." *Journal of Hepatology* 50(S1): S379.

Egorin, M. J., T. F. Lagattuta, et al. (2002). "Pharmacokinetics, tissue distribution, and metabolism of 17-(dimethylaminoethylamino)-17-demethoxygeldanamycin (NSC 707545) in CD2F1 mice and Fischer 344 rats." *Cancer Chemother Pharmacol* 49(1): 7-19.

Fehr, T., J. Kallen, et al. (1999). "Sanglifehrins A, B, C and D, novel cyclophilin-binding compounds isolated from *Streptomyces* sp. A92-308110. II. Structure elucidation, stereochemistry and physico-chemical properties." *J Antibiot (Tokyo)* 52(5): 474-9.

Flisiak, R., A. Horban, et al. (2008). "The cyclophilin inhibitor Debio-025 shows potent anti-hepatitis C effect in patients coinfected with hepatitis C and human immunodeficiency virus." *Hepatology* 47(3): 817-26.

Furniss, B. S., Furniss, A. I., Vogel, A. I., Ed. (1989). *Vogel's Textbook of Practical Organic Chemistry*, Prentice Hall.

Gaither, L. A., Borawski, J., Anderson, L. J., Balabanis, K. A. et al., (2010). "Multiple cyclophilins involved in different cellular pathways mediate HCV replication" *Virology* 397: 43-55

Glavinas, H., Krajcsi, P., Cserepes, J., Sarkadi, B. (2004). "The role of ABC transporters in drug resistance, metabolism and toxicity." *Curr. Drug. Deliv.* 1(1): 27-42.

Gomez, L., H. Thibault, et al. (2007). "Inhibition of mitochondrial permeability transition improves functional recovery and reduces mortality following acute myocardial infarction in mice." *Am J Physiol Heart Circ Physiol* 293 (3): H1654-61.

Goto, K., Watashi, K., Inoue, D., Hijikata, M., Shimotohno, K. (2009) "Identification of cellular and viral factors related to anti-hepatitis C virus activity of cyclophilin inhibitor" *Cancer Science* 100(10): 1943-1950

Hanoulle, X., Badillo A, Wieruszeski J M, Verdegem D, Landrieu I, Bartenschlager R, Penin F, Lippens G (2009). "Hepatitis C virus NS5A protein is a substrate for the Peptidyl-Prolyl cis/trans isomerase activity of Cyclophilins A and B." *J Biol. Chem.*

Hartel, C., P. Iblher, et al. (2006). "Immunosuppressive activity of the immunophilin-binding drug Sanglifehrin A in human whole blood: potent inhibition of interleukin-6 produced by lymphocytes and monocytes." *Scand J Immunol* 63(1): 26-34.

Herrler, M., H. Bang, et al. (1994). "Cloning and characterization of ppiB, a *Bacillus subtilis* gene which encodes a cyclosporin A-sensitive peptidyl-prolyl cis-trans isomerase." *Mol Microbiol* 11(6): 1073-83.

Hite, M., Turner, S., Federici, C. (2003). "Part 1: Oral delivery of poorly soluble drugs". *Pharmaceutical Manufacturing and Packing Sourcer*. Summer 2003 issue.

Immecke, S. N., Baal., N, et al. (2011). "The Cyclophilin-Binding Agent Sanglifehrin A Is a Dendritic Cell Chemokine and Migration Inhibitor." PLOS one 6(3):e18406

Inoue, K., K. Sekiyama, et al. (2003). "Combined interferon alpha2b and cyclosporin A in the treatment of chronic hepatitis C: controlled trial." *J Gastroenterol* 38(6): 567-72.

Inoue, K., T. Umehara, et al. (2007). "Evaluation of a cyclophilin inhibitor in hepatitis C virus-infected chimeric mice in vivo." *Hepatology* 45(4): 921-8.

Ishii, N., K. Watashi, et al. (2006). "Diverse effects of cyclosporine on hepatitis C virus strain replication." *J Virol* 80(9): 4510-20.

Ke, J., E. L., R. Rozier, T. Marbury, N. Nguyen, D. Serra, K. Dole, J. Praestgaard, M. Huang, T. Evans (2009). "Safety, And Tolerability Of Nim811, A Novel Cyclophilin Inhibitor For Hcv, Following Single And Multiple Ascending Doses In Healthy Volunteers And Hcv-Infected Patients." *Journal of Hepatology* 50(S1): S229.

Jacobson, I., McHutchison, JG, Sulkowski, M. (2007). *Gastroenterol & Hepatol* 3(S34): 1-10.

Kallen, J., R. Sedrani, et al. (2005). "Structure of human cyclophilin A in complex with the novel immunosuppressant sanglifehrin A at 1.6 A resolution." *J Biol Chem* 280 (23): 21965-71.

Kawasaki, H., E. S. Mocarski, et al. (2007). "Cyclosporine inhibits mouse cytomegalovirus infection via a cyclophilin-dependent pathway specifically in neural stem/progenitor cells." *J Virol* 81(17): 9013-23.

Konig, J. H., Glaeser, M. Keiser, K. Mandery, U. Klotz and M. F. Fromm (2010), *Drug Metab Dispos,* 39, 1097-1102.

Manns, M. P., G. R. Foster, et al. (2007). "The way forward in HCV treatment—finding the right path." *Nat Rev Drug Discov* 6(12): 991-1000.

Martin Cabrejas, L. M., S. Rohrbach, et al. (1999). "Macrolide Analogues of the Novel Immunosuppressant Sanglifehrin New Application of the Ring-Closing Metathesis Reaction." *Angew Chem Int Ed Engl* 38(16): 2443-2446.

Mathy, J. E., S. Ma, et al. (2008). "Combinations of cyclophilin inhibitor NIM811 with hepatitis C Virus NS3-4A Protease or NS5B polymerase inhibitors enhance antiviral activity and suppress the emergence of resistance." *Antimicrob Agents Chemother* 52(9): 3267-75.

Melnikova, I. (2008). "Hepatitis C therapies." *Nature Rev Drug Disc* 7: 799-800.

Metternich, R., Denni, D., That, B, Sedrani, R. (1999). "Toward a Total Synthesis of the Immunosuppressant Sanglifehrin A. Preparation of Two Relay Compounds by Degradation and Their Use in the Reassembly of the Natural Product." *J. Org. Chem.* 64: 9632-9639.

Millay, D. P., M. A. Sargent, et al. (2008). "Genetic and pharmacologic inhibition of mitochondrial-dependent necrosis attenuates muscular dystrophy." *Nat Med* 14(4): 442-7.

Nelson, D. R., Ghalib, R. H., Sulkowski, M., Schiff, E., Rustgi, V., Pockros, P. J., Wang, C., Decosterd Kerhuel, D., and P. Grosgurin, Porchet, H., Crabbe, R. (2009). "Efficacy And Safety Of The Cyclophilin Inhibitor Debio 025 In Combination With Pegylated Interferon Alpha-2a And Ribavirin In Previously Null-Responder Genotype 1 Hcv Patients." *Journal of Hepatology* 50(S1): S40.

Niwa, T., Yamamoto, S, Saito, M, Shiraga, T, Takagi, A. (2007). "Effect of Cyclosporine and Tacrolimus on Cytochrome P450 Activities in Human Liver Microsomes." *Yakugaku Zasshi* 127(1): 209-216.

Paeshuyse, J., A. Kaul, et al. (2006). "The non-immunosuppressive cyclosporin DEBIO-025 is a potent inhibitor of hepatitis C virus replication in vitro." *Hepatology* 43(4): 761-70.

Parfieniuk, A., J. Jaroszewicz, et al. (2007). "Specifically targeted antiviral therapy for hepatitis C virus." *World J Gastroenterol* 13(43): 5673-81.

Pawlotsky, J. M. (2000). "Hepatitis C virus resistance to antiviral therapy." *Hepatology* 32(5): 889-96.

Pawlotsky, J. M. (2005). "Current and future concepts in hepatitis C therapy." *Semin Liver Dis* 25(1): 72-83.

Pawlotsky, J. M. (2006). "Virology of hepatitis B and C viruses and antiviral targets." *J Hepatol* 44(1 Suppl): S10-3.

Pemberton, T. J. and J. E. Kay (2003). "Cyclophilin sensitivity to sanglifehrin A can be correlated to the same specific tryptophan residue as cyclosporin A." *FEBS Lett* 555(2): 335-40.

Pockros, P. (2008). "Emerging Therapies for Chronic Hepatitis C Virus." *Gastroenterol and Hepatology* 4(10): 729-734.

Ptak, R. G., P. A. Gallay, et al. (2008). "Inhibition of human immunodeficiency virus type 1 replication in human cells by Debio-025, a novel cyclophilin binding agent." *Antimicrob Agents Chemother* 52(4): 1302-17.

Qu, X., Jiang, N. et al., (2011). "Cloning, sequencing and characterization of the biosynthetic gene cluster of sanglifehrin A, a potent cyclophilin inhibitor." *Mol. Biosyst.* 7:852-861

Robida, J. M., H. B. Nelson, et al. (2007). "Characterization of hepatitis C virus subgenomic replicon resistance to cyclosporine in vitro." *J Virol* 81(11): 5829-40.

Hopkins, S. D. H., E. Gavis, J. Lalezari, E. Glutzer, B. DiMassimo, P. Rusnak, S. Wring, C. Smitley, Y. and Ribeill (2009). "Safety, plasma pharmacokinetics, and anti-viral activity of SCY-635 in adult patients with chronic hepatitis C virus infection." *Journal of Hepatology* 50(S1): S36.

Sanglier, J. J., V. Quesniaux, et al. (1999). "Sanglifehrins A, B, C and D, novel cyclophilin-binding compounds isolated from *Streptomyces* sp. A92-308110.1. Taxonomy, fermentation, isolation and biological activity." *J Antibiot (Tokyo)* 52(5): 466-73.

Schneider, M. D. (2005). "Cyclophilin D: knocking on death's door." *Sci STKE* 2005 (287): pe26.

Sedrani, R., J. Kallen, et al. (2003). "Sanglifehrin-cyclophilin interaction: degradation work, synthetic macrocyclic analogues, X-ray crystal structure, and binding data." *J Am Chem Soc* 125(13): 3849-59.

Seden, K. D. Back and S. Khoo (2010), *J Antimicrob Chemother,* 65, 1079-1085.

Smith, M. B. a. M., J., Ed. (2001). *March's advanced organic chemistry*, John Wiley and Sons Inc., UK.

Steinschulte, C., T. Taner, et al. (2003). "Cutting edge: sanglifehrin A, a novel cyclophilin-binding immunosuppressant blocks bioactive IL-12 production by human dendritic cells." *J Immunol* 171(2): 542-6.

Strader, D. B., T. Wright, et al. (2004). "Diagnosis, management, and treatment of hepatitis C." *Hepatology* 39(4): 1147-71.

Tropschug, M., I. B. Barthelmess, et al. (1989). "Sensitivity to cyclosporin A is mediated by cyclophilin in *Neurospora crassa* and *Saccharomyces cerevisiae.*" *Nature* 342(6252): 953-5.

Vrolijk, J. M., A. Kaul, et al. (2003). "A replicon-based bioassay for the measurement of interferons in patients with chronic hepatitis C." *J Virol Methods* 110(2): 201-9.

Wring, S., C. Wille, C. Rewerts, R. Randolph, A. Scribner and S. Hopkins (2010), *Journal of Hepatology,* 52, S263

Yang, F., J. M. Robotham, et al. (2008). "Cyclophilin A is an essential cofactor for hepatitis C virus infection and the principal mediator of cyclosporine resistance in vitro." *J Virol* 82(11): 5269-78.

Zenke, G., U. Strittmatter, et al. (2001). "Sanglifehrin A, a novel cyclophilin-binding compound showing immunosuppressive activity with a new mechanism of action." *J Immunol* 166(12): 7165-71.

Zeuzem, S, and E. Herrmann (2002). "Dynamics of hepatitis C virus infection." *Ann Hepatol* 1(2): 56-63.

Zhang, L. H. and J. O. Liu (2001). "Sanglifehrin A, a novel cyclophilin-binding immunosuppressant, inhibits IL-2-dependent T cell proliferation at the G1 phase of the cell cycle." *J Immunol* 166(9): 5611-8.

All references including patent and patent applications referred to in this application are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

---

The invention claimed:

1. A compound of formula (I):

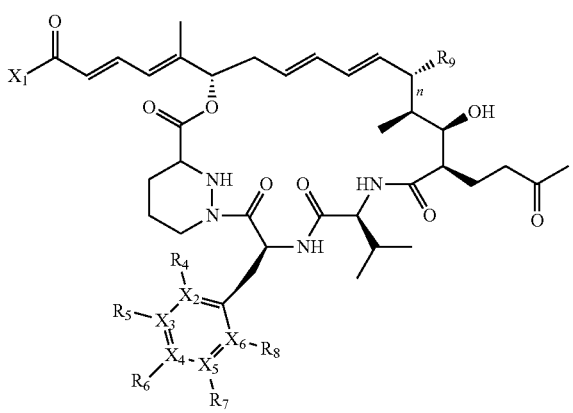

Formula (I)

wherein:

the moiety $X_1$ represents —$OR_1$, —$NR_1R_2$ or $R_3$;

$R_1$, $R_2$ and $R_3$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocyclic aryl or monocyclic heteroaryl;

and wherein one or more carbon atoms of $R_1$, $R_2$ and $R_3$ not being part of an aryl or heteroaryl group are optionally replaced by a heteroatom selected from O, N and $S(O)_p$ in which p represents 0, 1 or 2 and wherein one or more carbon atoms of $R_1$, $R_2$ and $R_3$ are optionally replaced by carbonyl;

or $R_1$ and $R_2$ are linked such that $\_NR_1R_2$ represents a saturated or unsaturated heterocyclic ring containing the specified nitrogen atom and wherein one or more carbon atoms of said ring are optionally replaced by a further heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;

and wherein one or more carbon atoms of an $R_1$, $R_2$ and $R_3$ group may optionally be substituted by one or more halogen atoms;

or $R_1$ and/or $R_2$ represents hydrogen;

$R_9$ represents H or OH;

n represents a single or double bond, save that when n represents a double bond $R_9$ represents H;

$R_4$, $R_5$, $R_6$, $R_7$ and $R_8$ independently represent H, F, Cl, Br, alkenyl or alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms;

$X_2$, $X_3$, $X_4$, $X_5$ and $X_6$ independently represent C or N, and in the case of any of these groups representing N the attached substituent is absent;

with the proviso that where $R_4$, $R_6$, $R_7$ and $R_8$ all represent H and $X_2$, $X_3$, $X_4$, $X_5$ and $X_6$ all represent C, then $R_5$ cannot represent —OH, —Oalkyl or —O(CO)alkyl;

including any tautomer thereof; and including a methanol adduct thereof in which a ketal is formed by the combination of the C-53 keto and the C-15 hydroxyl group and methanol;

or a pharmaceutically acceptable salt thereof.

2. A compound according to claim 1 wherein n represents a single bond.

3. A compound according to claim 1 wherein $R_9$ represents OH.

4. A compound according to claim 1 wherein $X_2$ represents C.

5. A compound according to claim 1 wherein $X_3$ represents C.

6. A compound according to claim 1 wherein $X_4$ represents C.

7. A compound according to claim 1 wherein $X_5$ represents C.

8. A compound according to claim 1 wherein $X_6$ represents C.

9. A compound according to claim 1 wherein $R_4$ represents H.

10. A compound according to claim 1 wherein $R_8$ represents H.

11. A compound according to claim 1 wherein $R_5$ represents OH.

12. A compound according to claim 1 wherein $R_6$ represents H, Me or F.

13. A compound according to claim 1 wherein $R_7$ represents H or F.

14. A compound according to claim 1 wherein $R_6$ and/Or $R_7$ represents F.

15. A compound according to claim 1 wherein $X_1$ represents $NR_1R_2$.

16. A compound according to claim 15 wherein $R_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl and $R_2$ represents H, alkyl, alkenyl or —Oalkyl.

17. A compound according to claim 15 wherein $NR_1R_2$ represents morpholinyl, oxazinane or one of the groups disclosed in the following table:

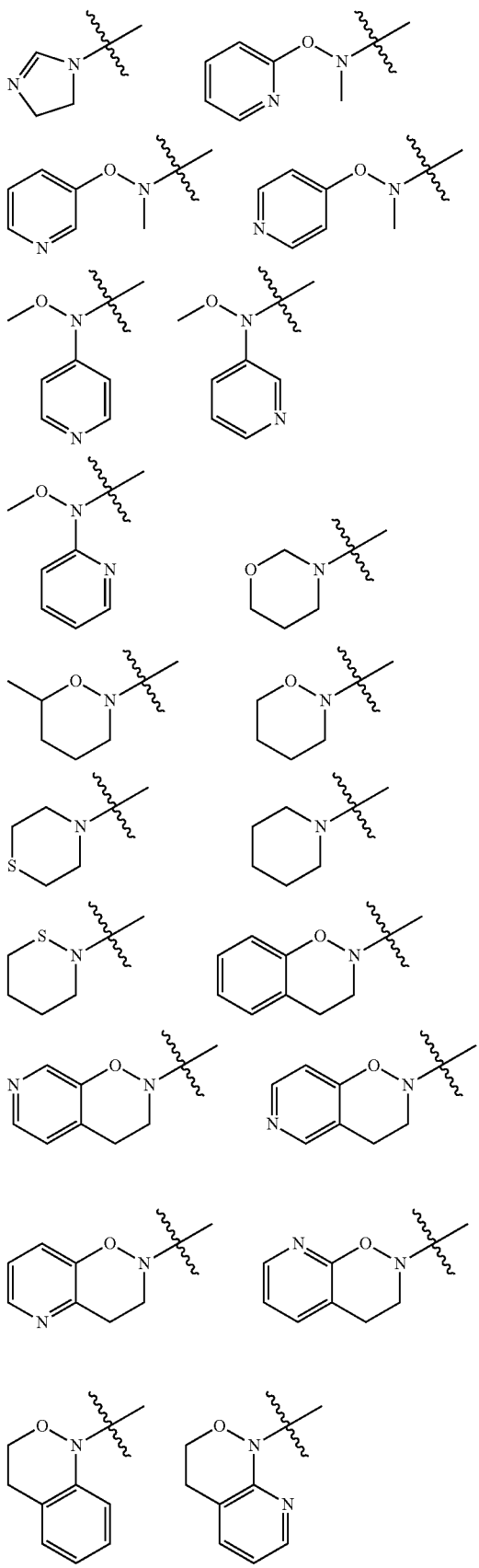

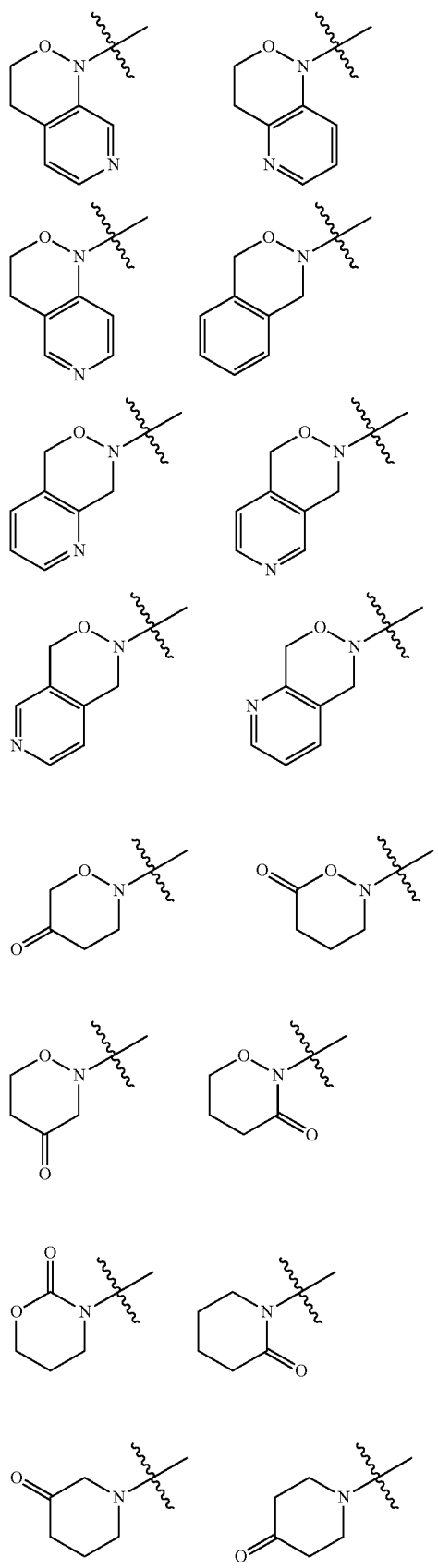
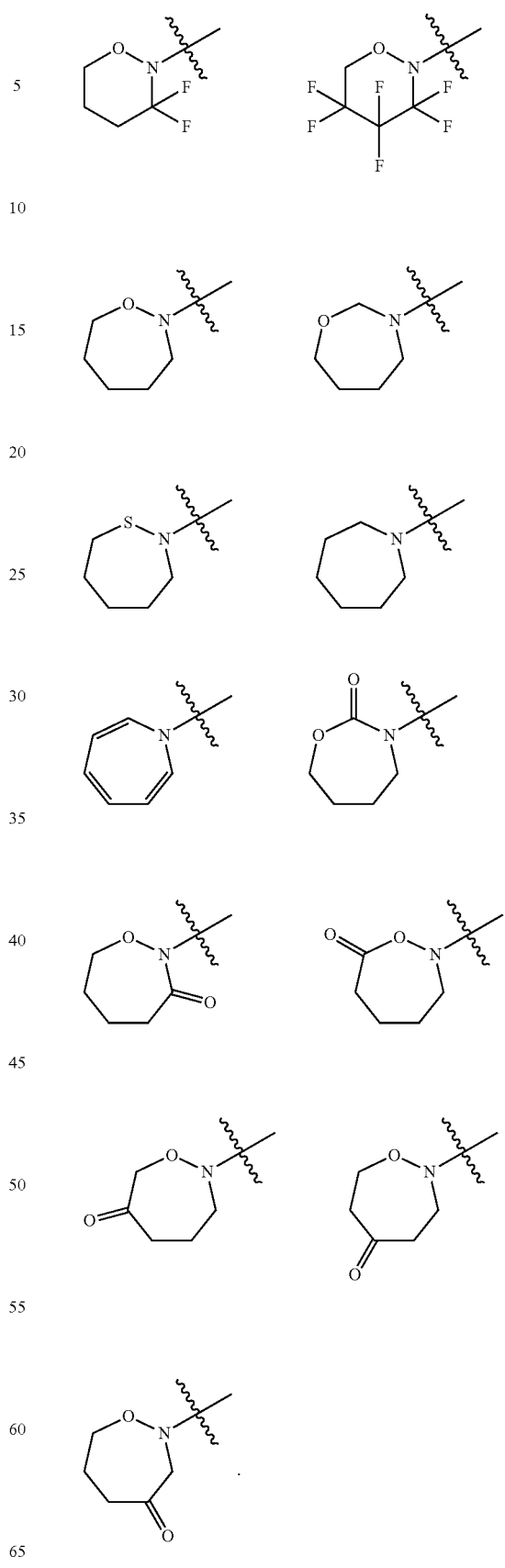

18. A compound according to claim 1 selected from:
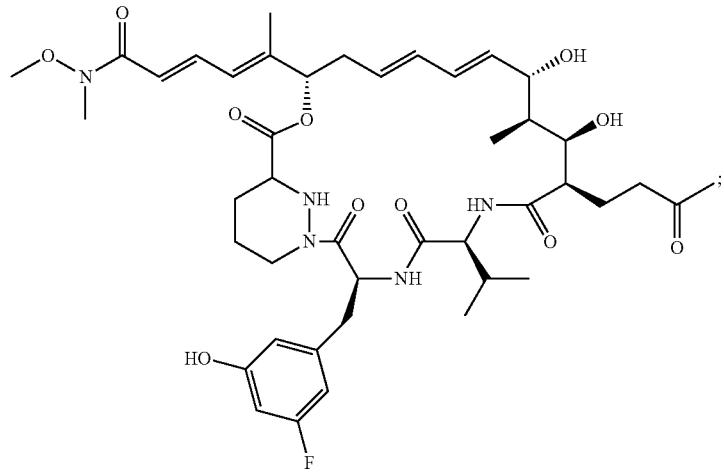
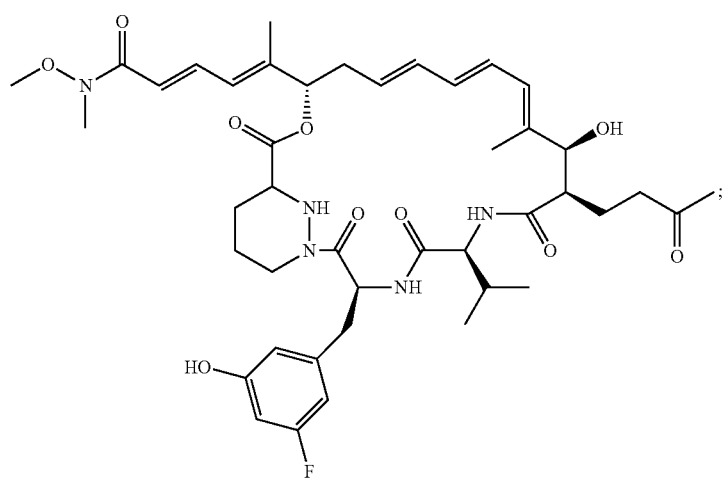
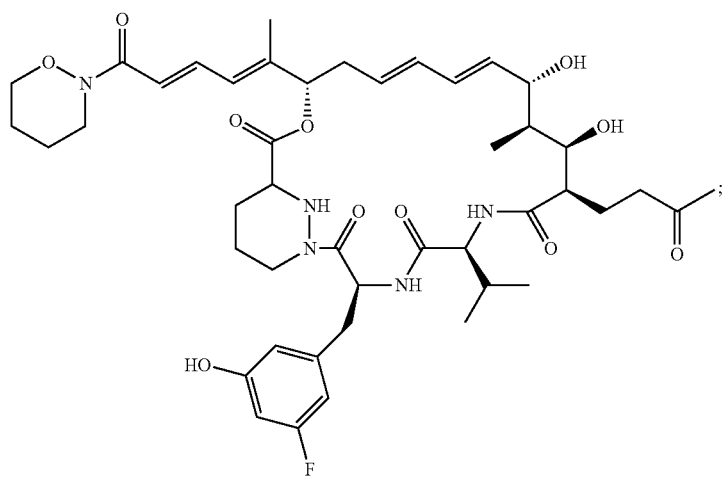

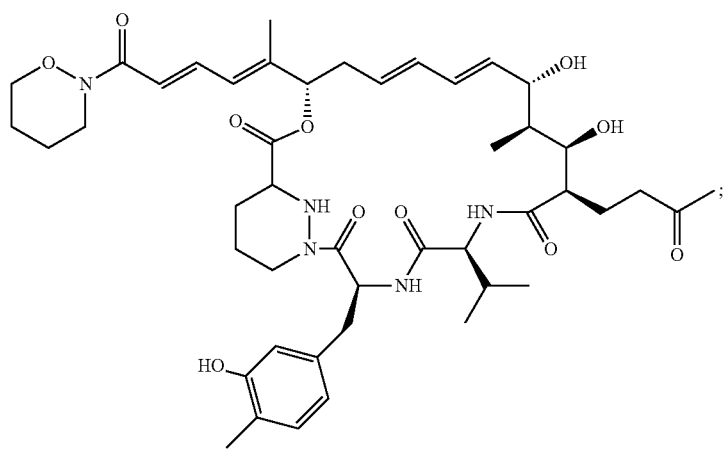
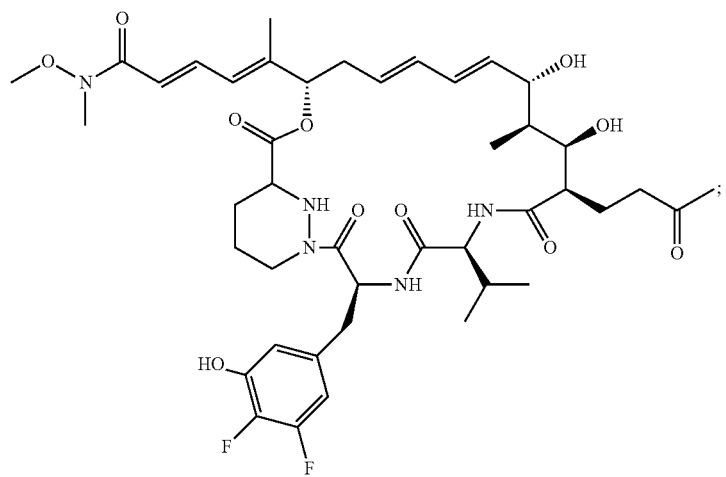
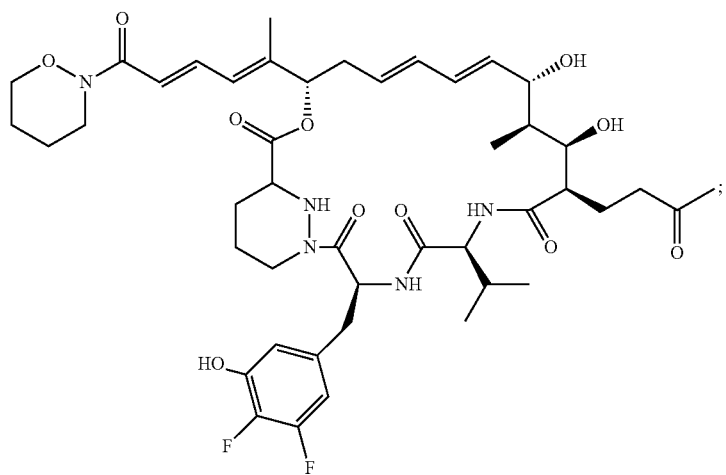

-continued

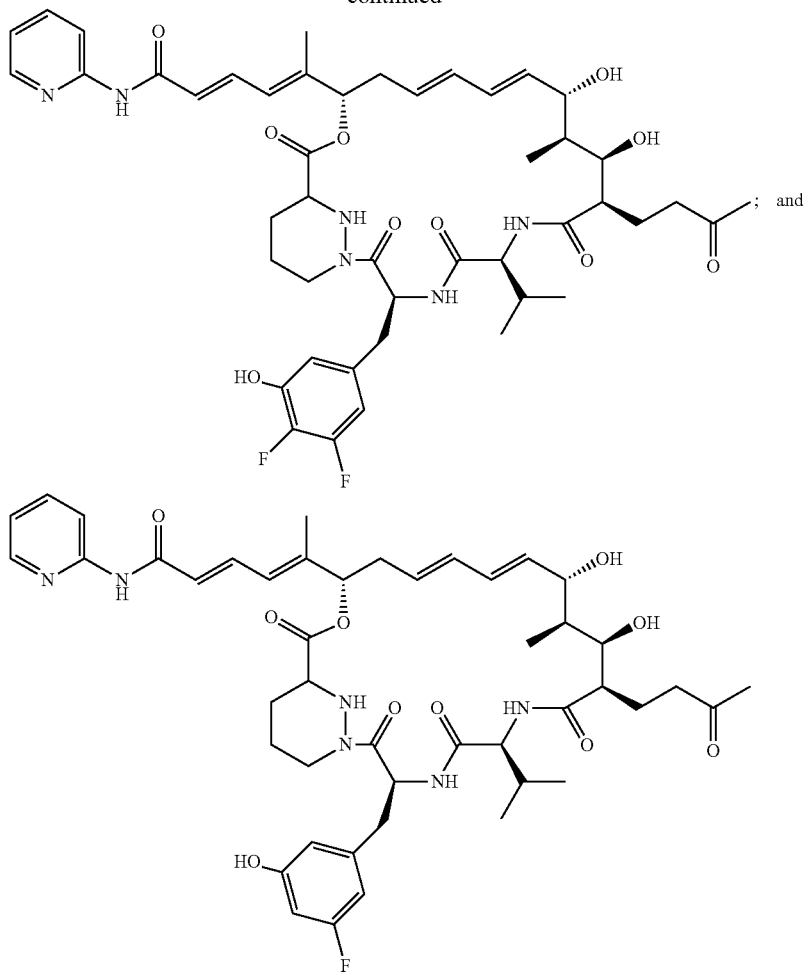

including any tautomer thereof; or an isomer thereof in which the C26, 27 C=C bond shown as trans is cis; and including a methanol adduct thereof in which a ketal is formed by the combination of the C-53 keto, if present, and the C-15 hydroxyl group and methanol;
or a pharmaceutically acceptable salt thereof.

19. A pharmaceutical composition comprising a compound according to claim 1 together with a pharmaceutically acceptable diluent or carrier.

20. A pharmaceutical composition comprising a compound according to claim 1 together with a pharmaceutically acceptable diluent or carrier further comprising a second or additional active ingredient.

21. A method of treatment of an HCV or HIV infection or for use as an immunosuppressant or an anti-inflammatory agent which comprises administering to a subject a therapeutically effective amount of a compound according to claim 1.

22. A process for preparing a compound according to claim 1 which comprises reacting a compound of formula V Formula V

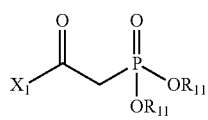

wherein $X_1$ is as defined in claim 1 and each $R_{11}$ is independently $C_{1-4}$alkyl or benzyl;

with an aldehydic macrocyle (compound of formula VI):

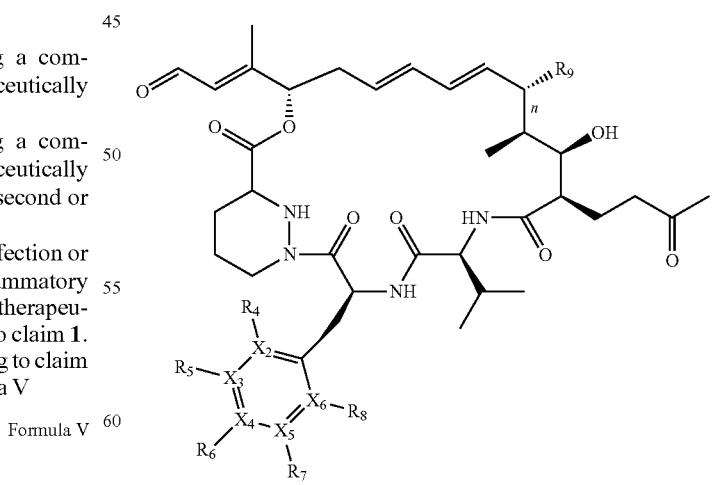

wherein $X_2$, $X_3$, $X_4$, $X_5$, $X_6$, $R_4$, $R_5$, $R_6$, $R_7$, $R_8$, $R_9$, and n are as defined in claim 1.

23. A compound of formula (VI):

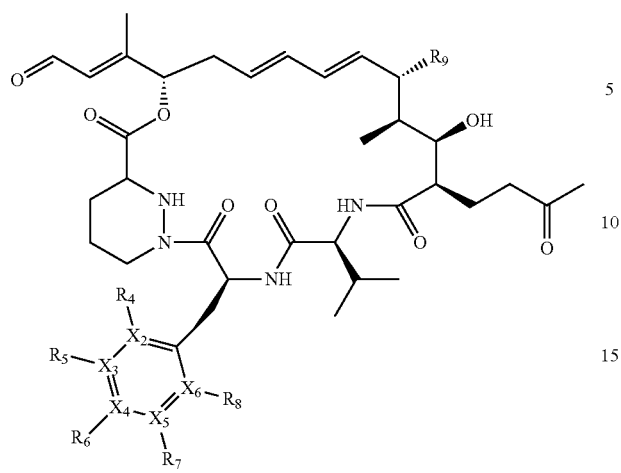

wherein:

$R_9$ represents H or OH;

$R_4, R_5, R_6, R_7$ and $R_8$ independently represent H, F, Cl, Br, alkenyl or alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms;

$X_2, X_3, X_4, X_5$ and $X_6$ independently represent C or N, and in the case of any of these groups representing N the attached substituent is absent;

with the proviso that where $R_4, R_6, R_7$ and $R_8$ all represent H and $X_2, X_3, X_4, X_5$ and $X_6$ all represent C, then $R_5$ cannot represent —OH, —Oalkyl or —O(CO)alkyl.

* * * * *